(12) United States Patent
Asolkar et al.

(10) Patent No.: US 9,084,428 B2
(45) Date of Patent: Jul. 21, 2015

(54) BACILLUS MEGATERIUM BIOACTIVE COMPOSITIONS AND METABOLITES

(71) Applicant: Marrone Bio Innovations, Inc., Davis, CA (US)

(72) Inventors: Ratnakar Asolkar, Davis, CA (US); Ana Lucia Cordova-Kreylos, Davis, CA (US); Margarita Rodriguez, Woodland, CA (US); Carly Todd, Sacramento, CA (US); Debora Wilk, Woodland, CA (US); Pamela Marrone, Davis, CA (US)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 13/832,407

(22) Filed: Mar. 15, 2013

(65) Prior Publication Data

US 2014/0051571 A1 Feb. 20, 2014

Related U.S. Application Data

(60) Provisional application No. 61/683,154, filed on Aug. 14, 2012.

(51) Int. Cl.
| *A01N 63/02* | (2006.01) |
| *A01N 37/10* | (2006.01) |
| *C12P 7/40*  | (2006.01) |
| *C12R 1/11*  | (2006.01) |
| *C12R 1/20*  | (2006.01) |
| *C12N 1/20*  | (2006.01) |

(52) U.S. Cl.
CPC .............. *A01N 63/02* (2013.01); *A01N 37/10* (2013.01); *C12N 1/20* (2013.01); *C12P 7/40* (2013.01); *C12R 1/11* (2013.01)

(58) Field of Classification Search
None
See application file for complete search history.

(56) References Cited

U.S. PATENT DOCUMENTS

| 6,096,306 A * | 8/2000 | Bravo et al. .............. 424/93.461 |
| 7,429,477 B2 | 9/2008 | Johnson |
| 2012/0157304 A1 | 6/2012 | Johnson |

FOREIGN PATENT DOCUMENTS

| EP | 2496536 A2 | 9/2012 |
| WO | WO9628031 | * 9/1996 |

OTHER PUBLICATIONS

Chau et al. (Role of RecA in the Protection of DNA Damage by UV-A in *Escherichia coli*., Journal of Experimental Microbiology and Immunology (2008), vol. 12, pp. 39-44.*
Janousek et al., Control of brown rot and shot hole in almond: 2009 field trial, Department of Plant Pathology UC Davis (2010), pp. 1st-4th.*
Eppinger et al., Genome sequences of the biotechnologically important *Bacillus megaterium* strains QM B1551 and DSM319., J Bacteriol. (Epub Jun. 24, 2011), vol. 193(16), pp. 4199-4213.*
genbank CP001982.1 (last viewed on Dec. 11, 2014).*
Kanjanamaneesthian et al., *Bacillus megaterium* Suppresses Major Thailand Rice Diseases., Asian Journal of Food and Agro-Industry (2009), Special Issue, S154-S159.*

(Continued)

*Primary Examiner* — Alexander Kim
(74) *Attorney, Agent, or Firm* — Ying-Horng Liu

(57) ABSTRACT

Provided are bioactive compositions and metabolites derived from *Bacillus* and particularly *Bacillus megaterium* cultures responsible for controlling pests as well as their methods of use for controlling pests. Further provided are pesticidal *Bacillus megaterium* strains.

13 Claims, 11 Drawing Sheets

(56) References Cited

OTHER PUBLICATIONS

Askoy, H.M., et al. (2008) Isolation of *Bacillus megaterium* from Aphis Pomi (Homoptera: Aphididae) and Assessment of its Pathogenicity. Journal of Plant Pathology. 90(3) 449-452.
El-Hadad, M.L. et al. (2011), The Nematicidal Effect of Some Bacterial Biofertilizers on *Meloidogyne incognita* in Sandy Soil. Brazilian Journal of Microbiology, 42:105-113.
Gu, Y. et al. (2007). Evaluation and identification of potential organic nematicidal volatiles from soil bacteria. Soil Biology and Biochemistry, 39,2567-2575.
Huang, Y. et al. (2010). Characterisation of volatiles produces from *Bacillus megaterium* YFM3.25 and their Nematicidal Activity Against *Meloidogyne incognita*, Eur. J. Plant Pathol 126:417-422.
Oliveira, D. F. et al. (2007). Selection of rhizobacteria able to produce metabolites active against *Meloidogyne exigua*. European Journal of Plant Pathology, 119, 477-479.
Martin, L. et al. (1995). Cloning and Sequencing of the pac gene Encoding the Penicillin G Acylase of *Bacillus megaterium* ATCC 14945. FEMS Microbiology Letters, 125:287-292.
Neipp, P. W. et al. (1999). Evaluation of biocontrol activity of rhizobacteria from Beta vulgaris against *Heterodera schachtii*. Journal of nematology, 31(1), 54-61.
Padgham, J.L. et al. (2007). Biological control potential and modes of action of *Bacillus megaterium* against *Meloidogyne graminicola* on rice. *Crop prot.* 26, 971-977.
Pandey, R. et al. (2011). Enhanced Tolerance of Mentha Arvensis Against *Meloidogyn incognita* (Kofoid and White) Chitwood through Mutualistic Endophytes and PGPRs. Journal of Plant Interactions, 6:4, 247-253.
Suga, K. et al. (1990). Reaction Kinetics and Mechanism of Immobilized Penicillin Acylase from *Bacillus megaterium*. Annals New York Academy of Sciences. 808-815.
Vary, P. (1994). Prime Time for *Bacillus megaterium*. Microbiology, 140:1001-1013.
Vary, P. et al. (2007) *Bacillus Megaterium*—from Simple Soil Bacterium to Industrial Protien Production Host. Appl. Microbial Biotechnol, 76:957-967.

\* cited by examiner

US 9,084,428 B2

SEQUENCE LISTING

```
<160> NUMBER OF SEQ ID NOS: 22

<210> SEQ ID NO 1
<211> LENGTH: 1162
<212> TYPE: DNA
<213> ORGANISM: Bacillus megaterium
<220> FEATURE:
<221> NAME/KEY: misc_feature
<222> LOCATION: (1)..(9)
<223> OTHER INFORMATION: n is a, c, g, or t
```

-continued

```
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (986)..(987)
<223> OTHER INFORMATION: n is a, c, g, or t
<220> FEATURE:
<221> NAME/KEY: misc_feature
<222> LOCATION: (1005)..(1006)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1059)..(1060)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1098)..(1100)
<223> OTHER INFORMATION: n is a, c, g, or t
<220> FEATURE:
<221> NAME/KEY: misc_feature
<222> LOCATION: (1110)..(1112)
<223> OTHER INFORMATION: n is a, c, g, or t
<220> FEATURE:
<221> NAME/KEY: misc_feature
<222> LOCATION: (1115)..(1115)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1121)..(1124)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1137)..(1138)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1150)..(1150)
<223> OTHER INFORMATION: n is a, c, g, or t
<220> FEATURE:
<221> NAME/KEY: misc_feature
<222> LOCATION: (1161)..(1162)
```

<223> OTHER INFORMATION: n is a, c, g, or t

<400> SEQUENCE: 1

```
nnnnnnnnng nnngctataa tgcaagtcga gcgaactgat tagaagcttg cttctatgac     60
gttagcggcg gacgggtgag taacacgtgg gcaacctgcc tgtaagactg ggataacttc    120
gggaaaccga agctaatacc ggataggatc ttctccttca tgggagatga ttgaaagatg    180
gtttcggcta tcacttacag atgggcccgc ggtgcattag ctagttggtg aggtaacggc    240
tcaccaaggc aacgatgcat agccgacctg agagggtgat cggccacact gggactgaga    300
cacggcccag actcctacgg gaggcagcag tagggaatct tccgcaatgg acgaaagtct    360
gacggagcaa cgccgcgtga gtgatgaagg ctttcgggtc gtaaaactct gttgttaggg    420
aagaacaagt acaagagtaa ctgcttgtac cttgacggta cctaaccaga agccacggc     480
taactacgtg ccagcagccg cggtaatacg taggtggcaa gcgttatccg gaattattgg    540
gcgtaaagcg cgcgcaggcg gtttcttaag tctgatgtga agcccacgg ctcaaccgtg    600
gagggtcatt ggaaactggg gaacttgagt gcagaagaga aaagcggaat ccacgtgta    660
gcggtgaaat gcgtagagat gtggaggaac accagtggcg aaggcggctt tttggtctgt    720
aactgacgct gaggcgcgaa agcgtgggga gcaaacagga ttagataccc tggtagtcca    780
cgccgtaacg atgagtgcta agtgttagag ggtttccgcc ctttagtgct gcagctaacg    840
cattaagcac tccgcctggg gagtacnggt cgcaagactg aaactcaaag gaattgacgg    900
gggcncgcac aagcggtgga gcatgtggtt taattcgaag caacgcgaag aaccttacca    960
ggtcttgaca tcctctgaca actctnngat agagcgttcc ccttnnggga cagagtgaca   1020
ggtggngcat gggttgtcgt cagctcntgt cgtgagatnn tgggttaagt cccgcaacga   1080
gcgcaaccnt tgatctannn cagcattcan nggnantct nnnngactgc ngntgannac    1140
cgnagaaagn tggggatgac nn                                             1162
```

<210> SEQ ID NO 2
<211> LENGTH: 1133
<212> TYPE: DNA
<213> ORGANISM: Bacillus megaterium
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (959)..(959)
<223> OTHER INFORMATION: n is a, c, g, or t
<220> FEATURE:
<221> NAME/KEY: misc_feature
<222> LOCATION: (971)..(971)
<223> OTHER INFORMATION: n is a, c, g, or t
<220> FEATURE:
<221> NAME/KEY: misc_feature
<222> LOCATION: (1004)..(1005)
<223> OTHER INFORMATION: n is a, c, g, or t
<220> FEATURE:
<221> NAME/KEY: misc_feature

```
<222> LOCATION: (1012)..(1012)
<223> OTHER INFORMATION: n is a, c, g, or t
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1035)..(1036)
<223> OTHER INFORMATION: n is a, c, g, or t
<220> FEATURE:
<221> NAME/KEY: misc_feature
<222> LOCATION: (1047)..(1048)
<223> OTHER INFORMATION: n is a, c, g, or t
<220> FEATURE:
<221> NAME/KEY: misc_feature
<222> LOCATION: (1055)..(1056)
<223> OTHER INFORMATION: n is a, c, g, or t
<220> FEATURE:
<221> NAME/KEY: misc_feature
<222> LOCATION: (1060)..(1063)
<223> OTHER INFORMATION: n is a, c, g, or t
<220> FEATURE:
<221> NAME/KEY: misc_feature
<222> LOCATION: (1066)..(1066)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t
<220> FEATURE:
<221> NAME/KEY: misc_feature
<222> LOCATION: (1078)..(1078)
<223> OTHER INFORMATION: n is a, c, g, or t
<220> FEATURE:
<221> NAME/KEY: misc_feature
<222> LOCATION: (1092)..(1093)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1106)..(1106)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1118)..(1120)
<223> OTHER INFORMATION: n is a, c, g, or t
<220> FEATURE:
<221> NAME/KEY: misc_feature
<222> LOCATION: (1125)..(1125)
<223> OTHER INFORMATION: n is a, c, g, or t
<220> FEATURE:
```

```
<221> NAME/KEY: misc_feature
<222> LOCATION: (1127)..(1127)
<223> OTHER INFORMATION: n is a, c, g, or t
<220> FEATURE:
<221> NAME/KEY: misc_feature
<222> LOCATION: (1129)..(1133)
<223> OTHER INFORMATION: n is a, c, g, or t

<400> SEQUENCE: 2
nnnnnnnnnn nnnnncgact tcaccccaat catctgtccc accttaggcg gctagctcct      60
tacggttact ccaccgactt cgggtgttac aaactctcgt ggtgtgacgg gcggtgtgta     120
caaggcccgg gaacgtattc accgcggcat gctgatccgc gattactagc gattccagct     180
tcatgtaggc gagttgcagc ctacaatccg aactgagaat ggttttatgg gattggcttg     240
acctcgcggt cttgcagccc tttgtaccat ccattgtagc acgtgtgtag cccaggtcat     300
aagggggcatg atgatttgac gtcatcccca ccttcctccg gtttgtcacc ggcagtcacc     360
ttagagtgcc caactgaatg ctggcaacta agatcaaggg ttgcgctcgt tgcgggactt     420
aacccaacat ctcacgacac gagctgacga caaccatgca ccacctgtca ctctgtcccc     480
cgaaggggaa cgctctatct ctagagttgt cagaggatgt caagacctgg taaggttctt     540
cgcgttgctt cgaattaaac cacatgctcc accgcttgtg cgggccccg tcaattcctt     600
tgagtttcag tcttgcgacc gtactcccca ggcggagtgc ttaatgcgtt agctgcagca     660
ctaaagggcg gaaccctct aacacttagc actcatcgtt tacggcgtgg actaccaggg     720
tatctaatcc tgtttgctcc ccacgctttc gcgcctcagc gtcagttaca gaccaaaaag     780
ccgccttcgc cactggtgtt cctccacatc tctacgcatt tcaccgctac acgtggaatt     840
ccgcttttct cttctgcact caagttcccc agtttccaat gaccctccac ggttgagccg     900
tgggctttca catcanactt aanaaaccgc ctgcgcgcgc tttacgccca ataattncng     960
ataacgcttg ncacctacgt attaccgcgg ctgctggcac gtanntagcc gnggntttct    1020
ggttaggtac ngtcnnggta caagcannta ctctnnactn nnnttncnta acananantt    1080
tacgacccga anncntcntc actcangcgc ntngctcnnn cagantntnn nnn           1133

<210> SEQ ID NO 3
<211> LENGTH: 1451
<212> TYPE: DNA
<213> ORGANISM: Bacillus megaterium
<220> FEATURE:
<221> NAME/KEY: misc_feature
<222> LOCATION: (852)..(852)
<223> OTHER INFORMATION: n is a, c, g, or t

<400> SEQUENCE: 3
ataatgcaag tcgagcgaac tgattagaag cttgcttcta tgacgttagc ggcggacggg      60
tgagtaacac gtgggcaacc tgcctgtaag actgggataa cttcgggaaa ccgaagctaa     120
taccggatag gatcttctcc ttcatgggag atgattgaaa gatggtttcg gctatcactt     180
acagatgggc ccgcggtgca ttagctagtt ggtgaggtaa cggctcacca aggcaacgat     240
gcatagccga cctgagaggg tgatcggcca cactgggact gagacacggc ccagactcct     300
acgggaggca gcagtaggga atcttccgca atggacgaaa gtctgacgga gcaacgccgc     360
gtgagtgatg aaggctttcg ggtcgtaaaa ctctgttgtt agggaagaac aagtacaaga     420
gtaactgctt gtaccttgac ggtacctaac cagaaagcca cggctaacta cgtgccagca     480
gccgcggtaa tacgtaggtg gcaagcgtta tccggaatta ttgggcgtaa agcgcgcgca     540
ggcggttct taagtctgat gtgaaagccc acggctcaac cgtggagggt cattggaaac     600
```

```
tggggaactt gagtgcagaa gagaaaagcg gaattccacg tgtagcggtg aaatgcgtag        660
agatgtggag gaacaccagt ggcgaaggcg gcttttggt ctgtaactga cgctgaggcg         720
cgaaagcgtg gggagcaaac aggattagat accctggtag tccacgccgt aaacgatgag        780
tgctaagtgt tagagggttt ccgcccttta gtgctgcagc taacgcatta agcactccgc        840
ctggggagta cnggtcgcaa gactgaaact caaaggaatt gacggggcc cgcacaagcg         900 gtggagcatg tggtttaatt cgaagcaacg cgaagaacct taccaggtct tgacatcctc        960
tgacaactct agagatagag cgttcccctt cggggacag agtgacaggt ggtgcatggt        1020
tgtcgtcagc tcgtgtcgtg agatgttggg ttaagtcccg caacgagcgc aacccttgat       1080
cttagttgcc agcattcagt tgggcactct aaggtgactg ccggtgacaa accggaggaa       1140
ggtggggatg acgtcaaatc atcatgcccc ttatgacctg gctacacac gtgctacaat        1200 ggatggtaca aagggctgca agaccgcgag gtcaagccaa tcccataaaa ccattctcag       1260
ttcggattgt aggctgcaac tcgcctacat gaagctggaa tcgctagtaa tcgcggatca       1320
gcatgccgcg gtgaatacgt tcccgggcct tgtacacacc gcccgtcaca ccacgagagt      1380
ttgtaacacc cgaagtcggt ggagtaaccg taaggagcta gccgcctaag gtgggacaga      1440
tgattggggt g                                                            1451
```

<210> SEQ ID NO 4
<211> LENGTH: 1212
<212> TYPE: DNA
<213> ORGANISM: Bacillus megaterium

<400> SEQUENCE: 4

```
gctatactgc aagtcgagcg aactgataga agcttgcttc tatgacgttg cggcggacgg         60
gtgagtaaca cgtgggcaac ctgcctgtaa gactgggata acttcgggaa accgaagcta       120
ataccggata ggatcttctc cttcatggga gatgattgaa agatggtttc ggctatcact       180
tacagatggg cccgcggtgc attagctagt tggtgaggta acggctcacc aaggccacga       240
tgcatagccg acctgagagg gtgatcggcc acactgggac tgagacacgg cccagactcc       300
tacgggaggc agcagtaggg aatcttccgc aatggacgaa agtctgacgg agcaacgccg       360
cgtgagtgat gaaggctttc gggtcgtaaa actctgttgt tagggaagaa caagtacaag       420
agtaactgct tgtaccttga cggtacctaa ccagaaagcc acggctaact acgtgccagc       480
agccgcggta atacgtaggt ggcaagcgtt atccggaatt attgggcgta aagcgcgcgc       540
aggcggtttc ttaagtctga tgtgaaagcc cacggctcaa ccgtgagggg tcattggaaa       600
ctggggaact tgagtgcaga agagaaaagc ggaattccac gtgtagcggt gaaatgcgta       660
gagatgtgga ggaacaccag tggcgaaggc ggcttttggg tctgtaactg acgctgaggc       720
gcgaaagcgt ggggagcaaa caggattaga taccctggta gtccacgccg taacgatgag       780
tgctaagtgt tagagggttt ccgcccttta gtgctgcagc taacgcatta agcactccgc       840
ctggggagta cggtcgcaag actgaaactc aaaggaattg acggggcccc gcacaagcgg       900
tggagcatgt ggtttaattc gaagcaacgc gaagaacctt accaggtctt gacatcctct       960
gacaactcta gagatagagc gttccccttc ggggacagag tgacaggtg gtgcatgggt       1020 tgtcgtcagc tcgtgtcgtg agatgttggg ttaagtcccg caacgagcgc aacccttga       1080 tcttagttgc cagcatttag tgggcactct aaggtgactg ccggtgacaa cgagaaggtg      1140
gggatgacgt cgaatcatca tgccccttak gacctggggc twcacamcgk tgcywacaak     1200
```

```
ggaattggtt ac                                                          1212
```

<210> SEQ ID NO 5
<211> LENGTH: 1089
<212> TYPE: DNA
<213> ORGANISM: Bacillus megaterium

<400> SEQUENCE: 5

```
tgttacgact tcaccccaat catctgtccc accttaggcg gctagctcct tacggttact      60
ccaccgactt cgggtgttac aaactctcgt ggtgtgacgg gcggtgtgta caaggcccgg     120
gaacgtattc accgcggcat gctgatccgc gattacyagc gattcctgct tcatgtaggc     180
kagttgcagc ctacaatccg aactgagaat ggttttatgg gattggcttg acctcgcggt     240
cttgcagccc tttgtaccat ccattgtagc acgtgtgtag cccaggtcat aaggggcatg     300
atgatttgac gtcatcccca ccttcctccg gtttgtcacc ggcagtcacc ttagagtgcc     360
caactaaatg ctggcaacta agatcaaggg ttgcgctcgt tgcgggactt aacccaacat     420
ctcacgacac gagctgacga cmaccatgca ccacctgtca ctctgtcccc cgaaggggaa     480
cgctctatct ctagagttgt cagaggatgt caagacctgg taaggttctt cgcgttgctt     540
cgaattaaac cacatgctcc accgcttgtg cgggccccccg tcaattcctt tgagtttcag     600
tcttgcgacc gtactcccca ggcggagtgc ttaatgcgtt agctgcagca ctaaagggcg     660
gaaaccctct aacacttagc actcatcgtt tacggcgtgg actaccaggg tatctaatcc     720
tgtttgctcc ccacgctttc gcgcctcagc gtcagttaca gaccaaaaag ccgccttcgc     780
cactggtgtt cctccacatc tctacgcatt tcaccgctac acgtggaaat ccgcttttct     840
cttctgcact caagttcccc agtttccaat gaccctccac ggttgagccg tgggctttca     900
catcagactt aagaaaccgc ctgcgcgcgc tttacgccca ataattcaga taacgctcgc     960
cacctacgta ttaccgcgct gctggcacgt agttagccgt ggctttctgg ttagtaccgt    1020
cagtacagca gtactctgta cttgttcttc ctaacaacag agtttacgac ccgaaagcct    1080
tcatcattc                                                             1089
```

<210> SEQ ID NO 6
<211> LENGTH: 1462
<212> TYPE: DNA
<213> ORGANISM: Bacillus megaterium

<400> SEQUENCE: 6

```
gctatactgc aagtcgagcg aactgataga agcttgcttc tatgacgttg cggcggacgg      60
gtgagtaaca cgtgggcaac ctgcctgtaa gactgggata acttcgggaa accgaagcta     120
ataccggata ggatcttctc cttcatggga gatgattgaa agatggtttc ggctatcact     180
tacagatggg cccgcggtgc attagctagt tggtgaggta acggctcacc aaggccacga     240
tgcatagccg acctgagagg gtgatcggcc acactgggac tgagacacgg cccagactcc     300
tacgggaggc agcagtaggg aatcttccgc aatggacgaa agtctgacgg agcaacgccg     360
cgtgagtgat gaaggctttc gggtcgtaaa actctgttgt tagggaagaa caagtacaag     420
agtaactgct tgtaccttga cggtacctaa ccagaaagcc acggctaact acgtgccagc     480
agccgcggta atacgtaggt ggcragcgtt atcyggaatt attgggcgta aagcgcgcgc     540
aggcggtttc ttaagtctga tgtgaaagcc cacggctcaa ccgtggaggg tcattggaaa     600
ctggggaact tgagtgcaga agagaaaagc ggawttccac gtgtagcggt gaaatgcgta     660
gagatgtgga ggaacaccag tggcgaaggc ggcttttttgg tctgtaactg acgctgaggc     720
```

```
gcgaaagcgt ggggagcaaa caggattaga taccctggta gtccacgccg taaacgatga      780
gtgctaagtg ttagagggtt tccgcccttt agtgctgcag ctaacgcatt aagcactccg      840
cctggggagt acggtcgcaa gactgaaact caaaggaatt gacggggggcc cgcacaagcg     900
gtggagcatg tggtttaatt cgaagcaacg cgaagaacct taccaggtct tgacatcctc      960
tgacaactct agagatagag cgttcccctt cggggggacag agtgacaggt ggtgcatggt     1020
kgtcgtcagc tcgtgtcgtg agatgttggg ttaagtcccg caacgagcgc aacccttgat     1080
cttagttgcc agcatttagt tgggcactct aaggtgactg ccggtgacaa accggaggaa     1140
ggtggggatg acgtcaaatc atcatgcccc ttatgacctg ggctacacac gtgctacaat     1200
ggatggtaca aagggctgca agaccgcgag gtcaagccaa tcccataaaa ccattctcag     1260
ttcggattgt aggctgcaac tmgcctacat gaagcaggaa tcgctrgtaa tcgcggatca     1320
gcatgccgcg gtgaatacgt tcccgggcct tgtacacacc gcccgtcaca ccacgagagt     1380
ttgtaacacc cgaagtcggt ggagtaaccg taaggagcta gccgcctaag gtgggacaga     1440
tgattggggt gaagtcgtaa ca                                              1462

<210> SEQ ID NO 7
<211> LENGTH: 1229
<212> TYPE: DNA
<213> ORGANISM: Bacillus megaterium

<400> SEQUENCE: 7
tgctataatg cagtcgagcg aactgattag aagcttgctt ctatgacgtt agcggcggac       60
gggtgagtaa cacgtgggca acctgcctgt aagactggga taacttcggg aaaccgaagc      120
taataccgga taggatcttc tccttcatgg gggatgattg aaagatggtt tcggctatca      180
cttacagatg ggcccgcggt gcattagcta gttggtgagg taacggctca ccaaggcmac      240
gatgcatagc cgacctgaga gggtgatcgg ccacactggg actgagacac ggcccagact      300
cctacgggag gcagcagtag ggaatcttcc gcaatggacg aaagtctgac ggagcaacgc      360
cgcgtgagtg atgaaggctt tcgggtcgta aaactctgtt gttagggaag aacaagtacr      420
agagtaactg cttgtacctt gacggtacct aaccagaaag ccacggctaa ctacgtgcca      480
gcagccgcgg taatacgtag gtggcaagcg ttatccggaa ttattgggcg taaagcgcgc      540
gcaggcggtt tcttaagtct gatgtgaaag cccacggctc aaccgtggag ggtcattgga     600
aactggggaa cttgagtgca gaagagaaaa gcggaattcc acgtgtagcg gtgaaatgcg      660
tagagatgtg gaggaacacc agtggcgaag gcggcttttt ggtctgtaac tgacgctgag      720
gcgcgaaagc gtggggagca acaggattta gataccctgg tagtccacgc cgtaaacgat      780
gagtgctaag tgttagaggg ttttccgccct ttagtgctgc agctaacgca ttaagcactc     840
cgcctgggga gtacggtcgc aagactgaaa ctcaaaggaa ttgacggggg cccgcacaag      900
cggtggagca tgtggtttaa ttcgaagcaa cgcgagaacc ttaccaggtc ttgacatcct      960
ctgacactct agagatagag cgttcccctt cggggggacag agtgacagtg tgcatggtgt     1020
cgtcagctcg tgtcgtgaga tgtgggtagt cccgcacgag cgcacctgat ctagtgcagc     1080
attagtggca ctctagtgac tgcgtgacac gaggaggtgg gatgacgtca tcatcatgcc     1140
cctatgactg ggctaccacg tgctacatgg atgtcaaggc tgcagaccga agtcagcaat     1200
cataaacatt ctcagtcgaa tgtaagtca                                       1229

<210> SEQ ID NO 8
```

<211> LENGTH: 1224
<212> TYPE: DNA
<213> ORGANISM: Bacillus megaterium

<400> SEQUENCE: 8

| | | | | | |
|---|---|---|---|---|---|
| cttgttcgac | ttcccccaat | catctgtccc | accttaggcg | gctagctcct | tacggttact | 60 |
| ccaccgactt | cgggtgttac | aaactctcgt | ggtgtgacgg | gcggtgtgta | caaggcccgg | 120 |
| gaacgtattc | accgcggcat | gctgatccgc | gattactagc | gattccagct | tcatgtaggc | 180 |
| gagttgcagc | ctacaatccg | aactgagaat | ggttttatgg | gattggcttg | acctcgcggt | 240 |
| cttgcagccc | tttgtaccat | ccattgtagc | acgtgtgtag | cccaggtcat | aagggggcatg | 300 |
| atgatttgac | gtcatcccca | ccttcctccg | gtttgtcacc | ggcagtcacc | ttagagtgcc | 360 |
| caactaaatg | ctggcaacta | agatcaaggg | ttgcgctcgt | tgcgggactt | aacccaacat | 420 |
| ctcacgacac | gagctgacga | caaccatgca | ccacctgtca | ctctgtcccc | gaaggggaa | 480 |
| cgctctatct | ctagagttgt | cagaggatgt | caagacctgg | taaggttctt | cgcgttgctt | 540 |
| cgaattaaac | cacatgctcc | accgcttgtg | cgggcccccg | tcaattcctt | tgagtttcag | 600 |
| tcttgcgacc | gtactcccca | ggcggagtgc | ttaatgcgtt | agctgcagca | ctaaagggcg | 660 |
| gaaaccctct | aacacttagc | actcatcgtt | tacgcgtgg | actaccaggg | tatctaatcc | 720 |
| tgtttgctcc | ccacgctttc | gcgcctcagc | gtcagttaca | gaccaaaaag | ccgccttcgc | 780 |
| cactggtgtt | cctccacatc | tctacgcatt | tcaccgctac | acgtggaatt | ccgcttttct | 840 |
| cttctgcact | caagttcccc | agtttccaat | gaccctccac | ggttgagccg | tggggctttc | 900 |
| acatcagact | taagaaaccg | cctgcgcgcg | ctttacgccc | aataattccc | ggataacgct | 960 |
| tgccacctac | gtattaccgc | ggctgctggc | acgtagttag | ccgtggcttt | ctggttaggt | 1020 |
| accgtcgagg | tacaagcagt | tactctcgta | cttgtcttcc | ctaacacaga | gttttacgac | 1080 |
| ccgaagctca | tcactcagcg | cgtgctcgtc | gacttcgtca | ttgcgagatc | cctactgctg | 1140 |
| cttccgtagg | agtctggacc | tgtctcagtc | aggtgtgacg | gatcaccctc | ttcagtcgcc | 1200 |
| tatgtgccac | tctcgtgggt | cccg | | | | 1224 |

<210> SEQ ID NO 9
<211> LENGTH: 1466
<212> TYPE: DNA
<213> ORGANISM: Bacillus megaterium

<400> SEQUENCE: 9

| | | | | | |
|---|---|---|---|---|---|
| tgctataatg | cagtcgagcg | aactgattag | aagcttgctt | ctatgacgtt | agcggcggac | 60 |
| gggtgagtaa | cacgtgggca | acctgcctgt | aagactggga | taacttcggg | aaaccgaagc | 120 |
| taataccgga | taggatcttc | tccttcatgg | gggatgattg | aaagatggtt | tcggctatca | 180 |
| cttacagatg | ggcccgcggt | gcattagcta | gttggtgagg | taacggctca | ccaaggcmac | 240 |
| gatgcatagc | cgacctgaga | gggtgatcgg | ccacactggg | actgagacac | ggcccagact | 300 |
| cctacgggag | gcagcagtag | ggaatcttcc | gcaatggacg | aaagtctgac | ggagcaacgc | 360 |
| cgcgtgagtg | atgaaggctt | tcgggtcgta | aaactctgtt | gttagggaag | aacaagtacg | 420 |
| agagtaactg | cttgtaccty | gacggtacct | aaccagaaag | ccacggctaa | ctacgtgcca | 480 |
| gcagccgcgg | taatacgtag | gtggcaagcg | ttatccggga | attattgggc | gtaaagcgcg | 540 |
| cgcaggcggt | tcttaagtc | tgatgtgaaa | gcccacggc | tcaaccgtgg | agggtcattg | 600 |
| gaaactggga | aacttgagtg | cagaagagaa | aagcggaatt | ccacgtgtag | cggtgaaatg | 660 |
| cgtagagatg | tggaggaaca | ccagtggcga | aggcggcttt | ttggtctgta | actgacgctg | 720 |

```
aggcgcgaaa gcgtggggag caaacaggat tagataccct ggtagtccac gccgtaaacg        780
atgagtgcta agtgttagag ggtttccgcc ctttagtgct gcagctaacg cattaagcac        840
tccgcctggg gagtacggtc gcaagactga aactcaaagg aattgacggg ggcccgcaca        900
agcggtggag catgtggttt aattcgaagc aacgcgaaga accttaccag gtcttgacat        960
cctctgacaa ctctagagat agagcgttcc ccttcggggg acagagtgac aggtggtgca       1020
tggttgtcgt cagctcgtgt cgtgagatgt tgggttaagt cccgcaacga gcgcaaccct       1080
tgatcttagt tgccagcatt tagttgggca ctctaaggtg actgccggtg acaaaccgga       1140
ggaaggtggg gatgacgtca atcatcatg cccttatga cctgggctac acacgtgcta        1200
caatggatgg tacaaagggc tgcaagaccg cgaggtcaag ccaatcccat aaaaccattc       1260
tcagttcgga ttgtaggctg caactcgcct acatgaagct ggaatcgcta gtaatcgcgg       1320
atcagcatgc cgcggtgaat acgttccgg gccttgtaca caccgcccgt cacaccacga       1380
gagtttgtaa cacccgaagt cggtggagta accgtaagga gctagccgcc taaggtggga      1440
cagatgattg ggggaagtcg aacaag                                             1466
```

<210> SEQ ID NO 10
<211> LENGTH: 20
<212> TYPE: DNA
<213> ORGANISM: Artificial Sequence
<220> FEATURE:
<223> OTHER INFORMATION: 27F primer - synthesized sequence made in
      laboratory

<400> SEQUENCE: 10
agagtttgat cmtggctcag                                                      20

<210> SEQ ID NO 11
<211> LENGTH: 17
<212> TYPE: DNA
<213> ORGANISM: Artificial Sequence
<220> FEATURE:
<223> OTHER INFORMATION: 1525R - Synthesized sequence made in laboratory

<400> SEQUENCE: 11
aaggaggtgw tccarcc                                                         17

<210> SEQ ID NO 12
<211> LENGTH: 21
<212> TYPE: DNA
<213> ORGANISM: Artificial Sequence
<220> FEATURE:
<223> OTHER INFORMATION: recAf Synthesized sequence made in laboratory

<400> SEQUENCE: 12
gatcgtcarg cagscytwga t                                                    21

<210> SEQ ID NO 13
<211> LENGTH: 20
<212> TYPE: DNA
<213> ORGANISM: Artificial Sequence
<220> FEATURE:
<223> OTHER INFORMATION: recAr - synthesized sequence made in laboratory

<400> SEQUENCE: 13
ttwccracca taacsccrac                                                      20

<210> SEQ ID NO 14
<211> LENGTH: 562

<212> TYPE: DNA
<213> ORGANISM: Bacillus megaterium
<220> FEATURE:
<221> NAME/KEY: misc_feature
<222> LOCATION: (551)..(551)
<223> OTHER INFORMATION: n is a, c, g, or t

<400> SEQUENCE: 14

```
tgaaagcatt tggtaaggtt caattatgaa attaggtgaa caaacggaaa aaagaatttc    60
tacaattcca agtggttcat tggcgttaga tatagcctta ggtgtaggtg atatccacg    120
tggacgtgta gttgaagtat atggtccaga aagctcaggt aaaacaacag ttgctcttca   180
tgcgattgca gaagttcaac agcagggcgg acaggctgca tttatcgatg cggagcacgc   240
gttagatcct gtatatgctc aaaaattagg tgtgaatatt gatgagctat tattatctca   300
gcctgatacg ggagaacaag ctttagaaat cgctgaagct ttagttcgaa gcggtgcagt   360
agatattatc gttgttgact cagtagcagc attagtgcca aaagcggaaa ttgaaggaga   420
aatgggagac tctcacgtgg gtctacaagc tcgtttaatg tctcaagcat tgcgtaaact   480
atctggagct atcaataagt ctaaaacaat cgctatcttt attaaccaaa ttcgtgaaaa   540
agtcggcgtt ngggtcggaa aa                                           562
```

<210> SEQ ID NO 15
<211> LENGTH: 558
<212> TYPE: DNA
<213> ORGANISM: Bacillus megaterium

<400> SEQUENCE: 15

```
gwagcgattg ttttagactt attgatagct ccagatagtt tacgcaatgc ttgagacatt    60
aaackagctt gtagacccac gtgagagtct cccatttctc cttcaatttc gcttttggc    120
actaatgctg ctactgagtc aacaacgata atatctactg caccgcttcg aactaaagct   180
tcagcgattt ctaaagcttg ttctcccgta tcaggctgag ataataatag ctcatcaata   240
ttcacaccta atttttgagc atatacagga tctaacgcgt gctccgcatc gataaatgca   300
gcctgtccgc cctgctgttg aacttctgca atcgcatgaa gagcaactgt tgttttacct   360
gagctttctg gaccatatac ttcaactaca cgtccacgtg gatatccacc tacacctaag   420
gctatatcta cgccaatgaa ccacttggaa attgtagaaa ttcttttttc cgtttgttca   480
cctaatttca taattgaacc tttaccaaat tgcttttcaa tttgtttaaa agccatatcw   540
aagcctgcww wgacgatc                                                 558
```

<210> SEQ ID NO 16
<211> LENGTH: 500
<212> TYPE: DNA
<213> ORGANISM: Bacillus megaterium

<400> SEQUENCE: 16

```
aaggttcaat tatgaaatta ggtgaacaaa cggaaaaaag aatttctaca attccaagtg    60
gttcattggc gttagatata gccttaggtg taggtggata tccacgtgga cgtgtagttg   120
aagtatatgg tccagaaagc tcaggtaaaa caacagttgc tcttcatgcg attgcagaag   180
ttcaacagca gggcggacag gctgcattta tcgatgcgga gcacgcgtta gatcctgtat   240
atgctcaaaa attaggtgtg aatattgatg agctattatt atctcagcct gatacgggag   300
aacaagcttt agaaatcgct gaagcttag ttcgaagcgg tgcagtagat attatcgttg   360
ttgactcagt agcagcatta gtgccaaaag cggaaattga aggagaaatg ggagactctc   420
```

```
acgtgggtct acaagctcgt ttaatgtctc aagcattgcg taaactatct ggagctatca    480
ataagtctaa aacaatcgct                                                500

<210> SEQ ID NO 17
<211> LENGTH: 564
<212> TYPE: DNA
<213> ORGANISM: Bacillus megaterium
<220> FEATURE:
<221> NAME/KEY: misc_feature
<222> LOCATION: (552)..(552)
<223> OTHER INFORMATION: n is a, c, g, or t

<400> SEQUENCE: 17
ttgaagcatt tggtaaaggt tcaattatga aattaggtga acaaacggaa aaagaatttt     60
ctacaattcc aagtggttca ttagcgttag atatagcttt aggtgtaggt ggatatccac    120
gtggacgcgt agttgaagta tatggtccag aaagctcagg taaaacaaca gttgctcttc    180
atgcgattgc agaagttcaa cagcagggcg gacaggctgc atttatcgat gcggagcacg    240
cgttagatcc tgtatatgct caaaaattag gtgtgaatat tgatgagcta ttattatctc    300
agcctgatac gggagaacaa gctttagaaa tcgctgaagc tttagttcga agcggtgcag    360
tagatattat cgttgttgac tcagtagcag cattagtgcc aaaagcggaa attgaaggag    420
aaatgggaga ctctcacgtg ggtctacaag ctcgtttaat gtctcaagca ttgcgtaaac    480
tatctggagc tatcaacaag tctaaaacaa tcgctatctt tattaaccaa attcgtgaaa    540
aagtcggcgt tngggttcgg aaaa                                           564

<210> SEQ ID NO 18
<211> LENGTH: 570
<212> TYPE: DNA
<213> ORGANISM: Bacillus megaterium

<400> SEQUENCE: 18
ggtataaaga taggcgattg ttttagactt gttgatagct ccagatagtt tacgcaatgc     60
ttgagacatt aaacgagctt gtagacccac gtgagagtct cccatttctc cttcaatttc    120
cgcttttggc actaatgctg ctactgagtc aacaacgata atatctactg caccgcttcg    180
aactaaagct tcagcgattt ctaaagcttg ttctcccgta tcaggctgag ataataatag    240
ctcatcaata ttcacaccta atttttgagc atatacagga tctaacgcgt gctccgcatc    300
gataaatgca gcctgtccgc cctgctgttg aacttctgca atcgcatgaa gagcaactgt    360
tgttttacct gagctttctg gaccatatac ttcaactacg cgtccacgtg gatatccacc    420
tacacctaaa gctatatcta acgctaatga accacttgga attgtagaaa ttcttttttc    480
cgtttgttca cctaatttca taattgaacc tttaccaaat tgcttttcaa tttgttttaa    540
agccatatcw aagcctaaww rgacgatcya                                     570

<210> SEQ ID NO 19
<211> LENGTH: 498
<212> TYPE: DNA
<213> ORGANISM: Bacillus megaterium

<400> SEQUENCE: 19
aaggttcaat tatgaaatta ggtgaacaaa cggaaaaaag aatttctaca attccaagtg     60
gttcattagc gttagatata gcttaggtg taggtggata tccacgtgga cgcgtagttg    120
aagtatatgg tccagaaagc tcaggtaaaa caacagttgc tcttcatgcg attgcagaag    180
ttcaacagca gggcggacag gctgcattta tcgatgcgga gcacgcgtta gatcctgtat    240
```

```
atgctcaaaa attaggtgtg aatattgatg agctattatt atctcagcct gatacgggag    300
aacaagcttt agaaatcgct gaagctttag ttcgaagcgg tgcagtagat attatcgttg    360
ttgactcagt agcagcatta gtgccaaaag cggaaattga aggagaaatg ggagactctc    420
acgtgggtct acaagctcgt ttaatgtctc aagcattgcg taaactatct ggagctatca    480
acaagtctaa aacaatcg                                                  498
```

<210> SEQ ID NO 20
<211> LENGTH: 561
<212> TYPE: DNA
<213> ORGANISM: Bacillus megaterium
<220> FEATURE:
<221> NAME/KEY: misc_feature
<222> LOCATION: (550)..(550)
<223> OTHER INFORMATION: n is a, c, g, or t

<400> SEQUENCE: 20

```
gaaagcattt ggtaaggttc aattatgaaa ttaggtgaac aaacggaaaa aagaatttct    60
acaattccaa gtggttcatt agcgttagat atagccttag gtgtaggtgg atatccacgt   120
ggacgtgtag ttgaagtata tggtccagaa agctcaggta aaacaacagt tgctcttcat   180
gcgattgcag aagttcaaca gcagggcgga caggctgcat ttatcgatgc ggagcacgcg   240
ttagatcctg tatatgctca aaaattaggt gtgaatattg atgagctatt attatctcag   300
cctgatacgg gagaacaagc tttagaaatc gctgaagctt tagttcgaag cggtgcagta   360
gatattatcg ttgttgactc agtagcagca ttagtgccaa aagcggaaat tgaaggagaa   420
atgggagact ctcacgtggg tctacaagct cgtttaatgt ctcaagcatt gcgtaaacta   480
tctggagcta tcaataagtc taaaacaatc gctatcttta ttaaccaaat tcgtgaaaaa   540
gtcggcgttn gggtcggaaa a                                             561
```

<210> SEQ ID NO 21
<211> LENGTH: 557
<212> TYPE: DNA
<213> ORGANISM: Bacillus megaterium

<400> SEQUENCE: 21

```
agcgattgtt ttagacttat tgatagctcc agatagttta cgcaatgctt gagacattaa    60
acgagcttgt agacccacgt gagagtctcc catttctcct tcaatttccg cttttggcac   120
taatgctgct actgagtcaa caacgataat atctactgca ccgcttcgaa ctaaagcttc   180
agcgatttct aaagcttgtt ctcccgtatc aggctgagat aataatagct catcaatatt   240
cacacctaat ttttgagcat atacaggatc taacgcgtgc tccgcatcga taaatgcagc   300
ctgtccgccc tgctgttgaa cttctgcaat cgcatgaaga gcaactgttg ttttacctga   360
gctttctgga ccatatactt caactacacg tccacgtgga tatccaccta cacctaaggc   420
tatatctaac gctaatgaac cacttggaat tgtagaaatt cttttttccg tttgttcacc   480
taatttcata attgaacctt taccaaattg cttttcaatt tgtttttaaag ccatatcaaa   540 gcctgctaaa cratcaa                                                  557
```

<210> SEQ ID NO 22
<211> LENGTH: 500
<212> TYPE: DNA
<213> ORGANISM: Bacillus megaterium

<400> SEQUENCE: 22

-continued

```
aaggttcaat tatgaaatta ggtgaacaaa cggaaaaaag aatttctaca attccaagtg      60
gttcattagc gttagatata gccttaggtg taggtggata tccacgtgga cgtgtagttg     120
aagtatatgg tccagaaagc tcaggtaaaa caacagttgc tcttcatgcg attgcagaag    180
ttcaacagca gggcggacag gctgcattta tcgatgcgga gcacgcgtta gatcctgtat    240
atgctcaaaa attaggtgtg aatattgatg agctattatt atctcagcct gatacgggag    300
aacaagcttt agaaatcgct gaagctttag ttcgaagcgg tgcagtagat attatcgttg    360
ttgactcagt agcagcatta gtgccaaaag cggaaattga aggagaaatg ggagactctc    420
acgtgggtct acaagctcgt ttaatgtctc aagcattgcg taaactatct ggagctatca    480
ataagtctaa aacaatcgct                                                500
```

BACILLUS MEGATERIUM BIOACTIVE COMPOSITIONS AND METABOLITES

CROSS-REFERENCE TO RELATED APPLICATIONS

This application claims the benefit of U.S. Provisional Patent Application No. 61/683,154, filed Aug. 14, 2012; the disclosure of which is incorporated by reference in its entirety for all purposes.

SEQUENE LISTING

The instant application contains a Sequence Listings which has been submitted in ASCII format via EFS-WEB and is hereby incorprated by refence in its entirety. Said ASCII copy, is named MOI-42033-US-SEQ. txt an dis 29 kB in size.

TECHNICAL FIELD

The present disclosure is in the field of bioactive compositions having pesticidal activity and methods for their use in controlling plant pests. In particular, such compositions comprise a Bacillus strain and/or its metabolites, more particularly strains of Bacillus megaterium and their metabolites.

BACKGROUND

Natural products are substances produced by microbes, plants, and other organisms. Microbial natural products offer an abundant source of chemical diversity, and there is a long history of utilizing natural products for pharmaceutical purposes. Despite the emphasis on natural products for human therapeutics, where more than 50% are derived from natural products, only 11% of pesticides are derived from natural sources. Nevertheless, natural product pesticides have a potential to play an important role in controlling pests in both conventional and organic farms. Secondary metabolites produced by microbes (bacteria, actinomycetes and fungi) provide novel chemical compounds which can be used either alone or in combination with known compounds to effectively control insect pests and to reduce the risk for resistance development. There are several well-known examples of microbial natural products that are successful as agricultural insecticides (Thompson et al., 2000; Arena et al., 1995; Krieg et al. 1983).

The development of a microbial pesticide starts with the isolation of a microbe in a pure culture. It then proceeds with efficacy and spectrum screening using in vitro, in vivo or pilot scale trials in a greenhouse and in the field. At the same time, active compounds produced by the microbe are isolated and identified. For the commercialization of a microbial pesticide, the microbe has to be economically produced by fermentation at an industrial scale, and formulated with a biocompatible carrier and approved additives to increase efficacy and to maximize the ease of application.

Uses of *Bacillus Megaterium* and Products Produced Therefrom

*Bacillus megaterium* is a Gram-positive bacterium that grows in simple media and on more than 62 out of 95 carbon sources, such as tricarboxylic acid cycle intermediates (e.g., formate and acetate), and forms spores mainly under aerobic conditions (see, for example, Vary, 2007). It has been found in a variety of habitats, such as soil, seawater, sediment, rice paddies, honey, fish, and dried food.

*Bacillus megaterium* has been found to have a number of different uses. Specifically, it produces a variety of industrial enzymes such as penicillin acylase, various amylases, and glucose dehydrogenase (reviewed in, Vary, 2007). Additionally, a fermentation of *B. megaterium* ATCC 19213 grown to stationary phase was found to produce N-Deoxyschizokinen, a siderophore, which was identified as 4-[(3(acetylhydroxyamino) propyl) amino]-2-[2-[(3-(acetylamino) propyl) amino]-2-oxoethyl]-2-hydroxy-4-oxo-butanoic acid (Hu X and Boyer G. L, 1995). Schizokinen, a citrate-containing dihydroxamate, a siderophore has been produced by *B. megaterium* and *Anabaena* sp (Plowman J. E. et al 1984). The involvement of the citrate α-hydroxycarboxylate moiety in iron chelation was investigated by comparing the iron binding behavior of schizokinen with that of acetylschizokinen, a derivative in which the citrate hydroxyl group was modified by acetylation.

Another set of uses for products derived from *Bacillus megaterium* has been medicinal uses. BMG 59-R2, a peptide antibiotic, has been reported from *B. megaterium* (FERM-p 6177). The compound also inhibits alkaline phosphatase and tumour growth (Japan. Pat., 83 164 561. (1983)). Fermentation culture of *B. megaterium* in the presence of ansatrienin produces T23V and T23VI (Damberg, M. et al 1982). These compounds belong to the class of macrolides antibiotics, which also exhibit antitumor activity. A nucleoside named oxetanocin was isolated from *B. megaterium* NK84-0218 and the structure was determined to be 9-[(2R,3R,4S)-3,4-bis(hydroxymethyl)-2-oxetanyl]adenine by X-ray crystallographic analysis (Shimada N. et al., 1986). Oxetanocin showed activity against herpes simplex virus-II (DNA virus) at 5.8 pg/well (50% inhibition of cytopathic effect), while the cytotoxicity against Vero cells was 132.6 µg/well (50% inhibition of cell growth). Later, the derivatives of oxetanocin such as oxetanocins H, X, G and 2-aminooxetanocin A (Shimada N. et al., 1987) are isolated from the same strain which showed antiviral activities against herpes simplex virus type-II (HSV-II) and antiviral activities against human immunodeficiency virus. *B. megaterium* IFO 12108 (Nakahama, K. et al., 1981) was used for the microbial transformation of anamtiocin, an antitumor antibiotic produced by *Nocardia* sp. C-15003 (N-1). Ansamitocin P-3 was converted into 15-hydroxyansamitocin P-3 (PHO-3), and 15-epi-15-hydroxyansamitocin P-3 (epi-PHO-3), by using *B. megaterium* (Izawa M. et al., 1981). The microbial conversion product of P-3, has greater antitumor activities against P 388 and L 1210 than the substrate P-3.

Various isolates of *Bacillus megaterium* have been used as insecticides, bactericides, fungicides and nematicides (see, for example, Aksoy, H. M. 2008; U.S. Pat. Nos. 6,599,503, 7,906,131, 7,935,360). Some of these *B. megaterium* isolates have been used in combination with other bacteria to treat sludge and wastes such as *Artemisia annua* residue, flue dust, bran powder, feces of livestock and poultry, peat, and crop straw (see, for example, U.S. Pat. No. 7,279,104).

SUMMARY

Provided is a *B. megaterium* having the following characteristics:
(A) pesticidal activity;
(B) produces a pesticidal compound having the following properties: (1) has a molecular weight of about 140-185 as determined by Liquid Chromatography/Mass Spectroscopy (LC/MS); (2) has $^1$H NMR values of δ 7.28 (2H), 7.19 (2H), 7.17, 2.67, 2.31, 1.92 and has $^{13}$C NMR values of 177.5, 142.9, 129.5, 129.5, 129.4, 129.4, 126.9, 36.1, 34.4, 28.1 (3) has a High Pressure Liquid Chromatography (HPLC) retention time of about 8-18 minutes, on a reversed phase C-18

HPLC (Phenomenex, Luna 5μ C18(2) 100 A, 100×4.60 mm) column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm.;

(C) is non-pathogenic to vertebrate animals; and (D) is susceptible to tetracycline, erythromycin, streptomycin, penicillin, ampicillin, Oxytetracycline, Chloramphenicol, Ciprofloxacin, Gentamicin, Piperacillin, Imipenem and Sulphamethoxazole-Trimethoprim.

Also provided is a supernatant, cell fraction, filtrate, extract, compound or metabolite derived from a culture of *B. megaterium*.

Furthermore, the *Bacillus megaterium* sp. may have a 16S rRNA gene sequence comprising at least one of:

(A) a forward sequence having at least 99% identity and more particularly at least 99.5% identity to the sequence set forth in SEQ ID NO:1, a reverse sequence having at least 99% identity to the sequence set forth in SEQ ID NO:2 and at least 99% identity to the consensus sequence set forth in SEQ ID NO: 3;

(B) a forward sequence having at least 99% identity and more particularly at least 99.5% identity to the sequence set forth in SEQ ID NO:4, a reverse sequence having at least 99% identity to the sequence set forth in SEQ ID NO:5 and at least 99% identity to the consensus sequence set forth in SEQ ID NO: 6;

(C) a forward sequence having at least 99% identity and more particularly at least 99.5% identity to the sequence set forth in SEQ ID NO:7, a reverse sequence having at least 99% identity to the sequence set forth in SEQ ID NO:8 and at least 99% identity to the consensus sequence set forth in SEQ ID NO: 9.

Additionally, the *Bacillus megaterium* sp. may have a recA gene sequence comprising at least one of:

(A) a forward sequence having at least 99% identity and more particularly at least 99.5% identity to the sequence set forth in SEQ ID NO:14, a reverse sequence having at least 99% identity and more particularly at least 99.5% identity to the sequence set forth in SEQ ID NO:15 and at least 99% identity and more particularly at least 99.5% identity to the consensus sequence set forth in SEQ ID NO: 16;

(B) a forward sequence having at least 99% identity and more particularly at least 99.5% identity to the sequence set forth in SEQ ID NO:17, a reverse sequence having at least 99% identity and more particularly at least 99.5% identity to the sequence set forth in SEQ ID NO:18 and at least 99% identity and more particularly at least 99.5% identity to the consensus sequence set forth in SEQ ID NO: 19;

(C) a forward sequence having at least 99% identity and more particularly at least 99.5% identity to the sequence set forth in SEQ ID NO:20, a reverse sequence having at least 99% identity to the sequence set forth in SEQ ID NO:21 and at least 99% identity and more particularly at least 99.5% identity to the consensus sequence set forth in SEQ ID NO: 22.

In particular, the *Bacillus* is a *B. megaterium* strain having the identifying characteristics of *B. megaterium* strain H491 (NRRL Accession No. B-50769), *Bacillus megaterium* strain M018 (NRRL Accession No. B-50770) and *Bacillus megaterium* strain J142 (NRRL Accession No. B-50771), or a strain derived from one of said strains (e.g., a mutant strain). Therefore, in a related aspect, said *B. megaterium* is provided. Also provided is a substantially pure culture, or whole cell broth comprising said microorganism or cell fraction, supernatant, filtrate, extract, compound or metabolite derived therefrom.

The compound used in the methods and compositions and combinations may be a compound that (A) has pesticidal activity;

(B) has a molecular weight of about 140-185 as determined by Liquid Chromatography/Mass Spectroscopy (LC/MS) and (C) has a High Pressure Liquid Chromatography (HPLC) retention time of about 8-18 minutes on a reversed phase C-18 HPLC column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm and (D) is optionally obtainable from a *B. megaterium*. The compound in one embodiment may be a polyketide.

In a particular embodiment, the compound may be derived from *B. megaterium* and has a monosubstituted aromatic polyketide structure comprising at least one acid moiety, at least one 6 membered aromatic ring and at least three methylene group; a molecular weight from 140 to about 185 in the core structure; at least 8 carbons and at least 2 oxygens.

In one specific embodiment, the compound (A) is obtainable from a *B. megaterium*;

(B) is toxic to a pest;

(C) has a molecular weight of about 140-185 and more particularly, 164 as determined by Liquid Chromatography/Mass Spectroscopy (LC/MS);

(D) has $^1H$ NMR values of δ 7.28 (2H), 7.19 (2H), 7.17, 2.67, 2.31, 1.92 and has $^{13}C$ NMR values of 177.5, 142.9, 129.5, 129.5, 129.4, 129.4, 126.9, 36.1, 34.4, 28.1

(E) has an High Pressure Liquid Chromatography (HPLC) retention time of about 8-18 minutes, more specifically about 12 minutes and even more specifically about 12.16 min on a reversed phase C-18 HPLC (Phenomenex, Luna 5μ C18(2) 100 A, 100×4.60 mm) column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm.

In a more particular embodiment, provided are compounds including but not limited to:

(A) a compound having the structure ##STR001##

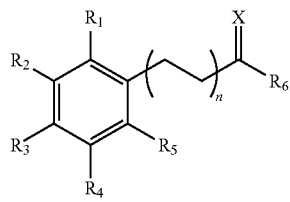

STR001## or a pesticidally acceptable salt or stereoisomers thereof, wherein n is 0, 1, 2, 3, 4, 5, 6, 7, 8 or 9; X is O, NH, NR or S; R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido or carboxy; $R_1$, $R_2$, $R_3$, $R_4$, $R_5$, $R_6$ are each independently H, hydroxyl, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(B) a compound having the structure ##STR001a##

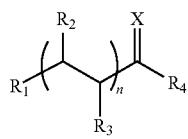

STR001a## or a pesticidally acceptable salt or stereoisomers thereof, wherein X is O, NH, NR or S; R is lower chain alkyl containing 1, 2, 3, 4, 5, 6, 7, 8 or 9 alkyl moieties, aryl or arylalkyl moiety, substituted lower alkyl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido or carboxy; n is 0, 1, 2, 3, 4, 5, 6, 7, 8 or 9; $R_1$, $R_2$, $R_3$, $R_4$ are each independently H, hydroxyl, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

(C) a compound having the structure ##STR001b##

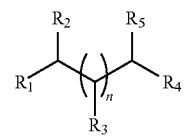

STR001b## or a pesticidally acceptable salt or stereoisomers thereof, wherein n is 0, 1, 2, 3, 4, 5, 6, 7, 8 or 9; $R_1$, $R_2$, $R_3$, $R_4$, $R_5$ are each independently H, hydroxyl, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

In a more particular embodiment, the compound is the aromatic polyketide, 4-phenylbutanoic acid (1).

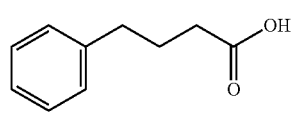

4-Phenylbutanoic acid

These compounds may be obtained by (A) culturing a *B. megaterium* in a culture medium, to obtain a *B. megaterium* whole-cell broth, under conditions sufficient to produce said compound(s), and (B) isolating said compound(s) produced in (A) from the whole cell broth of (A).

In particular, the compound in step (B) may be isolated by (i) applying the whole cell broth to at least one of an ion exchange column, a size exclusion column or a reversed phase HPLC column to obtain column fractions; (ii) assaying the column fractions for pesticidal activity and (iii) concentrating column fractions of (ii) to obtain the isolated compound. Alternatively, said compound(s) can be produced by chemical synthesis and the product(s) can be used either as a pure compound or as a crude product.

In additional embodiments, compositions and methods for modulating plant growth and in particular, promoting plant growth and/or modulating seed germination and particularly promoting seed germination are provided. For example, culture medium obtained after growth of the *B. megaterium* strains disclosed herein, also denoted whole cell broth (WCB), can be applied to plants, seeds and/or their growth substrate (e.g., soil) to promote the growth of the seeds and plants or germination of the seeds of the plant. Alternatively, plants, seeds and/or their growth substrate (e.g., soil) can be inoculated with any one or combination of the *B. megaterium* strains disclosed herein for the purpose of promoting growth of the plant. In further embodiments, a substantially pure culture or cell broth comprising *B. megaterium* or a supernatant, cell fraction, filtrate, extract, compound and/or metabolite derived therefrom can be used in methods for plant growth promotion or seed germination.

In additional embodiments, any of the compounds disclosed herein can be used in methods for promoting the growth of plants; for example, a compound that:

(a) has a molecular weight of about 140-185 and more particularly, 164 as determined by Liquid Chromatography/Mass Spectroscopy (LC/MS);

(b) has $^1$H NMR values of δ 7.28 (2H), 7.19 (2H), 7.17, 2.67, 2.31, 1.92 and has $^{13}$C NMR values of 177.5, 142.9, 129.5, 129.5, 129.4, 129.4, 126.9, 36.1, 34.4, 28.1; and (c) has an High Pressure Liquid Chromatography (HPLC) retention time of about 8-18 minutes, more specifically about 12 minutes and even more specifically about 12.16 min on a reversed phase C-18 HPLC (Phenomenex, Luna 5/µ C18(2) 100 A, 100×4.60 mm) column using a water:acetonitrile ($CH_3CN$) gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection at 210 nm.

Additional compounds useful in the disclosed methods and compositions for promoting plant growth include those identified above as STR001, STR001a STR001b and 4-phenylbutanoic acid (Compound 1).

Further provided is a pesticidal combination which may be synergistic to at least one pest comprising as active components: (a) a substantially pure culture or cell broth comprising *B. megaterium* or a supernatant, cell fraction, filtrate, extract, compound and/or metabolite derived therefrom and (b) another pesticidal substance, wherein (a) and (b) may be present in synergistic amounts. The pest, in a particular embodiment, may be an insect pest, but may also include, but is not limited to, a nematode, plant fungus, plant virus and plant bacteria and weeds. Further, the combination may be a composition. The pesticidal substance may be (a) derived from a microorganism; (b) a natural product and/or (c) a chemical pesticide and in particular a chemical nematicide.

In particular, the combination may comprise a whole microorganism, supernatant, filtrate and/or extract of *B. megaterium* and a pesticidal substance derived from a microorganism including but not limited to *Bacillus* sp. (e.g., *Bacillus thuringiensis* or *Bacillus thuringiensis kurstaki*) and spinosad. Alternatively, the combination may comprise a supernatant, filtrate and/or extract of *B. megaterium* and a pesticidal substance derived from a natural product such as pyrethrum. Alternatively, the combination may comprise a supernatant, filtrate and/or extract of *B. megaterium* and a pesticidal substance which is a chemical pesticide, particularly, an insecticide, where the insecticide includes but is not limited to pyrethrins, spirotetramet and organochlorines.

In a related aspect, provided herein is a method for modulating, in particular, synergistically modulating infestation of at least one pest or pest species in or around a plant comprising applying to a plant and/or seeds thereof and/or substrate for growing said plant the combinations set forth above with an amount of the combination effective to modulate infestation of said pest or pest species. Also provided herein are isolated compounds obtainable or derived from *B. megaterium* or alternatively, organisms capable of producing these compounds that can be used to control various pests, and/or also particularly, nematicidal pests.

Further provided is the use of
(a) a compound which:
(1) has a molecular weight of about 140-185 as determined by Liquid Chromatography/Mass Spectroscopy (LC/MS);
(2) has $^1$H NMR values of δ 7.28 (2H), 7.19 (2H), 7.17, 2.67, 2.31, 1.92 and has $^{13}$C NMR values of 177.5, 142.9, 129.5, 129.5, 129.4, 129.4, 126.9, 36.1, 34.4, 28.1;
(3) has an High Pressure Liquid Chromatography (HPLC) retention time of about 8-18 minutes, on a reversed phase C-18 HPLC (Phenomenex, Luna 5μ C18(2) 100 A, 100×4.60 mm) column using a water:acetonitrile ($CH_3CN$) with a gradient solvent system (0-20 min; 90-0% aqueous $CH_3CN$, 20-24 min; 100% $CH_3CN$, 24-27 min; 0-90% aqueous $CH_3CN$, 27-30 min; 90% aqueous $CH_3CN$) at 0.5 mL/min flow rate and UV detection of 210 nm.;
(4) has pesticidal properties; and
(b) optionally another substance, wherein said substance is a pesticide, effective to modulate pest infestation;
to formulate a pesticidal composition and/or modulate the infestation of one or more pests.

DETAILED DESCRIPTION

Figure 1:
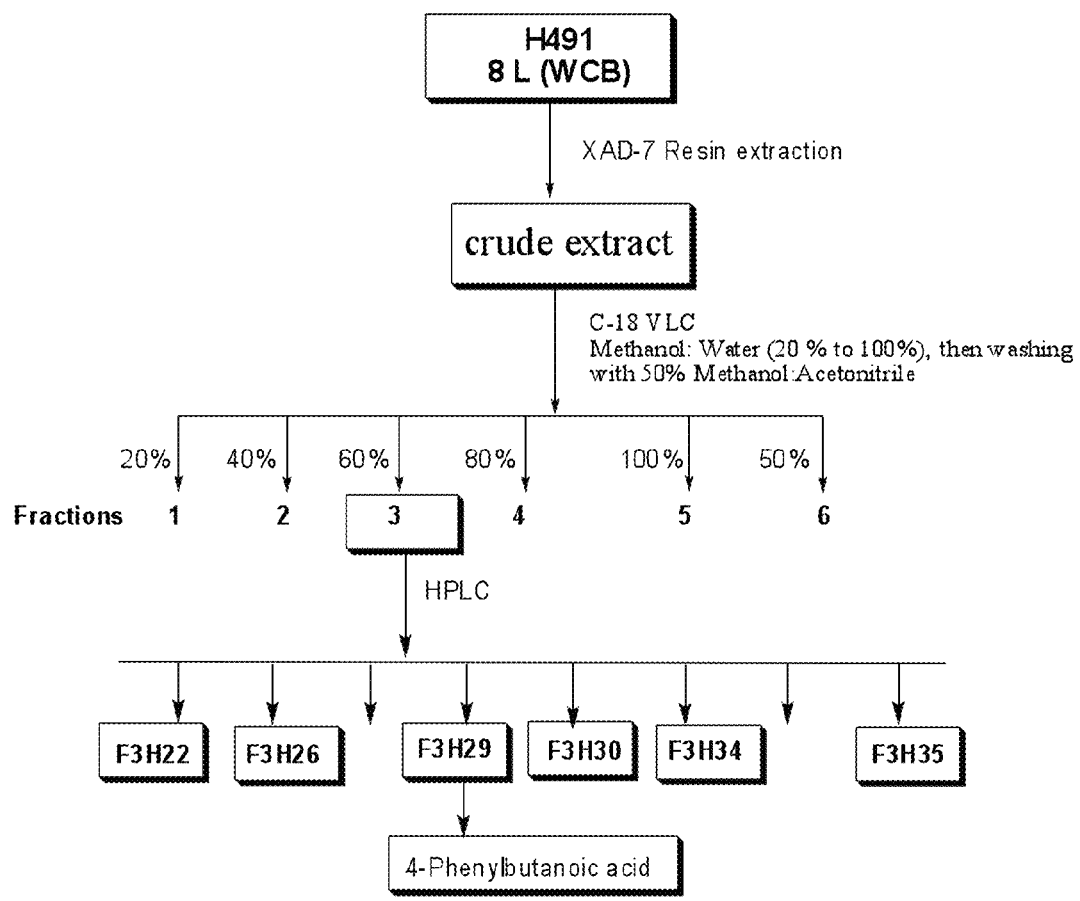
FIG. 1 is a schematic representation of purification scheme for obtaining the compounds of the invention from culture broth.

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit of the lower limit unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As defined herein, "derived from" means directly isolated or obtained from a particular source or alternatively having identifying characteristics of a substance or organism isolated or obtained from a particular source. In the event that the "source" is an organism, "derived from" means that it may be isolated or obtained from the organism itself or from the medium used to culture or grow said organism.

As defined herein, "whole broth culture" refers to a liquid culture containing both cells and media. If bacteria are grown on a plate the cells can be harvested in water or other liquid, whole culture.

The term "supernatant" refers to the liquid remaining when cells that are grown in broth or harvested in another liquid from an agar plate are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal and particularly, nematicidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods and electrophoretic methods.

A "carrier" as defined herein is an inert, organic or inorganic material, with which the active ingredient is mixed or formulated to facilitate its application to plant or other object to be treated, or its storage, transport and/or handling.

The term "modulate" as defined herein is used to mean to alter the amount of pest infestation or rate of spread of pest infestation.

The term "pest infestation" as defined herein, is the presence of a pest in an amount that causes a harmful effect including a disease or infection in a host population or emergence of an undesired weed in a growth system.

A "pesticide" as defined herein, is a substance derived from a biological product or chemical substance that increase mortality or inhibits the growth rate of plant pests and includes but is not limited to nematicides, insecticides, plant fungicides, plant bactericides, and plant viricides.

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituent's as set forth above.

"Percent Identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Optimal alignment of sequences for comparison can use any means to analyze sequence identity (homology) known in the art, e.g., by the progressive alignment method of termed "PILEUP" (Morrison, 1997), as an example of the use of PILEUP); by the local homology algorithm of Smith & Waterman, (1981); by the homology alignment algorithm of Needleman & Wunsch (1970); by the search for similarity method of Pearson (1988); by computerized implementations of these algorithms (e.g., GAP, BEST FIT, FASTA, and TFASTA in the Wisconsin Genetics Software Package, Genetics Computer Group, 575 Science Dr., Madison, Wis.);

ClustalW (CLUSTAL in the PC/Gene program by Intelligenetics, Mountain View, Calif., described by, e.g., Higgins (1988); Corpet (1988); Huang (1992); and Pearson (1994); Pfamand Sonnhammer (1998); TreeAlign (Hein (1994); MEG-ALIGN, and SAM sequence alignment computer programs; or, by manual visual inspection.

Another example of an algorithm that is suitable for determining sequence similarity is the BLAST algorithm, which is described in Altschul et al., (1990). The BLAST programs (Basic Local Alignment Search Tool) of Altschul, S. F., et al., (1993) searches under default parameters for identity to sequences contained in the BLAST "GENEMBL" database. A sequence can be analyzed for identity to all publicly available DNA sequences contained in the GENEMBL database using the BLASTN algorithm under the default parameters. Software for performing BLAST analyses is publicly available through the National Center for Biotechnology Information, see also Zhang (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al., (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992)) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993).

Methods of Production

As noted above, compounds or metabolites may be obtained, are obtainable or are derived from an organism having the identifying characteristics of a *B. megaterium*, or alternatively from any other microorganism. The methods comprise growing these organisms (e.g., in culture) and obtaining the compounds and/or compositions of the present invention by isolating these compounds from the culture of these organisms.

In particular, the organisms are cultivated in nutrient medium using methods known in the art. The organisms may be cultivated by shake flask cultivation, small scale or large scale fermentation (including but not limited to continuous, batch, fed-batch, or solid state fermentations) in laboratory or industrial fermentors performed in suitable medium and under conditions allowing cell growth. The cultivation may take place in suitable nutrient medium comprising carbon and nitrogen sources and inorganic salts, using procedures known in the art. Suitable media are available from commercial sources or can be prepared according to published compositions.

After cultivation, a supernatant, filtrate and/or extract of or derived from *B. megaterium* may be used in formulating a pesticidal composition.

Alternatively, after cultivation, the compounds and/or metabolites may be extracted from the culture broth.

The extract may be fractionated by chromatography. Chromatographic fractions may be assayed for toxic activity against, for example, free-living nematodes and plant parasitic nematodes, *M. incognita* and/or *M. hapla* using methods known in the art. This process may be repeated one or more times using the same or different chromatographic methods.

Compositions

Compositions may comprise whole broth cultures, liquid cultures, or suspensions of a strain from a *B. megaterium*, as well as supernatants, filtrates or extracts obtained from a strain of a *B. megaterium*, or the supernatant, filtrate and/or extract or one or more metabolites or isolated compounds derived from a strain of a *B. megaterium* or combinations of the foregoing which in particular have nematicidal activity against any of the following: seed gall nematodes (*Afrina wevelli*), bentgrass nematodes (*Anguina agrostis*), shoot gall nematodes (*Anguina* spp.), seed gall nematodes (*Anguina* spp., *A. amsincikiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf for fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice white-tip (or spring dwarf, or strawberry bud) nematodes (*A. besseyi*), fungus-feeding (mushroom) nematodes (*Aphelenchoides composticola*), *Atalodera* spp. (*Atalodera lonicerue, Atalodera ucri*), spine nematodes (*Bakernema variabile*), sting nematodes (*Belonolaimus* spp., *B. gracilis, B. longicaudatis*), pine wood nematodes (*Bursaphalenchus* spp., *B. xylophilus, B. mucronatus*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Criconema* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stern and bulb nematodes (*Ditylenchus* spp., *D. angustus, D. dipsaci, D. destructor, D. intermedius*), Mushroom spawn nematodes (*D. myceliophagus*), awl nematodes (*Dolichodorus* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilieae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenettie cyst nematodes (*G. tabacum virginiae*), pin nematodes (*Gracilacus* spp., *G. idalimus*), spiral nematodes (*Helicotylenchus* spp., *H. africanus, H. digonicus, H. dihystera, H. erythrinae, H. multicinctus, H. paragirus, H. psendorobustus, H. solani, H. spicaudatus*), sheathoid nematodes (*Hermicriconemoides* spp., *H. biformis, H. californianus, H. chitwoodi, H. floridenisis, H. wessoni*), sheath nematodes (*Hemicycliophora* spp., *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenue*), Cajamis (or pigeon pea) cyst nematodes (*H. cajani*), bermudagrass (or heart-shaped, or Valentine) cyst nematodes (*H. cardiolata*), carrot cyst nematodes (*H. carotae*), cabbage cyst nematodes or *brassica* root eelworm (*H. cruciferae*), nutgrass (or sedge) cyst nematodes (*H. cyperi*), Japanese cyst nematodes (*H. elachista*), fig (or ficus, or rubber) cyst nematodes (*H. fici*), galeopsis cyst nematodes (*H. galeopsidis*), soybean cyst nematodes (*H. glycines*), alfalfa root (or pea cyst) nematodes (*H goettingiana*), buckwheat cyst nematodes (*H. graduni*), barley cyst nematodes (*H. hordecatis*), bop cyst nematodes (*H. humuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst, nematodes (*H. major*), grass cyst nematodes (*H. mani*), lucerne cyst nematodes (*H. inedicaginis*), cyperus (or motha) cyst nematodes (*Heterodera mothi*), rice cyst nematodes (*H. oryzae*), Amu-Darya (or camel thorn cyst) nematodes (*H. oxiana*), dock cyst nematodes (*H. roSii*), rumex cyst nemtodes (*H. rumicis*), sugar beet cyst nematodes (*H. scleranthii*), willow cyst nematodes (*H. saliaophila*), knawel cyst nematodes (*H. scieranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli*, *H. candacrena*, *H. gracilis*, *H. oryzae*); lance nematodes (*Hopiolainuts* spp.), Columbia nematodes (*H. columbus*), Cobb's lance nematodes (*H. galeatus*), crown-headed lance nematodes (*H. tylenchiformis*), pseudo root-knot nematodes (*Hypsoperine graminis*), needle nematodes (*Longidorus* spp., *L. africanus*, *L. sylphus*), ring nematodes (*Macroposthonia* (=*Mesocriconema*) *xenoplax*), cystoid nematodes (*Meloidodea* spp.), pine cystoid nematodes (*M. florideasis*), tadzhik cystoid nematodes (*M. tadshikistanica*), cystoid body nematodes (*Meloidoderita* spp.), stunt nematodes (*Merlinius* spp., *M. brevidens*, *M. conicus*, *M. grandis*, *M. microdorus*), root-knot nematodes (*Meloidogyne* spp., *M. acronea*, *M. arenaria*, *M brevicauda*, *M. camelliae*, *M. carolinensis*, *M. chitwoodi*, *M. exigna*, *M. graminicola*, *M. hapla*, *M. hispanica*, *M. incognita*, *M. incognita acrita*, *M. indica*, *M. inornata*, *M. javanica*, *M. kikuyuensis*, *M. konaensis*, *M. mail*, *M. microtyla*, *M. naasi*, *M. ovalis*, *M. platani*, *M, querciana*, *M. sasseri*, *M. tadshikistanica*, *M. thamesi*), knapweed nematodes (*Mesoanguina picridis*), Douglas fir nematodes (*Nacobbodera chitwoodi*), false root-knot nematodes (*Nacobbus aberrans*, *N. batatiformis*, *N. dorsalis*), sour paste nematodes (*Panagrellus redivivus*), beer nematodes (*P. situsiae*), needle nematodes (*Paralongidorus micolaimus*), spiral nematodes (*Pararotyienchus* spp.), stubby-root nematodes (*Paratrichodorus allitus*, *P. minor*, *P. porosus*, *P. renifer*), pin nematodes (*Paratylencitus* spp. *P. baidaccii*, *P. bukowinensis*, *P. curvitatus*, *P. dianthus*, *P. dachistus*, *P. hamatus*, *P. holdemani*, *P. italiensis*, *P. lepidus*, *P. nanus*, *P. neoamplycephaius*, *P. similis*), lesion (or meadow) nematodes (*Pratylcnchus* spp., *P. alleni*, *P, brachyurus*, *P. coffeae*, *P. convallariac*, *P. crenatus*, *P. flakkensis*, *P. goodeyi*, *P. hexincisus*, *P. leiocephalus*, *P. minyus*, *P. musicola*, *P. neglectus*, *P. penetrans*, *P. pratensis*, *P. scribneri*, *P. thornei*, *P. vulnus*, *P. zeae*), stem gall nematodes (*Pterotylenchtis cecidogenus*), grass cyst nematodes (*Punctodera punctate*), stunt nematodes (*Quinisulcius acutus*, *Q. capitatus*), burrowing nematodes (*Radopholus* spp.), banana-root nematodes (*R. similis*), rice-root nematodes (*R. oryzae*), red ring (or coconut, or cocopalm) nematodes (*Rhadinaphelenchus cocophilus*), reniform nematodes (*Rotylenchtdus* spp., *R. reniformis*, *R. parvus*), spiral nematodes (*Rotyienchus* spp., *R. buxophilus*, *R. christiei*, *R. robustus*), Thorne's lance nematodes (*R. uniformis*), *Sarisodera hydrophylia*, spiral nematodes (*Scutellonerna* spp., *S. biabeum*, *S. brachyurum*, *S. bradys*, *S. clathricaudatum*, *S. christiei*, *S. conicephalum*), grass root-gall nematodes (*Subanguina radicicola*), round cystoid nematodes (*Thecavermiculatus andinus*), stubby-root nematodes (*Trichodorus* spp., *T. christiei*, *T. kurumeensis*, *T. pachydermis*, *T. primitivus*), vinegar eels (or nematodes) (*Turbatrix aceti*), stunt (or stylet) nematodes (*Tylenchorhynchus* spp., *T. agri*, *T. annulatus*, *T. aspericutis*, *T. claytoni*, *T. ebriensis*, *T. elegans*, *T. golden*, *T. graciliformiis*, *T. martini*, *T. mashhoodi*, *T. microconus*, *T. nudus*, *T. oleraceae*, *T. penniseti*, *T. punensis*), citrus nematodes (*Tylenchulus semipenetrans*), dagger nematodes (*Xiphinema* spp., *X. americanum*, *X. bakeri*, *X. brasiliense*, *X. brevicolle*, *X. chambersi*, *X. coxi*, *X. diversicaudatum*, *X. index*, *X. insigne*, *X. nigerierise*, *X. radicicola*, *X. setariae*, *X. vulgarae*, *X. vuittenezi*).

The compositions set forth above can be formulated in any manner. Non-limiting formulation examples include but are not limited to Emulsifiable concentrates (EC), Wettable powders (WP), Soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), etc. In any formulation described herein, percent of the active ingredient is within a range of 0.01% to 99.99%.

The compositions may be in the form of a liquid, gel or solid. A solid composition can be prepared by suspending a solid carrier in a solution of active ingredient(s) and drying the suspension under mild conditions, such as evaporation at room temperature or vacuum evaporation at 65° C. or lower.

A composition may comprise gel-encapsulated active ingredient(s). Such gel-encapsulated materials can be prepared by mixing a gel-forming agent (e.g., gelatin, cellulose, or lignin) with a culture or suspension of live or inactivated *B. megaterium*, or a cell-free filtrate or cell fraction of a *B. megaterium* culture or suspension, or a spray- or freeze-dried culture, cell, or cell fraction or in a solution of pesticidal compounds used in the method of the invention; and inducing gel formation of the agent.

The composition may additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition set forth above may be combined with another microorganism and/or pesticide (e.g, nematicide, fungicide, insecticide). The microorganism may include but is not limited to an agent derived from *Bacillus* sp. (e.g., *Bacillus firmus*, *Bacillus thuringiensis*, *Bacillus pumilus*, *Bacillus licheniformis*, *Bacillus amyloliquefaciens*, *Bacillus subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp (*S. bikiniensis*, *S. costaricanus*, *S. avermitilis*), *Burkholderia* sp., *Trichoderma* sp., *Gliocladium* sp., avermectin, *Myrothecium* sp., *Paecilomyces* spp., *Sphingobacterium* sp., *Arthrobotrys* sp., *Chlorosplrnium*, *Neobulgaria*, *Daldinia*, *Aspergil-*

*lus, Chaetomium, Lysobacter* spp, *Lachnum papyraceum, Verticillium suchlasporium, Arthrobotrys oligospora, Verticillium chlamydosporium, Hirsutella rhossiliensis, Pochonia chlamydosporia, Pleurotus ostreatus, Omphalotus olearius, Lampteromyces japonicas, Brevudimonas* sp., *Muscodor* sp.

Alternatively, the agent may be a natural oil or oil-product having nematicidal, fungicidal and/or insecticidal activity (e.g., paraffinic oil, tea tree oil, lemongrass oil, clove oil, cinnamon oil, citrus oil including but not limited to bitter orange, orange, lemon; rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, saponins). Furthermore, the pesticide may be a single site anti-fungal agent which may include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin may include but is not limited to azoxystrobin, kresoxim-methoyl or trifloxystrobin. In yet another particular embodiment, the anti-fungal agent is a quinone, e.g., quinoxyfen (5,7-dichloro-4-quinolyl 4-fluorophenyl ether). The anti-fungal agent may also be derived from a *Reynoutria* extract.

The fungicide can also be a multi-site non-inorganic, chemical fungicide selected from the group consisting of chloronitrile, quinoxaline, sulphamide, phosphonate, phosphite, dithiocarbamate, chloralkylhios, phenylpyridin-amine, cyano-acetamide oxime.

As noted above, the composition may further comprise a nematicide. This nematicide may include but is not limited to chemicals such as organophosphates, carbamates, and fumigants, and microbial products such as avermectin, *Myrothecium* sp. Biome (*Bacillus firmus*), *Pasteuria* spp., *Paecilomyces*, and organic products such as saponins and plant oils.

The compositions may be applied using methods known in the art. Specifically, these compositions may be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds. Treatment of the plants and plant parts with the compositions set forth above may be carried out directly or by allowing the compositions to act on their surroundings, habitat or storage space by, for example, immersion, spraying, evaporation, fogging, scattering, painting on, injecting. In the case that the composition is applied to a seed, the composition may be applied to the seed as one or more coats prior to planting the seed, or applied as a slurry or dust when planting, using one or more coats using methods known in the art. The seed in a particular embodiment may be a genetically modified seed.

Plants that may be treated include but are not limited to: (A) Major edible food crops, which include but are not limited to (1) Cereals (e African rice, barley, durum wheat, einkorn wheat, emmer wheat, finger millet, foxtail millet, hairy crabgrass, Indian barnyard millet, Japanese barnyard millet, maize, nance, oat, pearl millet, proso millet, rice, rye, *sorghum, Sorghum* spp., rye, spelt wheat); (2) Fruits (e.g., abiu, acerola, achacha, African mangosteen, alpine currant, ambarella, American gooseberry, American persimmon, apple, apricot, araza, Asian palmyra palm, Asian pear, atemoya, Australian desert raisin, avocado, azarole, babaco, bael, banana, Barbados gooseberry, bergamot, betel nut, bignay, bilberry, bilimbi, binjai, biriba, bitter orange, black chokeberry, black mulberry, black sapote, blackberry, blueberried honeysuckle, borojo, breadfruit, murmese grape, button mangosteen, cacao, calamondin, canistel, cantaloupe, cape gooseberry, cashew nut, cassabanana, cempedak, charichuelo, cherimoya, cherry, cherry of the Rio Grande, cherry plum, Chinese hawthorn, Chinese white pear, chokeberry, citron, cocona, coconut, cocoplum, coffee, coffee Arabica, coffee robusta, Costa Rica pitahaya, currants, custard apple, date, date-plum, dog rose, dragonfruit, durian, elderberry, elephant apple, Ethiopian eggplant, European nettle tree, European wild apple, *feijoa*, fig, gac, genipapo, giant granadilla, gooseberry, goumi, grape, grapefruit, great *morinda*, greengage, guava, hardy kiwi, hog plum, horned melon, horse mango, Indian fig, Indian jujube, jabuticaba, jackberry, jackfruit, Japanese persimmon, Japanese wineberry, jocote, jujube, kaffir lime, karanda, kei apple, kepel apple, key lime, kitembilla, kiwi fruit, korlan, kubal vine, kuwini mango, kwai muk, langsat, large cranberry, lemon, Liberian coffee, longan, loquat, lychee, malay apple, mamey sapote, mammee apple, mango, mangosteen, maprang, marang, medlar, melon, Mirabelle plum, miracle fruit, monkey jack, moriche palm, mountain papaya, mountain soursop, mulberry, naranjilla, natal plum, northern highbush blueberry, olive, otaheite gooseberry, oval kumquat, papaya, para guava, passionfruit, pawpaw, peach, peach-palm, pear, pepino, pineapple, pitomba *Eugenia* luschnathiana, pitomba talisia esculenta, plantain, plum, pomegranate, pomelo, pulasan, purple chokeberry, quince, rambutan, ramontchi, raspberry, red chokeberry, red currant, red mulberry, red-fruited strawberry guava, rhubarb, rose apple, roselle, safou, salak, salmonberry, santol, sapodilla, satsuma, seagrape, soncoya, sour cherry, soursop, Spanish lime, Spanish tamarind, star apple, starfruit, strawberry, strawberry guava, strawberry tree, sugar apple, Surinam cherry, sweet briar, sweet granadilla, sweet lime, tamarillo, tamarind, tangerine, tomatillo, tucuma palm, *Vaccinium* spp., velvet apple, wampee, watermelon, watery rose apple, wax apple, white currant, white mulberry, white sapote, white star apple, wolfberry (*Lyceum barbarum, L. chinense*), yellow mombin, yellow pitaya, yellow-fruited strawberry, guava, (3) Vegetables (e.g., ackee, agate, air potato, *Amaranthus* spp., American groundnut, antroewa, armenian cucumber, arracacha, arrowleaf elephant ear, arrowroot, artichoke, ash gourd, asparagus, avocado, azuki bean, bambara groundnut, bamboo, banana, barbados gooseberry, beet, beet root, bitter gourd, bitter vetch, bitterleaf, black mustard, black radish, black salsify, blanched celery, breadfruit, broad bean, broccoli, brussels sprout, Buck's horn plantain, buttercup squash, butternut squash, cabbage, caigua, calabash, caraway seeds, carob, carrot, cassabanana, cassava, catjang, cauliflower, celeriac, celery, celtuce, chard, chayote, chickpea, chicory, chilacayote, chili pepper (*Capsicum annuum, C. baccatum, C. chinense, C. frutescens, C. pubescens*), Chinese cabbage, Chinese water chestnut, Chinese yam, chives, chufa sedge, cole crops, common bean, common purslane, corn salad, cowpea, cress, cucumber, cushaw pumpkin, drumstick tree, eddoe, eggplant, elephant foot yam, elephant garlic, endive, enset, Ethiopian eggplant, Florence fennel, fluted gourd, gac, garden rocket, garlic, geocarpa groundnut, good king henry, grass pea, groundut, guar bean, horse gram, horseradish, hyacinth bean, iceplant, Indian fig, Indian spinach, ivy gourd, Jerusalem artichoke, jicama, jute, kale, kohlrabi, konjac, kurrat, leek, lentil, lettuce, Lima bean, lotus, *luffa*, maca, maize, mangel-wurzel, mashua, moso bamboo, moth bean, mung bean, napa cabbage, neem, oca, okra, oldham's bamboo, olive, onion, parsnip, pea, pigeon pea, plantain, pointed gourd, potato, pumpkins, squashes, quinoa, radish, rapeseed, red amaranth, rhubarb, ribbed gourd, rice bean, root parsley, runner bean, rutabaga, sago palm, salsify, scallion, sea kale, shallot, snake gourd, snow pea, sorrel, soybean, spilanthes, spinach, spinach beet, sweet potato, taro, tarwi, teasle gourd, tepary bean, tinda, tomato, tuberous pea, turnip, turnip-rooted chervil, urad bean, water caltrop trapa bicornis, water caltrop trapa natans, water morning slory, watercress, welsh onion, west African okra, west Indian gherkin, white goosefoot, white yam, winged bean, winter purslane, yacón, yam, yardlong bean, zucchinietables); (4) Food crops (e.g., abiu, acerola, achacha, ackee, African mangosteen, African rice, agate, air potato, alpine currant, *Amaranthus* app., Ambarrella, American gooseberry, American groundnut, American persimmon, antroewa, apple, apricot, arazá, Armenian cucumber, arracacha, arrowleaf elephant ear, arrowroot, artichoke, ash gourd, Asian palmyra palm, Asian pear, asparagus, atemoya, Australian desert raisin, avocado, azarole, azuki bean, babaco, bael, bambara groundnut, bamboo, banana, barbados gooseberry, barley, beet, beetroot, bergamot, betel nut, bignay, bilberry, bilimbi, binjai, biriba, bitter gourd, bitter orange, bitter vetch, bitterleaf, black chokeberry, black currant, black mulberry, black mustard, black radish, black salsify, black sapote, blackberry, blanched celery, blue-berried honeysuckle, borojo, breadfruit, broad bean, broccoli, Brussels sprout, Buck's horn plantain, buckwheat, Burmese grape, buttercup squash, butternut squash, button mangosteen, cabbage, cacao, caigua, calabash, calamondin, canistel, cantaloupe, cape gooseberry, caraway seeds, carob, carrot, cashew nut, cassaya, catjang, cauliflower, celeriac, celery, celtuce, cempedak, chard, charichuelo, chayote, cherimoya, cherry, cherry of the Rio Grande, cherry plum, chickpea, chicory, chilacayote, chili pepper (*Capsicum annuum, C. baccatum, C. chinense, C. frutescens, C. pubescens*), Chinese cabbage, Chinese hawthorn, Chinese water chestnut, Chinese white pear, Chinese yam, chives, chokeberry, chufa sedge, citron, cocona, coconut, cocoplum, coffee, coffee (Arabica and Robusta types), cole crops, common bean, common purslane, corn salad, Costa Rica pitahaya, cowpea, cress, cucumber, currants, cushaw pumpkin, custard apple, date, date-plum, dog rose, dragonfruit, drumstick tree, durian, durum wheat, eddoe, eggplant, einkorn wheat, elderberry, elephant apple, elephant foot yam, elephant garlic, emmer wheat, endive, enset, Ethiopian eggplant, European nettle tree, European wild apple, *feijoa*, fig, finger millet, florence fennel, fluted gourd, foxtail millet, gac, garden rocket, garlic, genipapo, geocarpa groundnut, giant granadilla, good king henry, gooseberry, goumi, grape, grapefruit, grass pea, great *morinda*, greengage, groundnut, grumichama, guar bean, guava, hairy crabgrass, hardy kiwi, hog plum, horned melon, horse gram, horse mango, horseradish, hyacinth bean, iceplant, Indian barnyard millet, Indian fig, Indian jujube, Indian spinach, ivy gourd, jabuticaba, jackalberry, jackfruit, jambul, Japanese barnyard millet, Japanese persimmon, Japanese wineberry, Jerusalem artichoke, jocote, jujube, jute, kaffir lime, kale, karanda, kei apple, kepel apple, key lime, kitembilla, kiwifruit, kohlrabi, konjac, korlan, kubal vine, kurrat, kuwini mango, kwai muk, langsat, large cranberry, leek, lemon, lentil, lettuce, Liberian coffee, lima bean, longan, loquat, lotus, *luffa*, lychee, maca, maize, malay apple, mamey saptoe, mammee apple, mangel-wurzel, mango, mangosteen, maprang, marang, mashua, medlar, melon, Mirabelle plum, miracle fruit, monk fruit, monkey jack, moriche palm, moso bamboo, moth bean, mountain papaya, mountain soursop, mulberry, mung bean, mushrooms, nance, napa cabbage, naranjilla, natal plum, neem, northern highbush blueberry, oat, oca, oil palm, okra, oldman's bamboo, olive, onion, orange, otaheite gooseberry, oval kumquat, papaya, para guava, parsnip, passionfruit, pawpaw, pea, peach, peachpalm, pear, pearl millet, pepino, pigeon pea, pineapple, Pitomba (*Eugenia luschnathiana, Talisia esculenta*), plantain, plum, pointed gourd, pomegranate, pomelo, potato, proso millet, pulasan, pumpkins and squashes, purple chokeberry, quince, quinoa, radish, rambutan, ramontchi, rapeseed, raspberry, red amaranth, red chokeberry, red currant, red mulberry, red-fruited strawberry guava, rhubarb, ribbed gourd, rice, rice bean, root parsley, rose apple, roselle, runner bean, rutabaga, rye, safou, sago palm, salak, salmonberry, salsify, santol, sapodilla, Satsuma, scallion, sea kale, seagrape, shallot, snake gourd, snow pea, soncoya, *sorghum, Sorghum* spp., sorrel, sour cherry, soursop, soybean, Spanish lime, Spanish tamarind, spelt wheat, spilanthes, spinach, spinach beet, star apple, starfruit, strawberry, strawberry guava, strawberry tree, sugar apple, sugar beet, sugarcane, surinam cherry, sweet briar, sweet granadilla, sweet lime, sweet potato, tamarillo, tamarind, tangerine, taro, tarwi, teasle gourd, tef, tepary bean, tinda, tomatillo, tomato, tuberous pea, tucuma palm, turnip, turnip-rooted chervil, urad bean, *Vaccinium* spp., velvet apple, wampee, water caltrop (*Trapa bicornis, T. natans*), water morning glory, watercress, watermelon, watery rose apple, wax apple, welsh onion, west African okra, west Indian gherkin, wheat, white currant, white goosefoot, white mulberry, white sapote, white star apple, white yam, winged bean, winter purslane, wolfberry (*Lycium barbarum, L. chinense*), yacón, yam, yangmei, yard-long bean, yellow mombin, yellow pitaya, yellow-fruited strawberry guava, zucchini; (B) Other edible crops, which includes but is not limited to (1) Herbs (e.g., Absinthium, alexanders, basil, bay laurel, betel nut, camomile, chervil, chili pepper (*Capsicum annuum, C. baccatum, C. chinense, C. frutescens, C. pubescens*), chili peppers, chives, cicely, common rue, common thyme, coriander, cress, culantro, curly leaf parsley, dill, epazote, fennel, flat leaf parsley, ginseng, gray santolina, herb hyssop, holy basil, hop, jasmine, kaffir lime, lavender, lemon balm, lemon basil, lemon grass, lovage, marjoram, mint, oregano, parsley, peppermint, *perilla*, pot marigold, rooibos, rosemary, sage, shiny-leaft buckthorn, sorrel, spearmint, summer savory, tarragon, That basil, valerian, watercress, wild betel, winter savory, yerba mate); (2) Spices (e.g., ajowan, allspice, anise, bay laurel, black cardamom, black mustard, black pepper, caper, caraway seeds, cardamom, chili pepper (*Capsicum annuum, C. baccatum, C. chinense, C. frutescens, C. pubescens*), chili peppers, cinnamon, clove, common juniper, coriander, cumin, fennel, fenugreek, garlic, ginger, kaffir lime, liquorice, nutmeg, oregano, pandan, parsley, saffron, star anise, turmeric, vanilla, white mustard); (2) Medicinal plants (e.g., absinthium, alfalfa, aloe vera, anise, artichoke, basil, bay laurel, betel leaf, betel nut, bilberry, black cardamom, black mustard, black pepper, blue gum, borojo, camomlie, caper, cardamom, castor bean, chili peppers, Chinese yam, chives, cola nut, common jasmine, common lavender, common myrrh, common rue, cilantro, cumin, dill, dog rose, epazote, fennel, fenugreek, gac, garlic, ginger, gray santolina, gum Arabic, herb hyssop, holy basil, horseradish, incense tree, lavender, lemon grass, liquorice, lovage, marijuana, marjoram, monk fruit, neem, opium, oregano, peppermint, pot marigold, quinine, red acacia, red currant, rooibos, safflower, sage, shiny-leaf buckthorn, sorrel, spilanthes, star anise, tarragon, tea, turmeric, valerian, velvet bean, watercress, white mustard, white sapote, wild betel, wolfberry (*Lycium barbarum, L. chinense*), yerba mate); (3) Stimulants (e.g., betel leaf, betel nut, cacao, chili pepper (*Capsicum annuum*, C. baccatum, C. chinense, C. frutescens, *C. pubescens*), chili peppers, coffee, coffee (Arabica, Robusta), cola nut, khat, Liberian coffee, tea, tobacco, wild betel, yerba mate); (4) Nuts (e.g., almond, betel nut, Brazil nut, cashew nut, chestnut, Chinese water chestnut, coconut, cola nut, common walnut, groundnut, hazelnut, Japanese stone oak, *macadamia*, nutmeg, paradise nut, pecan nut, pistachio nut, walnut); (5) Edible seeds (e.g., black pepper, Brazil nut, chilacayote, cola nut, fluted gourd, lotus, opium, quinoa, sesame, sunflower, water caltrop (*Trapa bicornis, T. natans*); (6) Vegetable oils (e.g., black mustard, camelina, castor bean, coconut, cotton, linseed, maize, neem, niger seed, oil palm, olive, opium, rapeseed, safflower, sesame, soybean, sunflower, tung tree, turnip); (7) Sugar crops (e.g., Asian palmyra palm, silver date palm, *sorghum*, sugar beet, sugarcane); (8) Pseudocereals (e.g., *Amaranthus* spp., buckwheat, quinoa, red amaranth); (9) Aphrodisiacs (e.g., borojo, celery, durian, garden rocket, ginseng, maca, red acacia, velvet bean); (C) Non food categories, including but not limited to (1) forage and dodder crops (e.g., agate, alfalfa, beet, broad bean, camelina, catjang, grass pea, guar bean, horse gram, Indian barnyard millet, Japanese barnyard millet, lespedeza, lupine, maize, mangel-wurzel, mulberry, niger seed, rapeseed, rice bean, rye); (2) Fiber crops (e.g., coconut, cotton, fique, hemp, henequen, jute, kapok, kenaf, linseed, manila hemp, New Zealand flax, ramie, roselle, sisal, white mulberry); (3) Energy crops (e.g., blue gum, camelina, cassaya, maize, rapeseed, *sorghum*, soybean, Sudan grass, sugar beet, sugarcane, wheat); (4) Alcohol production, (e.g., barley, plum, potato, sugarcane, wheat, *sorghum*); (5) Dye crops (e.g., chay root, henna, indigo, old fustic, safflower, saffron, turmeric); (6) Essential oils (e.g., allspice, bergamot, bitter orange, blue gum, camomile, citronella, clove, common jasmine, common juniper, common lavender, common myrrh, field mint, freesia, gray santolina, herb hyssop, holy basil, incense tree, jasmine, lavender, lemon, marigold, mint, orange, peppermint, pot marigold, spearmint, ylang-ylang tree); (6) Green manures (e.g., alfalfa, clover, lacy Phacelia, sunn hemp, trefoil, velvet bean, vetch); (7) Erosion prevention (e.g., bamboo, cocoplum; (8) Soil improvement (e.g., lupine, vetch); (9) Cover crops (e.g., Alfalfa, lacy Phacelia, radish); (10) Botanical pesticides (e.g., jicama, marigold, neem, pyrethrum); (11) Cut flowers (e.g., carnation, chrysanthemum, daffodil, dahlia, freesia, gerbera, marigold, rose, sunflower, tulip); (12) Ornamental plants (e.g., African mangosteen, aloe vera, alpine currant, aster, black chokeberry, breadfruit, calamondin, carnation, cassabanana, castor bean, cherry plum, chokeberry, chrysanthemum, cocoplum, common lavender, crocus, daffodil, dahlia, freesia, gerbera, hyacinth, Japanese stone oak, Jasmine, lacy Phacelia, lotus, lupine, marigold, New Zealand flax, opium, purple chokeberry, ramie, red chokeberry, rose, sunflower, tulip, white mulberry); (D) Trees which include but are not limited to abelia. almond. apple, apricot. arborvitae american, arborvitae, ash, aspen, azalea, baidcypress, beautybush, beech, birch, black tupelo, blackberry, blueberry, boxwood, buckeye, butterfly bush, butternut, camellia, catalpa, cedar, cherry, chestnut, coffeetree, crab trees, crabapple, crapemyrtle, cypress, dogwood, douglasfir, ebony, elder American, elm, fir, forsythia, ginkgo, goldenraintree, hackberry, hawthorn, hazelnut, hemlock, hickory, holly, honeylocust, horsechestnut, hydrangea, juniper, lilac, linden, magnolia, maple, mockorange, mountainash, oak, olive, peach, pear, pecan, pine, pistache, planetree, plum, poplar, pivet, raspberry, redbud, redcedar, redwood, rhododendron, rose-ofsharon, sassafras, *sequoia*, serviceberry, smoketree, soapberry, sourwood, spruce, strawberry tree, sweetshrub, sycamore, tuliptree, viburnum, walnut, weigela, willow, winterberry, witchhazel, zelkova; (E) Turf which includes but is not limited to Kentucky bluegrass, tall fescue, Bermuda grass, zoysia grass, perennial ryegrass, fine fescues (e.g.; creeping red, chewings, hard, or sheep fescue).

The compositions may also be applied to the soil using methods known in the art (see, for example, Chitwood, "Nematicides", available at naldc.nal.usda.gov/download/43874/PDF. Such methods include but are not limited to fumigation, drip irrigation or chemigation, soil incorporation, soil drenching, seed treatment and dressing, bare root dip.

Pesticidal Uses

The compositions, cultures, supernatants, metabolites and pesticidal compounds set forth above may be used as pesticides. In particular, the compositions, cultures, supernatants, metabolites and pesticidal compounds as set forth above may be used as insecticides and nematicides, alone or in combination with one or more pesticidal substances set forth above. Specifically, nematodes that may be controlled using the method set forth above include but are not limited to free living nematodes, parasitic nematodes such as root-knot, cyst, and lesion nematodes, including but not limited to seed gall nematodes (*Afrina wevelli*) bentgrass nematodes (*Anguina agrostis*), shoot gall nematodes (*Anguina* spp.), seed gall nematodes (*Anguina* spp., *A. amsinckiae, A. balsamophila; A. tritici*), fescue leaf gall nematodes (*A. graminis*), ear-cockle (or wheat gall) nematodes (*Anguina tritici*), bud and leaf (or foliar) nematodes (*Aphelenchoides* spp., *A. subtenuis*), begonia leaf (or fern, or spring crimp, or strawberry foliar, or strawberry nematodes, or summer dwarf) nematodes (*A. fragariae*), fern nematodes (*A. olesistus*), rice nematodes (*A. oryzae*), currant nematodes (*A. ribes*), black currant (or chrysanthemum) nematodes (*A. ritzemabosi*), chrysanthemum foliar or leaf nematodes (*A. ritzemabosi*), rice whitetip (or spring dwarf, or strawberry bud) nematodes (*A. besseyi*), fungus-feeding (mushroom) nematodes (*Aphelenchoides composticola*), *Atalodera* spp. (*Atalodera lonicerae, Atalodera ucri*), spine nematodes (*Bakernema variabile*), sting nematodes (*Belonolainuis* spp., *B. gracilis, B. langicaudatus*), pine wood nematodes (*Bursaphalenchus* spp., *B. xylophilus, B. mucronauts*), sessile nematodes (*Cacopaurus* spp., *C. epacris, C. pestis*), amaranth cyst nematodes (*Cactodera amaranthi*), birch cyst nematodes (*C. betulae*), cactus cyst nematodes (*C. cacti*), estonian cyst nematodes (*C. estonica*), Thorne's cyst nematodes (*C. thornei*), knotweed cyst nematodes (*C. weissi*), ring nematodes (*Criconema* spp.), spine nematodes (*Cricanerna* spp., *C. civellae, C. decalineatum, C. spinalineatum*), ring nematodes (*Criconemella axeste, C. curvata, C. macrodora, C. parva*), ring nematodes (*Criconemoides* spp., *C. citri, C. simile*), spine nematodes (*Crossonema fimbriatum*), eucalypt cystoid nematodes (*Cryphodera eucalypti*), bud, stem and bulb nematodes (*Ditylenchus* spp., *D. angustus, D. dipsaci, D. destructor, D. intermedius*), Mushroom spawn nematodes (*D. myceliophagus*), awl nematodes (*Dolichodonts* spp., *D. heterocephalus, D. heterocephalous*), spear nematodes (*Dorylaimus* spp.), stunt nematodes (*Geocenamus superbus*), cyst nematodes (*Globodera* spp.), yarrow cyst nematodes (*G. achilleae*), milfoil cyst nematodes (*G. millefolii*), apple cyst nematodes (*G. mali*), white cyst potato nematodes (*G. pallida*), golden nematodes (*G. rostochiensis*), tobacco cyst nematodes (*G. tabacum*), Osborne's cyst nematodes (*G. tabacum solanacearum*), horsenette cyst nematodes (*G. tabacum virginiae*), pin nematodes (*Gracilactts* spp., *G. idalimus*), spiral nematodes (*Helicotylenchus* spp., *H. africanus, H. digonicus, H. dihystera, H. erythrinae, H. muiticinctus, H. paragirus, H. pseudorobustus, H. solani, H. spicaudatus*), sheathoid nematodes (*Hemicriconemoides* spp., *H. biformis, H. cakformianus, H. chitwoodi, H. florideasis, H. wessoni*), sheath nematodes (*Henticycilophora* spp. *H. arenaria, H. biosphaera, H. megalodiscus, H. parvana, H. poranga, H. sheri, H. similis, H. striatula*), cyst nematodes (*Heterodera* spp.), almond cyst nematodes (*H. amygdali*), oat (or cereal) cyst nematodes (*H. avenae*), Cajanus (or pigeon pea) cyst nematodes (*H. cajani*), bermudagrass or heart-shaped, or Valentine) cyst nematodes (*H. cardiolata*), carrot cyst nematodes (*H. carotae*), cabbage cyst nematodes or *brassica* root eelworm (*H. cruciferae*), nutgrass or sedge) cyst nematodes (*H. cyperi*), Japanese cyst nematodes (*H. elachista*), fig (or *ficus*, or rubber) cyst nematodes (*H. fici*), galeopsis cyst nematodes (*H. galeopsidis*), soybean cyst nematodes (*H. glycines*), alfalfa root (or pea cyst) nematodes (*H. goettingiana*), buckwheat cyst nematodes (*H. graduni*), barley cyst nematodes (*H. hordecalis*), hop cyst nematodes (*H. hamuli*), Mediterranean cereal (or wheat) cyst nematodes (*H. latipons*), lespedeza cyst nematodes (*H. lespedezae*), Kansas cyst nematodes (*H. longicolla*), cereals root eelworm or oat cyst nematodes (*H. major*), grass cyst nematodes (*H. mani*), lucerne cyst nematodes (*H. medicaginis*), *cyperus* (or motha) cyst nematodes (*Heterodera mothi*), rice cyst nematodes (*H. oryzae*), Amu-Darya (or camel thorn cyst) nematodes (*H. oxiana*), dock cyst nematodes (*H. rosii*), rumex cyst nemtodes (*H. rumicis*), sugar beet cyst nematodes (*H. schachtii*), willow cyst nematodes (*H. salixophila*), knawel cyst nematodes (*H. scleranthii*), sowthistle cyst nematodes (*H. sonchophila*), tadzhik cyst nematodes (*H. tadshikistanica*), turkmen cyst nematodes (*H. turcomanica*), clover cyst nematodes (*H. trifolii*), nettle cyst nematodes (*H. urticae*), ustinov cyst nematodes (*H. ustinovi*), cowpea cyst nematodes (*H. vigni*), corn cyst nematodes (*H. zeae*), rice root nematodes (*Hirschmanniella* spp., *H. belli, H. caudacena, H. gracilis, H. oryzae*), lance nematodes (*Hoplolaimus* spp.), Columbia nematodes (*H. columbus*), Cobb's lance nematodes (*H. galeatus*), crown-headed lance nematodes (*H, tylenchiformis*), pseudo root-knot nematodes (*Hypsoperine graminis*), needle nematodes (*Longidorus* spp., *L. africanus, L sylphus*), ring nematodes (*Macroposthonia* (*=Mesocriconema*) *xenoptax*), cystoid nematodes (*Meloidodera* spp.), pine cystoid nematodes (*M. floridensis*), tadzhik cystoid nematodes (*M. tadshikistanica*), cystoid body nematodes (*Meloidoderita* spp.), stunt nematodes (*Merlinius* spp., *M. brevidens, M. conicus, M. grandis, M. microdorus*), root-knot nematodes (*Meloidogyne* spp., *M. acronea, M. arenaia, M. artiellia, M. brevicauda, M. camelliae, M. carolinensis, M. chitwoodi, M. exigua, M. graminicola, M. hapla, M. hispanica, M. incognita, M. incognita acrita, M. indica, M. inornata, M. javanica, M. kikuyuensis, M. konaensis, M. mali, M. microtyla, M. naasi, M. ovalis, M. platani, M. querciana, M. sasseri, M. tadshikistanica, M. thamesi*), knapweed nematodes (*Mesoanguina picridis*), Douglas fir nematodes (*Nacobbodera chitwoodi*), false root-knot nematodes (*Nacobbus aberrans, N. batatiformis, N. dorsalis*), sour paste nematodes (*Panagrellus redivivus*), beer nematodes (*P. silusiae*), needle nematodes (*Paralongidorus microlaimus*), spiral nematodes (*Pararotyienchus* spp.), stubby-root nematodes (*Paratrichodorus allius, P. minor, P. porous, P. renifer*), pin nematodes (*Paratylenchus* spp., *P. baldaccii, P. bukowinensis, P. curvitatus, P. dianthus, P. elachistus, P. hamatus, P. holdemani, P. italiensis, P. lepidus, P. nanus, P. neoamplycephalus, P. similis*), lesion (or meadow) nematodes (*Pratylenchus* spp., *P. alleni, P. brachyurus, P. coffeae, P. convallariae, P. crenatus, P. flakkensis, P. goodeyi, P. hexincisus, P. leiocephalus, P. minyus, P. musicola, P. neglectus, P. penetrans, P. pratensis, P. scribneri, P. thornei, P. vulnus, P. zeae*), stem gall nematodes (*Pterotylenchus cecidogenus*), grass cyst nematodes (*Punctodera punctate*), stunt nematodes (*Quinisulcius acutus Q. capitatus*), burrowing nematodes (*Radopholus* spp.), banana-root nematodes (*R. similis*), rice-root, nematodes (*R. oryzae*), red ring (or coconut, or cocopalm) nematodes (*Rhadinaphelenchus cocophilus*), reniform nematodes (*Rotylenchulus* spp., *R. reniformis, R. parvus*), spiral nematodes (*Rotylenchus* spp., *R. buxophilus, R. christiei, R. robustus*), Thorne's lance nematodes (*R. uniformis*), *Sarisodera hydrophylla*, nematodes (*Sctuellonema* spp., *S. blaberum, S. brachyurum, S. bradys, S. clathricaudatum, S. christiei, S. conicephalum*), grass root-gall nematodes (*Subanguina radicicola*), round cystoid nematodes (*Thecavermiculatus andinus*), stubby-root nematodes (*Trichodorus* spp., *T. christiei, T. kurumeensis, T. pachydermis, T. primitivus*), vinegar eels (or nematodes) (*Turbatrix aceti*), stunt (or stylet) nematodes (*Tylenchorhynchus* spp., *T. agri, T. annulatus, T. aspericutis, T. claytoni, T. ebriensis, T. elegans, T. golden, T. graciliformis, T. martini, T. mashhoodi, T. microconus, T. nudus, T. oleraceae, T. penniseti, T. punensis*), citrus nematodes (*Tylenchulus semipenetrans*), dagger nematodes (*Xiphinema* spp., *X. americanum, X. bakeri, X. brasiliense, X. brevicolle, X. chambersi, X. coxi, X. diversicaudatum, X. index, X. insigne, X. nigeriense, X. radicicola, X. setariae, X. vulgarae, X, vuittenezi*).

Application of an effective pesticidal control amount of a supernatant, filtrate or extract containing a pesticidally active metabolite, or isolated compound produced by the *B. megaterium* or application of combinations of the foregoing is provided. The strain or supernatant or filtrate or extract, metabolite and/or compound is applied, alone or in combination with another pesticidal substance, in an effective pest control or pesticidal amount. An effective amount is defined as that quantity of microorganism cells, supernatant, filtrate or extract, metabolite and/or compound alone or in combination with another pesticidal substance that is sufficient to modulate pest infestation. The effective rate can be affected by pest species present, stage of pest growth, pest population density, and environmental factors such as temperature, wind velocity, rain, time of day and seasonality. The amount that will be within an effective range in a particular instance can be determined by laboratory or field tests.

Plant Growth Promotion

The compositions disclosed herein, in particular, *Bacillus megaterium* and/or a supernatant, filtrate, extract, compound, metabolite or cell fraction obtained from a culture of *B. megaterium*, can be used to modulate or more particularly promote growth of plants, e.g. crops such as fruit (e.g., strawberry), vegetable (e.g., tomato, squash, pepper, eggplant), or grain crops (e.g., soy, wheat, rice, corn), tree, flower, ornamental plants, shrubs (e.g., cotton, roses), bulb plant (e.g., onion, garlic) or vine (e.g., grape vine). The compositions can also be used to modulate the germination of a seed(s) in a plant(s).

The compositions disclosed herein, or formulated product, can be used alone or in combination with one or more other components as described below, such as growth promoting agents and/or anti-phytopathogenic agents in a tank mix or in a program (sequential application called rotation) with pre-determined order and application interval during the growing season. When used in a combination with the above-mentioned products, at a concentration lower than recommended on the product label, the combined efficacy of the two or more products (one of which is the said composition disclosed herein) is, in certain embodiments, greater than the sum of each individual component's effect. Hence, the effect is enhanced by synergism between these two (or more) products, and the risk for the development of pesticide resistance among the plant pathogenic strains is reduced.

The composition can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% by volume) prior to transplanting the fruit or vegetable into the soil.

Alternatively, the composition can be applied by drip or other irrigation system. Specifically, the composition can be injected into a drip irrigation system. In a particular embodiment, the composition is applied at a concentration of $1\times10^8$ CFU/ml in a volume of approximately 11 to approximately 4 quarts per acre.

In yet another embodiment, the composition can be added as an in-furrow application. Specifically, the composition can be added as an in-furrow spray at planting using nozzles calibrated to deliver a total output of 2-6 gallons/acre. Nozzles are placed in the furrow opener on the planter so that the pesticide application and seed drop into the furrow are simultaneous.

Mixtures of the disclosed compositions with, for example, a solid or liquid adjuvant are prepared in known manner. For example, mixtures can be prepared by homogeneously mixing and/or grinding the active ingredients with extenders such as solvents, solid carriers and, where appropriate, surface-active compounds (surfactants). The compositions can also contain additional ingredients such as stabilizers, viscosity regulators, binders, adjuvants as well as fertilizers or other active ingredients in order to obtain special effects.

Combinations with Plant Growth Promoting Agents

The compositions disclosed herein can be used in combination with other growth promoting agents such as synthetic or organic fertilizers (e.g., di-ammonium phosphate, in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as, for example, *Bacillus* spp., *Pseudomonads, Rhizobia*, and *Trichoderma.*

Seed Treatments

Seed treatments include application of a pesticidal composition, optionally in combination with other bioactive, antagonistic or symbiotic agents to the surface of a seed prior to sowing. Pesticidal toxins, proteins, and/or compounds disclosed herein can be applied to seeds as dry powders, slurried powders or sprayed on the seed before planting.

The compositions disclosed herein can be formulated for seed treatments in any of the following modes: dry powder, water slurriable powder, liquid solution, flowable concentrate or emulsion, emulsion, microcapsules, gel, or water dispersible granules.

In the case of a dry powder, the active ingredient is formulated similarly to a wettable powder, but with the addition of a sticking agent, such as mineral oil, instead of a wetting agent. For example, one kg of purified talc powder (sterilized for 12 h), 15 g calcium carbonate, and 10 g carboxymethyl cellulose are mixed under aseptic conditions following the method described by Nandakumar et al (2001). Active ingredient(s) is/are mixed in a 1:2.5 ratio (suspension to dry mix) and the product is shade dried to reduce moisture content to 20-35%.

The compositions disclosed herein can also be used in combination with seed-coating agents. Such seed coating agents include, but are not limited to, ethylene glycol, polyethylene glycol, chitosan, carboxymethyl chitosan, peat moss, resins and waxes or chemical fungicides or bactericides with either single site, multisite or unknown mode of action.

In additional embodiments, the disclosed compositions can be applied to seeds by seed imbibition or as a powdered inoculum.

Anti-Phytopathogenic Agents

The compositions disclosed herein can also be used in combination with other anti-phytopathogenic agents, such as plant extracts, biopesticides, inorganic crop protectants (such as copper), surfactants (such as rhamnolipids; Gandhi et al., 2007) or natural oils such as paraffinic oil and tea tree oil possessing pesticidal properties or chemical fungicides or bactericides with either single site, multisite or unknown mode of action. As defined herein, an "anti-phytopathogenic agent" is an agent that modulates the growth of a plant pathogen, particularly a pathogen causing soil-borne disease on a plant, or alternatively prevents infection of a plant by a plant pathogen. A plant pathogen includes but is not limited to a fungus, bacteria, actinomycete or virus.

As noted above, the anti-phytopathogenic agent can be a single-site anti-fungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid (xylylalanine). In a more particular embodiment, the antifungal agent is a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole). In a most particular embodiment, the antifungal agent is myclobutanil. In yet another particular embodiment, the antifungal agent is a quinone outside inhibitor (e.g., strobilurin). The strobilurin may include but is not limited to azoxystrobin, kresoxim-methyl or trifloxystrobin. In yet another particular embodiment, the anti-fungal agent is a quinone, e.g., quinoxyfen (5,7-dichloro-4-quinolyl 4-fluorophenyl ether).

In yet a further embodiment, the fungicide is a multi-site non-inorganic, chemical fungicide selected from the group consisting of chloronitrile, quinoxaline, sulphamide, phosphonate, phosphite, dithiocarbamate, chloralkylhios, phenylpyridine-amine, and cyano-acetamide oxime.

In yet a further embodiment, the anti-phytopathogenic agent can be streptomycin, tetracycline, oxytetracycline, copper, or kasugamycin.

EXAMPLES

The composition and methods set forth above will be further illustrated in the following, non-limiting Examples. The examples are illustrative of various embodiments only and do not limit the claimed invention regarding the materials, conditions, weight ratios, process parameters and the like recited herein.

Example 1

Isolation and Identification of the Microbes

*Bacillus megaterium* strain H491 was isolated from soil collected in Kwadaso, Ghana, Africa. *Bacillus megaterium* strains M018 and J142 were recovered from soils collected in California. The bacteria were recovered from the sample by traditional plate dilution methods as described by Lorch et al., 1995. Briefly, the sample was resuspended in sterile deionized water. Serial dilutions of the resuspended sample were prepared in sterile water. Some of these dilutions were spread onto agar plates (for example Potato Dextrose Agar) and incubated in the dark and at room temperature. After several days of incubation, colonies were recovered from the surface of the agar plate.

The isolates grew as dense, flat, cream colored colonies. The isolated bacteria are gram-positive.

Example 2

Identification of *Bacillus megaterium* Strain H491, Strain J142, and Strain M018 by Sequencing of rRNA and recA Genes The isolates (H491, J142 and M018) were identified as a *Bacillus megaterium* through 16s rRNA amplification and additional sequencing of the recA gene using universal bacterial primers (Cerritos et al., 2008).

Growth from a 24 hour potato dextrose plate was scraped with a sterile loop and resuspended in DNA extraction buffer. DNA was extracted using the MoBio Ultra Clean Microbial DNA extraction kit. DNA extract was checked for quality/quantity by electrophoresis of a 5 uL aliquot on a 1% agarose gel.

rRNA Sequences

PCR reactions for the amplification of the 16S rRNA gene were set up by combining 2 mL of the clean DNA extract with 25 mL of GoTaq Green Mastermix, 1.5 mL forward primer (27F primer; 5'-AGAGTTTGATCMTGGCTCAG-3' (SEQ ID NO:10)), 1.5 mL reverse primer (1525R primer; 5'-AAG-GAGGTGWTCCARCC-3' (SEQ ID NO:11)). The reaction volume was made up to 50 mL using sterile nuclease-free water. The PCR reaction was conducted on a thermocycler machine under the following conditions: 10 minutes at 95° C. (initial denaturing), 30 cycles of 45 seconds at 94° C., 45 seconds at 55° C. and 2 minutes at 72° C., followed by 5 minutes at 72° C. (final extension) and a final hold temperature of 10° C.

The size, quality and quantity of the PCR product was evaluated by electrophoresis of a 5 uL aliquot on a 1% agarose gel, and comparison of the product band to a mass ladder.

Excess primers, nucleotides, enzyme and template were removed from the PCR product using the MoBio PCR clean up Kit. The cleaned PCR product was subjected to direct sequencing using the primers described above.

The forward (27F, SEQ ID NO:1) and reverse sequences (1525R, SEQ ID NO:2) were aligned using the BioEdit software, and a 1451 by consensus sequence was created (see SEQ ID NO:3, infra). The 16S rRNA gene consensus sequence of strain H491 was compared to available representative bacterial 16S sequences using BLAST. For strain H491, the closest match was to *Bacillus megaterium* (GenBank accession number CP001983.1), with 99% similarity.

```
27F Sequence (SEQ ID NO: 1):
NNNNNNNNNGNNNGCTATAATGCAAGTCGAGCGAACTGATTAGAAGCTTG
CTTCTATGACGTTAGCGGCGGACGGGTGAGTAACACGTGGGCAACCTGCC
TGTAAGACTGGGATAACTTCGGGAAACCGAAGCTAATACCGGATAGGATC
TTCTCCTTCATGGGAGATGATTGAAAGATGGTTTCGGCTATCACTTACAG
ATGGGCCCGCGGTGCATTAGCTAGTTGGTGAGGTAACGGCTCACCAAGGC
AACGATGCATAGCCGACCTGAGAGGGTGATCGGCCACACTGGGACTGAGA
CACGGCCCAGACTCCTACGGGAGGCAGCAGTAGGGAATCTTCCGCAATGG
ACGAAAGTCTGACGGAGCAACGCCGCGTGAGTGATGAAGGCTTTCGGGTC
GTAAAACTCTGTTGTTAGGGAAGAACAAGTACAAGAGTAACTGCTTGTAC
CTTGACGGTACCTAACCAGAAAGCCACGGCTAACTACGTGCCAGCAGCCG
CGGTAATACGTAGGTGGCAAGCGTTATCCGGAATTATTGGGCGTAAAGCG
CGCGCAGGCGGTTTCTTAAGTCTGATGTGAAAGCCCACGGCTCAACCGTG
GAGGGTCATTGGAAACTGGGGAACTTGAGTGCAGAAGAGAAAAGCGGAAT
TCCACGTGTAGCGGTGAAATGCGTAGAGATGTGGAGGAACACCAGTGGCG
AAGGCGGCTTTTTGGTCTGTAACTGACGCTGAGGCGCGAAAGCGTGGGGA
GCAAACAGGATTAGATACCCTGGTAGTCCACGCCGTAACGATGAGTGCTA
AGTGTTAGAGGGTTTCCGCCCTTTAGTGCTGCAGCTAACGCATTAAGCAC
TCCGCCTGGGGAGTACNGGTCGCAAGACTGAAACTCAAAGGAATTGACGG
GGGCNCGCACAAGCGGTGGAGCATGTGGTTTAATTCGAAGCAACGCGAAG
AACCTTACCAGGTCTTGACATCCTCTGACAACTCTNNGATAGAGCGTTCC
CCTTNNGGGACAGAGTGACAGGTGGNGCATGGGTTGTCGTCAGCTCNTGT
CGTGAGATNNTGGGTTAAGTCCCGCAACGAGCGCAACCNTTGATCTANNN
CAGCATTCANNNGGNANTCTNNNNNGACTGCNGNTGANNACCGNAGAAAGN
TGGGGATGACNN 1525R Sequence (SEQ ID NO: 2):
NNNNNNNNNNNNNNNNNCGACTTCaCCCCAATCATCTGTCCCACCTTAGGCG
GCTAGCTCCTTACGGTTACTCCACCGACTTCGGGTGTTACAAACTCTCGT
GGTGTGACGGGCGGTGTGTACAAGGCCCGGGAACGTATTCACCGCGGCAT
GCTGATCCGCGATTACTAGCGATTCCAGCTTCATGTAGGCGAGTTGCAGC
CTACAATCCGAACTGAGAATGGTTTTATGGGATTGGCTTGACCTCGCGGT
CTTGCAGCCCTTTGTACCATCCATTGTAGCACGTGTGTAGCCCAGGTCAT
AAGGGGCATGATGATTTGACGTCATCCCCACCTTCCTCCGGTTTGTCACC
GGCAGTCACCCTTAGAGTGCCCAACTGAATGCTGGCAACTAAGATCAAGGG
TTGCGCTCGTTGCGGGACTTAACCCAACATCTCACGACACGAGCTGACGA
CAACCATGCACCACCTGTCACTCTGTCCCCCGAAGGGGAACGCTCTATCT
CTAGAGTTGTCAGAGGATGTCAAGACCTGGTAAGGTTCTTCGCGTTGCTT
```

```
-continued
CGAATTAAACCACATGCTCCACCGCTTGTGCGGGCCCCCGTCAATTCCTT

TGAGTTTCAGTCTTGCGACCGTACTCCCCAGGCGGAGTGCTTAATGCGTT

AGCTGCAGCACTAAAGGGCGGAAACCCTCTAACACTTAGCACTCATCGTT

TACGGCGTGGACTACCAGGGTATCTAATCCTGTTTGCTCCCCACGCTTTC

GCGCCTCAGCGTCAGTTACAGACCAAAAAGCCGCCTTCGCCACTGGTGTT

CCTCCACATCTCTACGCATTTCACCGCTACACGTGGAATTCCGCTTTTCT

CTTCTGCACTCAAGTTCCCCAGTTTCCAATGACCCTCCACGGTTGAGCCG

TGGGCTTTCACATCANACTTAANAAACCGCCTGCGCGCGCTTTACGCCCA

ATAATTNCNGATAACGCTTGNCACCTACGTATTACCGCGGCTGCTGGCAC

GTANNTAGCCGNGGNTTTCTGGTTAGGTACNGTCNNGGTACAAGCANNTA

CTCTNNACTNNNNTTNCNTAACANANANTTTACGACCCGAANNCNTCNTC

ACTCANGCGCNTNGCTCNNNCAGANTNTNNNNN
```

Consensus Sequence (SEQ ID NO: 3):
```
ATAATGCAAGTCGAGCGAACTGATTAGAAGCTTGCTTCTATGACGTTAGC
GGCGGACGGGTGAGTAACACGTGGGCAACCTGCCTGTAAGACTGGGATAA
CTTCGGGAAACCGAAGCTAATACCGGATAGGATCTTCTCCTTCATGGGAG
ATGATTGAAAGATGGTTTCGGCTATCACTTACAGATGGGCCCGCGGTGCA
TTAGCTAGTTGGTGAGGTAACGGCTCACCAAGGCAACGATGCATAGCCGA
CCTGAGAGGGTGATCGGCCACACTGGGACTGAGACACGGCCCAGACTCCT
ACGGGAGGCAGCAGTAGGGAATCTTCCGCAATGGACGAAAGTCTGACGGA
GCAACGCCGCGTGAGTGATGAAGGCTTTCGGGTCGTAAAACTCTGTTGTT
AGGGAAGAACAAGTACAAGAGTAACTGCTTGTACCTTGACGGTACCTAAC
CAGAAAGCCACGGCTAACTACGTGCCAGCAGCCGCGGTAATACGTAGGTG
GCAAGCGTTATCCGGAATTATTGGGCGTAAAGCGCGCGCAGGCGGTTTCT
TAAGTCTGATGTGAAAGCCCACGGCTCAACCGTGGAGGGTCATTGGAAAC
TGGGGAACTTGAGTGCAGAAGAGAAAAGCGGAATTCCACGTGTAGCGGTG
AAATGCGTAGAGATGTGGAGGAACACCAGTGGCGAAGGCGGCTTTTGGT
CTGTAACTGACGCTGAGGCGCGAAAGCGTGGGGAGCAAACAGGATTAGAT
ACCCTGGTAGTCCACGCCGTAAACGATGAGTGCTAAGTGTTAGAGGGTTT
CCGCCCTTTAGTGCTGCAGCTAACGCATTAAGCACTCCGCCTGGGGAGTA
CNGGTCGCAAGACTGAAACTCAAAGGAATTGACGGGGCCCGCACAAGCG
GTGGAGCATGTGGTTTAATTCGAAGCAACGCGAAGAACCTTACCAGGTCT
TGACATCCTCTGACAACTCTAGAGATAGAGCGTTCCCCTTCGGGGACAG
AGTGACAGGTGGTGCATGGTTGTCGTCAGCTCGTGTCGTGAGATGTTGGG
TTAAGTCCCGCAACGAGCGCAACCCTTGATCTTAGTTGCCAGCATTCAGT
TGGGCACTCTAAGGTGACTGCCGGTGACAAACCGGAGGAAGGTGGGGATG
ACGTCAAATCATCATGCCCCTTATGACCTGGGCTACACACGTGCTACAAT
GGATGGTACAAAGGGCTGCAAGACCGCGAGGTCAAGCCAATCCCATAAAA
CCATTCTCAGTTCGGATTGTAGGCTGCAACTCGCCTACATGAAGCTGGAA
TCGCTAGTAATCGCGGATCAGCATGCCGCGGTGAATACGTTCCCGGGCCT
```

```
-continued
TGTACACACCGCCCGTCACACCACGAGAGTTTGTAACACCCGAAGTCGGT
GGAGTAACCGTAAGGAGCTAGCCGCCTAAGGTGGGACAGATGATTGGGGT
G
```

For strain M018, the closest match was found to be to *Bacillus megaterium* strain PSB55 (GenBank Accession number HQ242768), with a 99% Match. Identification was performed as described for strain H491 above.

M018 FD1 Sequence
(SEQ ID NO: 4)
```
GCTATAcTGCAAGTCGAGCGAACTGATAGAAGCTTGCTTCTATGACGTTG
CGGCGGACGGGTGAGTAACACGTGGGCAACCTGCCTGTAAGACTGGGATA
ACTTCGGGAAACCGAAGCTAATACCGGATAGGATCTTCTCCTTCATGGGA
GATGATTGAAAGATGGTTTCGGCTATCACTTACAGATGGGCCCGCGGTGC
ATTAGCTAGTTGGTGAGGTAACGGCTCACCAAGGCCACGATGCATAGCCG
ACCTGAGAGGGTGATCGGCCACACTGGGACTGAGACACGGCCCAGACTCC
TACGGGAGGCAGCAGTAGGGAATCTTCCGCAATGGACGAAAGTCTGACGG
AGCAACGCCGCGTGAGTGATGAAGGCTTTCGGGTCGTAAAACTCTGTTGT
TAGGGAAGAACAAGTACAAGAGTAACTGCTTGTACCTTGACGGTACCTAA
CCAGAAAGCCACGGCTAACTACGTGCCAGCAGCCGCGGTAATACGTAGGT
GGCAAGCGTTATCCGGAATTATTGGGCGTAAAGCGCGCGCAGGCGGTTTC
TTAAGTCTGATGTGAAAGCCCACGGCTCAACCGTGGAGGGTCATTGGAAA
CTGGGGAACTTGAGTGCAGAAGAGAAAAGCGGAATTCCACGTGTAGCGGT
GAAATGCGTAGAGATGTGGAGGAACACCAGTGGCGAAGGCGGCTTTTTGG
TCTGTAACTGACGCTGAGGCGCGAAAGCGTGGGGAGCAAACAGGATTAGA
TACCCTGGTAGTCCACGCCGTAACGATGAGTGCTAAGTGTTAGAGGGTTT
CCGCCCTTTAGTGCTGCAGCTAACGCATTAAGCACTCCGCCTGGGGAGTA
CGGTCGCAAGACTGAAACTCAAAGGAATTGACGGGGCCCGCACAAGCGG
TGGAGCATGTGGTTTAATTCGAAGCAACGCGAAGAACCTTACCAGGTCTT
GACATCCTCTGACAACTCTAGAGATAGAGCGTTCCCCTTCGGGGACAGA
GTGACAGGTGGTGCATGGTTGTCGTCAGCTCGTGTCGTGAGATGTTGGG
TTAAGTCCCGCAACGAGCGCAACCCTTTGATCTTAGTTGCCAGCATTTAG
TGGGCACTCTAAGGTGACTGCCGGTGACAACGAGAAGGTGGGGATGACGT
CGAATCATCATGCCCCTTAKGACCTGGGGCTWCACAMCGKTGCYWACAAK
GGAATTGGTTAC
```

M018 RD1 Sequence (SEQ ID NO: 5):
```
TGTTACGACTTCACCCCAATCATCTGTCCCACCTTAGGCGGCTAGCTCCT
TACGGTTACTCCACCGACTTCGGGTGTTACAAACTCTCGTGGTGTGACGG
GCGGTGTGTACAAGGCCCGGGAACGTATTCACCGCGGCATGCTGATCCGC
GATTACYAGCGATTCCTGCTTCATGTAGGCKAGTTGCAGCCTACAATCCG
AACTGAGAATGGTTTTATGGGATTGGCTTGACCTCGCGGTCTTGCAGCCC
TTTGTACCATCCATTGTAGCACGTGTGTAGCCCAGGTCATAAGGGGCATG
ATGATTTGACGTCATCCCCACCTTCCTCCGGTTTGTCACCGGCAGTCACC
```

```
TTAGAGTGCCCAACTAAATGCTGGCAACTAAGATCAAGGGTTGCGCTCGT
TGCGGGACTTAACCCAACATCTCACGACACGAGCTGACGACMACCATGCA
CCACCTGTCACTCTGTCCCCCGAAGGGGAACGCTCTATCTCTAGAGTTGT
CAGAGGATGTCAAGACCTGGTAAGGTTCTTCGCGTTGCTTCGAATTAAAC
CACATGCTCCACCGCTTGTGCGGGCCCCCGTCAATTCCTTTGAGTTTCAG
TCTTGCGACCGTACTCCCCAGGCGGAGTGCTTAATGCGTTAGCTGCAGCA
CTAAAGGGCGGAAACCCTCTAACACTTAGCACTCATCGTTTACGGCGTGG
ACTACCAGGGTATCTAATCCTGTTTGCTCCCCACGCTTTCGCGCCTCAGC
GTCAGTTACAGACCAAAAAGCCGCCTTCGCCACTGGTGTTCCTCCACATC
TCTACGCATTTCACCGCTACACGTGGAATCCGCTTTTCTCTTCTGCACT
CAAGTTCCCCAGTTTCCAATGACCCTCCACGGTTGAGCCGTGGGCTTTCA
CATCAGACTTAAGAAACCGCCTGCGCGCGCTTTACGCCCAATAATTCAGA
TAACGCTCGCCACCTACGTATTACCGCGCTGCTGGCACGTAGTTAGCCGT
GGCTTTCTGGTTAGTACCGTCAGTACAGCAGTACTCTGTACTTGTTCTTC
CTAACAACAGAGTTTACGACCCGAAAGCCTTCATCATTC
```

M018 Consensus Sequence (SEQ ID NO: 6)
```
GCTATACTGCAAGTCGAGCGAACTGATAGAAGCTTGCTTCTATGACGTTG
CGGCGGACGGGTGAGTAACACGTGGGCAACCTGCCTGTAAGACTGGGATA
ACTTCGGGAAACCGAAGCTAATACCGGATAGGATCTTCTCCTTCATGGGA
GATGATTGAAAGATGGTTTCGGCTATCACTTACAGATGGGCCCGCGGTGC
ATTAGCTAGTTGGTGAGGTAACGGCTCACCAAGGCCACGATGCATAGCCG
ACCTGAGAGGGTGATCGGCCACACTGGGACTGAGACACGGCCCAGACTCC
TACGGGAGGCAGCAGTAGGGAATCTTCCGCAATGGACGAAAGTCTGACGG
AGCAACGCCGCGTGAGTGATGAAGGCTTTCGGGTCGTAAAACTCTGTTGT
TAGGGAAGAACAAGTACAAGAGTAACTGCTTGTACCTTGACGGTACCTAA
CCAGAAAGCCACGGCTAACTACGTGCCAGCAGCCGCGGTAATACGTAGGT
GGCRAGCGTTATCYGGAATTATTGGGCGTAAAGCGCGCGCAGGCGGTTTC
TTAAGTCTGATGTGAAAGCCCACGGCTCAACCGTGGAGGGTCATTGGAAA
CTGGGGAACTTGAGTGCAGAAGAGAAAAGCGGAWTTCCACGTGTAGCGGT
GAAATGCGTAGAGATGTGGAGGAACACCAGTGGCGAAGGCGGCTTTTTGG
TCTGTAACTGACGCTGAGGCGCGAAAGCGTGGGGAGCAAACAGGATTAGA
TACCCTGGTAGTCCACGCCGTAAACGATGAGTGCTAAGTGTTAGAGGGTT
TCCGCCCTTTAGTGCTGCAGCTAACGCATTAAGCACTCCGCCTGGGGAGT
ACGGTCGCAAGACTGAAACTCAAAGGAATTGACGGGGCCCGCACAAGCG
GTGGAGCATGTGGTTTAATTCGAAGCAACGCGAAGAACCTTACCAGGTCT
TGACATCCTCTGACAACTCTAGAGATAGAGCGTTCCCCTTCGGGGACAG
AGTGACAGGTGGTGCATGGTKGTCGTCAGCTCGTGTCGTGAGATGTTGGG
TTAAGTCCCGCAACGAGCGCAACCCTTGATCTTAGTTGCCAGCATTTAGT
TGGGCACTCTAAGGTGACTGCCGGTGACAAACCGGAGGAAGGTGGGGATG
ACGTCAAATCATCATGCCCCTTATGACCTGGGCTACACACGTGCTACAAT
GGATGGTACAAAGGGCTGCAAGACCGCGAGGTCAAGCCAATCCCATAAAA
CCATTCTCAGTTCGGATTGTAGGCTGCAACTMGCCTACATGAAGCAGGAA
TCGCTRGTAATCGCGGATCAGCATGCCGCGGTGAATACGTTCCCGGGCCT
TGTACACACCGCCCGTCACACCACGAGAGTTTGTAACACCCGAAGTCGGT
GGAGTAACCGTAAGGAGCTAGCCGCCTAAGGTGGGACAGATGATTGGGGT
GAAGTCGTAACA
```

For strain J142, the closest match was to *Bacillus megaterium* strain ZFJ-14. Identification was performed as described for strain H491 above.

J142 FD1 Sequence (SEQ ID NO: 7):
```
TGCTATAATGCAGTCGAGCGAACTGATTAGAAGCTTGCTTCTATGACGTT
AGCGGCGGACGGGTGAGTAACACGTGGGCAACCTGCCTGTAAGACTGGGA
TAACTTCGGGAAACCGAAGCTAATACCGGATAGGATCTTCTCCTTCATGG
GGGATGATTGAAAGATGGTTTCGGCTATCACTTACAGATGGGCCCGCGGT
GCATTAGCTAGTTGGTGAGGTAACGGCTCACCAAGGCMACGATGCATAGC
CGACCTGAGAGGGTGATCGGCCACACTGGGACTGAGACACGGCCCAGACT
CCTACGGGAGGCAGCAGTAGGGAATCTTCCGCAATGGACGAAAGTCTGAC
GGAGCAACGCCGCGTGAGTGATGAAGGCTTTCGGGTCGTAAAACTCTGTT
GTTAGGGAAGAACAAGTACRAGAGTAACTGCTTGTACCTTGACGGTACCT
AACCAGAAAGCCACGGCTAACTACGTGCCAGCAGCCGCGGTAATACGTAG
GTGGCAAGCGTTATCCGGAATTATTGGGCGTAAAGCGCGCGCAGGCGGTT
TCTTAAGTCTGATGTGAAAGCCCACGGCTCAACCGTGGAGGGTCATTGGA
AACTGGGGAACTTGAGTGCAGAAGAGAAAAGCGGAATTCCACGTGTAGCG
GTGAAATGCGTAGAGATGTGGAGGAACACCAGTGGCGAAGGCGGCTTTTT
GGTCTGTAACTGACGCTGAGGCGCGAAAGCGTGGGGAGCAAACAGGATTA
GATACCCTGGTAGTCCACGCCGTAAACGATGAGTGCTAAGTGTTAGAGGG
TTTCCGCCCTTTAGTGCTGCAGCTAACGCATTAAGCACTCCGCCTGGGGA
GTACGGTCGCAAGACTGAAACTCAAAGGAATTGACGGGGCCCGCACAAG
CGGTGGAGCATGTGGTTTAATTCGAAGCAACGCGAGAACCTTACCAGGTC
TTGACATCCTCTGACACTCTAGAGATAGAGCGTTCCCCTTCGGGGACAG
AGTGACAGTGTGCATGGTGTCGTCAGCTCGTGTCGTGAGATGTGGGTAGT
CCCGCACGAGCGCACCTGATCTAGTCAGCATTAGTGGCACTCTAGTGAC
TGCGTGACACGAGGAGGTGGGATGACGTCATCATCATGCCCCTATGACTG
GGCTACCACGTGCTACATGGATGTCAAGGCTGCAGACCGAAGTCAGCAAT
CATAAACATTCTCAGTCGAATGTAAGTCA
```

J142 RD1 Sequence (SEQ ID NO: 8):
```
CTTGTTCGACTTCCCCCAATCATCTGTCCCACCTTAGGCGGCTAGCTCCT
TACGGTTACTCCACCGACTTCGGGTGTTACAAACTCTCGTGGTGTGACGG
GCGGTGTGTACAAGGCCCGGAACGTATTCACCGCGGCATGCTGATCCGC
GATTACTAGCGATTCCAGCTTCATGTAGGCGAGTTGCAGCCTACAATCCG
AACTGAGAATGGTTTTATGGGATTGGCTTGACCTCGCGGTCTTGCAGCCC
TTTGTACCATCCATTGTAGCACGTGTGTAGCCCAGGTCATAAGGGGCATG
```

-continued
ATGATTTGACGTCATCCCCACCTTCCTCCGGTTTGTCACCGGCAGTCACC

TTAGAGTGCCCAACTAAATGCTGGCAACTAAGATCAAGGGTTGCGCTCGT

TGCGGGACTTAACCCAACATCTCACGACACGAGCTGACGACAACCATGCA

CCACCTGTCACTCTGTCCCCCGAAGGGGAACGCTCTATCTCTAGAGTTGT

CAGAGGATGTCAAGACCTGGTAAGGTTCTTCGCGTTGCTTCGAATTAAAC

CACATGCTCCACCGCTTGTGCGGGCCCCCGTCAATTCCTTTGAGTTTCAG

TCTTGCGACCGTACTCCCCAGGCGGAGTGCTTAATGCGTTAGCTGCAGCA

CTAAAGGGCGGAAACCCTCTAACACTTAGCACTCATCGTTTACGGCGTGG

ACTACCAGGGTATCTAATCCTGTTTGCTCCCCACGCTTTCGCGCCTCAGC

GTCAGTTACAGACCAAAAAGCCGCCTTCGCCACTGGTGTTCCTCCACATC

TCTACGCATTTCACCGCTACACGTGGAATTCCGCTTTTCTCTTCTGCACT

CAAGTTCCCCAGTTTCCAATGACCCTCCACGGTTGAGCCGTGGGCTTTC

ACATCAGACTTAAGAAACCGCCTGCGCGCGCTTTACGCCCAATAATTCCC

GGATAACGCTTGCCACCTACGTATTACCGCGGCTGCTGGCACGTAGTTAG

CCGTGGCTTTCTGGTTAGGTACCGTCGAGGTACAAGCAGTTACTCTCGTA

CTTGTCTTCCCTAACACAGAGTTTTACGACCCGAAGCTCATCACTCAGCG

CGTGCTCGTCGACTTCGTCATTGCGAGATCCCTACTGCTGCTTCCGTAGG

AGTCTGGACCTGTCTCAGTCAGGTGTGACGGATCACCCTCTTCAGTCGCC

TATGTGCCACTCTCGTGGGTCCCG

J142 Consensus Sequence
(SEQ ID NO: 9)
TGCTATAATGCAGTCGAGCGAACTGATTAGAAGCTTGCTTCTATGACGTT

AGCGGCGGACGGGTGAGTAACACGTGGGCAACCTGCCTGTAAGACTGGGA

TAACTTCGGGAAACCGAAGCTAATACCGGATAGGATCTTCTCCTTCATGG

GGGATGATTGAAAGATGGTTTCGGCTATCACTTACAGATGGGCCCGCGGT

GCATTAGCTAGTTGGTGAGGTAACGGCTCACCAAGGCMACGATGCATAGC

CGACCTGAGAGGGTGATCGGCCACACTGGGACTGAGACACGGCCCAGACT

CCTACGGGAGGCAGCAGTAGGGAATCTTCCGCAATGGACGAAAGTCTGAC

GGAGCAACGCCGCGTGAGTGATGAAGGCTTTCGGGTCGTAAAACTCTGTT

GTTAGGGAAGAACAAGTACGAGAGTAACTGCTTGTACCTYGACGGTACCT

AACCAGAAAGCCACGGCTAACTACGTGCCAGCAGCCGCGGTAATACGTAG

GTGGCAAGCGTTATCCGGGAATTATTGGGCGTAAAGCGCGCGCAGGCGGT

TTCTTAAGTCTGATGTGAAAGCCCCACGGCTCAACCGTGGAGGGTCATTG

GAAACTGGGAACTTGAGTGCAGAAGAGAAAAGCGGAATTCCACGTGTAG

CGGTGAAATGCGTAGAGATGTGGAGGAACACCAGTGGCGAAGGCGGCTTT

TTGGTCTGTAACTGACGCTGAGGCGCGAAAGCGTGGGGAGCAAACAGGAT

TAGATACCCTGGTAGTCCACGCCGTAAACGATGAGTGCTAAGTGTTAGAG

GGTTTCCGCCCTTTAGTGCTGCAGCTAACGCATTAAGCACTCCGCCTGGG

GAGTACGGTCGCAAGACTGAAACTCAAAGGAATTGACGGGGCCCGCACA

AGCGGTGGAGCATGTGGTTTAATTCGAAGCAACGCGAAGAACCTTACCAG

GTCTTGACATCCTCTGACAACTCTAGAGATAGAGCGTTCCCCTTCGGGG

ACAGAGTGACAGGTGGTGCATGGTTGTCGTCAGCTCGTGTCGTGAGATGT

TGGGTTAAGTCCCGCAACGAGCGCAACCCTTGATCTTAGTTGCCAGCATT

TAGTTGGGCACTCTAAGGTGACTGCCGGTGACAAACCGGAGGAAGGTGGG

GATGACGTCAAATCATCATGCCCCTTATGACCTGGGCTACACACGTGCTA

CAATGGATGGTACAAAGGGCTGCAAGACCGCGAGGTCAAGCCAATCCCAT

AAAACCATTCTCAGTTCGGATTGTAGGCTGCAACTCGCCTACATGAAGCT

GGAATCGCTAGTAATCGCGGATCAGCATGCCGCGGTGAATACGTTCCCGG

GCCTTGTACACACCGCCCGTCACACCACGAGAGTTTGTAACACCCGAAGT

CGGTGGAGTAACCGTAAGGAGCTAGCCGCCTAAGGTGGGACAGATGATTG

GGGGAAGTCGAACAAG recA Sequences

PCR reactions for the amplification of the recA gene were set up by combining 2 μL of the clean DNA extract with 25 μL of GoTaq Green Mastermix, 1.5 μL forward primer (recAf, 5'-GATCGTCARGCAGSCYTWGAT-3', SEQ ID NO:12), and 1.5 μL reverse primer (recAr, 5'-TTWCCRACCATAAC-SCCRAC-3', SEQ ID NO:13). The reaction volume was brought up to 50 μL using sterile nuclease-free water. The PCR reaction was conducted on a thermocycler machine under the following conditions: 5 minutes at 95° C. (initial denaturing), 30 cycles of 30 seconds at 95° C., 30 seconds at 45° C. and 1 minute at 72° C., followed by 5 minutes at 72° C. (final extension) and a final hold temperature of 4° C.

The size, quality and quantity of the PCR product was evaluated by running a 5 μL aliquot on a 1% agarose gel, and comparing the product band to a mass ladder.

Excess primers, nucleotides, enzyme and template were removed from the PCR product using the MoBio PCR clean up Kit. The cleaned PCR product was subjected to direct sequencing using the primers described above.

The forward and reverse sequences were aligned using the BioEdit software, and a 505 by consensus sequence was created.

The recA gene consensus sequence of each strain (H491, J142 and M018) was compared to representative bacterial sequences using BLAST. The closest species match was to the complete genome of *Bacillus megaterium* (accession number CP001982.1) with 99% similarity.

H491 recA Forward Sequence (SEQ ID NO: 14):
TGAAAGCATTTGGTAAGGTTCAATTATGAAATTAGGTGAACAAACG

GAAAAAAGAATTTCTACAATTCCAAGTGGTTCATTGGCGTTAGATATAGC

CTTAGGTGTAGGTGGATATCCACGTGGACGTGTAGTTGAAGTATATGGTC

CAGAAAGCTCAGGTAAAACAACAGTTGCTCTTCATGCGATTGCAGAAGTT

CAACAGCAGGGCGGACAGGCTGCATTTATCGATGCGGAGCACGCGTTAGA

TCCTGTATATGCTCAAAAATTAGGTGTGAATATTGATGAGCTATTATTAT

CTCAGCCTGATACGGGAGAACAAGCTTTAGAAATCGCTGAAGCTTTAGTT

CGAAGCGGTGCAGTAGATATTATCGTTGTTGACTCAGTAGCAGCATTAGT

GCCAAAAGCGGAAATTGAAGGAGAAATGGGAGACTCTCACGTGGGTCTAC

AAGCTCGTTTAATGTCTCAAGCATTGCGTAAACTATCTGGAGCTATCAAT

AAGTCTAAAACAATCGCTATCTTTATTAACCAAATTCGTGAAAAAGTCGG

CGTTnGGGTCGGAAAA

H491 recA reverse Sequence (SEQ ID NO: 15):
GWAGCGATTGTTTTAGACTTATTGATAGCTCCAGATAGTTTACGCA
ATGCTTGAGACATTAAACKAGCTTGTAGACCCACGTGAGAGTCTCCCATT
TCTCCTTCAATTTCCGCTTTTGGCACTAATGCTGCTACTGAGTCAACAAC
GATAATATCTACTGCACCGCTTCGAACTAAAGCTTCAGCGATTTCTAAAG
CTTGTTCTCCCGTATCAGGCTGAGATAATAATAGCTCATCAATATTCACA
CCTAATTTTTGAGCATATACAGGATCTAACGCGTGCTCCGCATCGATAAA
TGCAGCCTGTCCGCCCTGCTGTTGAACTTCTGCAATCGCATGAAGAGCAA
CTGTTGTTTTACCTGAGCTTTCTGGACCATATACTTCAACTACACGTCCA
CGTGGATATCCACCTACACCTAAGGCTATATCTAACGCCAATGAACCACT
TGGAATTGTAGAAATTCTTTTTTCCGTTTGTTCACCTAATTTCATAATTG
AACCTTTACCAAATTGCTTTTCAATTTGTTTTAAAGCCATATCWAAGCCT
GCWWWGACGATC H491 Consensus Sequence (SEQ ID NO: 16):
AAGGTTCAATTATGAAATTAGGTGAACAAACGGAAAAAAGAATTTC
TACAATTCCAAGTGGTTCATTGGCGTTAGATATAGCCTTAGGTGTAGGTG
GATATCCACGTGGACGTGTAGTTGAAGTATATGGTCCAGAAAGCTCAGGT
AAAACAACAGTTGCTCTTCATGCGATTGCAGAAGTTCAACAGCAGGGCGG
ACAGGCTGCATTTATCGATGCGGAGCACGCGTTAGATCCTGTATATGCTC
AAAAATTAGGTGTGAATATTGATGAGCTATTATTATCTCAGCCTGATACG
GGAGAACAAGCTTTAGAAATCGCTGAAGCTTTAGTTCGAAGCGGTGCAGT
AGATATTATCGTTGTTGACTCAGTAGCAGCATTAGTGCCAAAAGCGGAAA
TTGAAGGAGAAATGGGAGACTCTCACGTGGGTCTACAAGCTCGTTTAATG
TCTCAAGCATTGCGTAAACTATCTGGAGCTATCAATAAGTCTAAAACAAT
CGCT

M018: recA Gene Sequencing

M018 recA forward Sequence (SEQ ID NO: 17):
TTGAAGCATTTGGTAAAGGTTCAATTATGAAATTAGGTGAACAAAC
GGAAAAAAGAATTTCTACAATTCCAAGTGGTTCATTAGCGTTAGATATAG
CTTTAGGTGTAGGTGGATATCCACGTGGACGCGTAGTTGAAGTATATGGT
CCAGAAAGCTCAGGTAAAACAACAGTTGCTCTTCATGCGATTGCAGAAGT
TCAACAGCAGGGCGGACAGGCTGCATTTATCGATGCGGAGCACGCGTTAG
ATCCTGTATATGCTCAAAAATTAGGTGTGAATATTGATGAGCTATTATTA
TCTCAGCCTGATACGGGAGAACAAGCTTTAGAAATCGCTGAAGCTTTAGT
TCGAAGCGGTGCAGTAGATATTATCGTTGTTGACTCAGTAGCAGCATTAG
TGCCAAAAGCGGAAATTGAAGGAGAAATGGGAGACTCTCACGTGGGTCTA
CAAGCTCGTTTAATGTCTCAAGCATTGCGTAAACTATCTGGAGCTATCAA
CAAGTCTAAAACAATCGCTATCTTTATTAACCAAATTCGTGAAAAGTCG
GCGTTnGGGTTCGGAAAA M018 recA reverse Sequence (SEQ ID NO: 18):
GGTATAAAGATAGGCGATTGTTTTAGACTTGTTGATAGCTCCAGAT
AGTTTACGCAATGCTTGAGACATTAAAcgAGCTTGTAGACCCACGTGAGA
GTCTCCCATTTCTCCTTCAATTTCCGCTTTTGGCACTAATGCTGCTACTG
AGTCAACAACGATAATATCTACTGCACCGCTTCGAACTAAAGCTTCAGCG
ATTTCTAAAGCTTGTTCTCCCGTATCAGGCTGAGATAATAATAGCTCATC
AATATTCACACCTAATTTTTGAGCATATACAGGATCTAACGCGTGCTCCG
CATCGATAAATGCAGCCTGTCCGCCCTGCTGTTGAACTTCTGCAATCGCA
TGAAGAGCAACTGTTGTTTTACCTGAGCTTTCTGGACCATATACTTCAAC
TACGCGTCCACGTGGATATCCACCTACACCTAAAGCTATATCTAACGCTA
ATGAACCACTTGGAATTGTAGAAATTCTTTTTTCCGTTTGTTCACCTAAT
TTCATAATTGAACCTTTACCAAATTGCTTTTCAATTTGTTTTAAAGCCAT
ATCWAAGCCTAAWWRGACGATCYA Consensus Sequence (SEQ ID NO: 19):
AAGGTTCAATTATGAAATTAGGTGAACAAACGGAAAAAAGAATTTC
TACAATTCCAAGTGGTTCATTAGCGTTAGATATAGCTTTAGGTGTAGGTG
GATATCCACGTGGACGCGTAGTTGAAGTATATGGTCCAGAAAGCTCAGGT
AAAACAACAGTTGCTCTTCATGCGATTGCAGAAGTTCAACAGCAGGGCGG
ACAGGCTGCATTTATCGATGCGGAGCACGCGTTAGATCCTGTATATGCTC
AAAAATTAGGTGTGAATATTGATGAGCTATTATTATCTCAGCCTGATACG
GGAGAACAAGCTTTAGAAATCGCTGAAGCTTTAGTTCGAAGCGGTGCAGT
AGATATTATCGTTGTTGACTCAGTAGCAGCATTAGTGCCAAAAGCGGAAA
TTGAAGGAGAAATGGGAGACTCTCACGTGGGTCTACAAGCTCGTTTAATG
TCTCAAGCATTGCGTAAACTATCTGGAGCTATCAACAAGTCTAAAACAAT
CG

J142: recA Gene Sequencing

J142 recA Forward Sequence (SEQ ID NO: 20):
GAAAGCATTTGGTAAGGTTCAATTATGAAATTAGGTGAACAAACGG
AAAAAAGAATTTCTACAATTCCAAGTGGTTCATTAGCGTTAGATATAGCC
TTAGGTGTAGGTGGATATCCACGTGGACGTGTAGTTGAAGTATATGGTCC
AGAAAGCTCAGGTAAAACAACAGTTGCTCTTCATGCGATTGCAGAAGTTC
AACAGCAGGGCGGACAGGCTGCATTTATCGATGCGGAGCACGCGTTAGAT
CCTGTATATGCTCAAAAATTAGGTGTGAATATTGATGAGCTATTATTATC
TCAGCCTGATACGGGAGAACAAGCTTTAGAAATCGCTGAAGCTTTAGTTC
GAAGCGGTGCAGTAGATATTATCGTTGTTGACTCAGTAGCAGCATTAGTG
CCAAAAGCGGAAATTGAAGGAGAAATGGGAGACTCTCACGTGGGTCTACA
AGCTCGTTTAATGTCTCAAGCATTGCGTAAACTATCTGGAGCTATCAATA
AGTCTAAAACAATCGCTATCTTTATTAACCAAATTCGTGAAAAGTCGGC
GTTnGGGTCGGAAAA -continued J142 recA Reverse Sequence (SEQ ID NO: 21):
AGCGATTGTTTTAGACTTATTGATAGCTCCAGATAGTTTACGCAAT

GCTTGAGACATTAAACGAGCTTGTAGACCCACGTGAGAGTCTCCCATTTC

TCCTTCAATTTCCGCTTTTGGCACTAATGCTGCTACTGAGTCAACAACGA

TAATATCTACTGCACCGCTTCGAACTAAAGCTTCAGCGATTTCTAAAGCT

TGTTCTCCCGTATCAGGCTGAGATAATAATAGCTCATCAATATTCACACC

TAATTTTTGAGCATATACAGGATCTAACGCGTGCTCCGCATCGATAAATG

CAGCCTGTCCGCCCTGCTGTTGAACTTCTGCAATCGCATGAAGAGCAACT

GTTGTTTTACCTGAGCTTTCTGGACCATATACTTCAACTACACGTCCACG

TGGATATCCACCTACACCTAAGGCTATATCTAACGCTAATGAACCACTTG

GAATTGTAGAAATTCTTTTTTCCGTTTGTTCACCTAATTTCATAATTGAA

CCTTTACCAAATTGCTTTTCAATTTGTTTTAAAGCCATATCAAAGCCTGC

TRAACRATCAA

Consensus Sequence (SEQ ID NO: 22):
AAGGTTCAATTATGAAATTAGGTGAACAAACGGAAAAAAGAATTTC

TACAATTCCAAGTGGTTCATTAGCGTTAGATATAGCCTTAGGTGTAGGTG

GATATCCACGTGGACGTGTAGTTGAAGTATATGGTCCAGAAAGCTCAGGT

AAAACAACAGTTGCTCTTCATGCGATTGCAGAAGTTCAACAGCAGGGCGG

ACAGGCTGCATTTATCGATGCGGAGCACGCGTTAGATCCTGTATATGCTC

AAAAATTAGGTGTGAATATTGATGAGCTATTATTATCTCAGCCTGATACG

GGAGAACAAGCTTTAGAAATCGCTGAAGCTTTAGTTCGAAGCGGTGCAGT

AGATATTATCGTTGTTGACTCAGTAGCAGCATTAGTGCCAAAAGCGGAAA

TTGAAGGAGAAATGGGAGACTCTCACGTGGGTCTACAAGCTCGTTTAATG

TCTCAAGCATTGCGTAAACTATCTGGAGCTATCAATAAGTCTAAAACAAT

CGCT

All isolates were 99-100% match to *Bacillus megaterium* DSM319, as well as other strains of *Bacillus megaterium*. These results confirm the identity of the three isolates as *Bacillus megaterium*.

Example 3

Biochemical Characterization of *B. Megaterium* H491

*Bacillus megaterium* strain H491 was determined to be gram positive, urease positive, catalase positive, oxidase negative and lipase positive. Extensive biochemical characterization of the isolate was performed using Biolog Phenotypic Microarrays. The full Biolog Phenotypic microarray consists of twenty 96-well plates, each well containing a different carbon, nitrogen, phosphorus or other nutrient source. Some of the plates also contain different antibiotics, metals, etc., to evaluate susceptibility of the isolate. Absorbance readings from the wells in each plate were compared to a negative control well. Absorbance readings above the negative control threshold indicated growth of the isolate under the conditions in a particular well, while reading at or below the negative control indicated that the isolate failed to thrive under the specific conditions of that well. The test was performed for H491 at 25° C., with duplicate plates for each phenotype test.

*B. megaterium* strain H491 was able to utilize the following carbohydrates, organic acids and peptides as carbon sources: L-Arabinose, N-Acetyl-D-Glucosamine, D-Galactose, L-Aspartic acid, L-Proline, D-Trehalose, Dulcitol, Glycerol, D-Glucuronic acid, D-Gluconic acid, D-Xylose, L-Lactic acid, D-Mannitol, L-Glutamic acid, D-Glucose-6-Phosphate, D-Galactonic acid-g-Lactone, D,L-Malic acid, D-Ribose, D-Fructose, a-D-Glucose, Maltose, D-Melibiose, Thymidine, L-Asparagine, D-Aspartic acid, a-Ketoglutaric acid, Sucrose, L-Glutamine, Maltotriose, Citric acid, Fumaric acid, Bromosuccinic acid, L-Alanine, Ala-Gly, Methylpyruvate, L-Malic acid, L-Lyxose, Pyruvic acid, Dextrin, Glycogen, D-Arabinose, Arbutin, 2-Deoxy-D-Ribose, 3-O-b-D-Galactopyranosyl-D-Arabinose, Gentiobiose, Palatinose, D-Raffinose, Salicin, Stachyose, D-Tagatose, Turanose, g-Amino-N-Butyric acid, D-Glucosamine, b-Hydroxybutyric acid, 5-Keto-D-Gluconic acid, Quinic acid, D-Tartaric acid, L-Tartaric acid, L-Ornithine, L-Pyroglutamic acid, and Dihydroxyacetone.

The following substrates were not utilized as carbon sources, as evidenced by absorbance readings below the negative control threshold: D-Saccharic acid, D-Serine, D-Sorbitol, L-Fucose, D,L-a-Glycerol Phosphate, L-Rhamnose, D-Glucosaminic acid, 1,2-Propanediol, a-Ketobutyric acid, a-D-Lactose, D-Glucose-1-Phosphate, a-Hydroxyglutaric acid-g-Lactone, a-Hydroxybutyric acid, Adonitol, 2'-Deoxyadenosine, Adenosine, D-Threonine, Propionic acid, Mucic acid, Glycolic acid, Tricarballylic acid, L-Threonine, N-Acetyl-D-Mannosamine, D-Malic acid, Gly-Pro, L-Galactonic acid-g-Lactone, Chondroitin Sulfate C, a-Cyclodextrin, Inulin, Laminarin, Mannan, N-Acetyl-D-Galactosamine, N-Acetyl-Neuraminic acid, b-D-Allose, Amygdalin, D-Arabitol, L-Arabitol, i-Erythritol, D-Fucose, L-Glucose, D-Lactitol, b-Methyl-D-Galactoside, 3-Methylglucose, b-Methyl-D-Glucuronic acid, a-Methyl-D-Mannoside, Sedoheptulosan, L-Sorbose, Xylitol, N-Acetyl-D-Glucosaminitol, d-Amino Valeric acid, Capric acid, Caproic acid, Citraconic acid, Citramalic acid, 2-Hydroxybenzoic acid, 4-Hydroxybenzoic acid, a-Keto-Valeric acid, Itaconic acid, D-Lactic acid Methyl Ester, Malonic acid, Melibionic acid, Oxalic acid, D-Ribono-1,4-Lactone, Sebacic acid, Sorbic acid, Succinamic acid, Acetamide, L-Alaninamide, N-Acetyl-L-Glutamic acid, Glycine, L-Homoserine, Hydroxy-L-Proline, L-Isoleucine, L-Leucine, L-Lysine, L-Phenylalanine, L-Valine, D,L-Carnitine, sec-Butylamine, D,L-Octopamine, 2,3-Butanediol, 2,3-Butanedione, and 3-Hydroxy-2-butanone.

H491 was able to utilize the following amino acids as nitrogen sources: L-Glutamine, L-Pyroglutamic acid, L-Glutamic acid, L-Asparagine, L-Ornithine, D-Asparagine, L-Proline, L-Aspartic acid, D-Alanine, L-Arginine, L-Alanine, L-Serine, D-Aspartic acid, L-Tryptophan, and L-Tyrosine. It was also able to utilize Urea, Putrescine, Agmatine, N-Acetyl-D-Glucosamine, Cytidine, Guanosine, Inosine, Xanthine, Uric acid, Allantoin, g-Amino-N-Butyric acid and a-Amino-N-Valeric acid as additional organic nitrogen sources. H491 could also utilize ammonia, nitrite and nitrate as inorganic nitrogen sources.

H491 was able to utilize a variety of substrates as phosphorous sources, including Phosphate, Thiophosphate, Dithiophosphate, D-Glucosamine-6-Phosphate, Cysteamine-S-Phosphate, Uridine 2',3'-Cyclic Monophosphate, and Thymidine 5'-Monophosphate.

Metabolism of H491 was inhibited below pH 5, but restored at pH 4.5 in the presence of L-arginine, L-methionine and 5-hydroxy-lysine. Growth was observed between pH 5 to pH 10. The strain did not tolerate NaCl above 5%, and only slight growth was detected at 4% NaCl. The Bergey's Manual of Systematic Bacteriology indicates that *Bacillus megaterium* isolates can use citrate as a sole carbon source; most can grow at 7% NaCl, but none at 10% NaCl; and most strain do not reduce nitrate. In contrast, H491 did not tolerate NaCl above 5%, and was able to utilize both nitrate and nitrite as nitrogen sources.

Example 4

Production of *B. Megaterium* H491, M018 and J142 by Fermentation

A supernatant with nematicidal activity was produced through the submerged fermentation of strain H491 under aerobic conditions in liquid V8 medium. Other suitable media include tryptic soy broth, or any nutrient medium containing appropriate carbon and nitrogen sources.

A seed plate was started by streaking a fresh potato dextrose agar plate with a small amount of strain H491, using a sterile loop. The plate was incubated at 25° C. for 2-3 days or until enough biomass was evident on the surface of the plate.

A 50 mL V8 medium seed flask was inoculated with one loopful of material collected from the agar plate surface. The seed was incubated in a shaker at 200 rpm for 2 days.

A glass 2.8 L, non-baffled fernbach flask containing 500 mL of V8 medium was aseptically inoculated with 2% of seed. The fermentation was allowed to proceed at 25° C. for 5 days with constant agitation at 150-200 rpm.

The supernatant was obtained by separation the cells from the spent fermentation broth by centrifugation, or other means of separation. Activity of the supernatant was verified by means of the bioassay described below.

Example 5

Further Characterization of *B. Megaterium* H491, J142 and M018

Resistance to Antibiotics

Antibiotic susceptibility of *Bacillus megaterium* strains H491, J142 and M018 was tested using antibiotic disks on Muller-Hinton medium as described in PML Microbiological's technical data sheet #535. Results obtained after 48-hour incubation at 25° C. are presented in Table 1.

TABLE 1

Susceptibility of *Bacillus megaterium* H491, J142 and M018 to various antibiotics. Susceptibility degree is indicated by +++ (very), ++ (somewhat), + (marginally), and resistance is indicated by (−).

|  | Concentration (mg) | H491 | J142 | M018 |
|---|---|---|---|---|
| Tetracycline | 30 | +++ | +++ | +++ |
| Kanamycin | 30 | +++ | +++ | +++ |
| Erythromycin | 15 | +++ | +++ | +++ |
| Streptomycin | 10 | +++ | +++ | + |
| Penicillin | 10 | +++ | − | ++ |
| Ampicillin | 10 | +++ | +++ | ++ |
| Oxytetracycline | 30 | +++ | +++ | +++ |
| Chloramphenicol | 30 | +++ | +++ | ++ |
| Ciprofloxacin | 5 | +++ | +++ | +++ |
| Gentamicin | 10 | +++ | +++ | +++ |
| Piperacillin | 100 | +++ | + | ++ |
| Cefuroxime | 30 | +++ | +++ | +++ |
| Imipenem | 10 | +++ | +++ | +++ |
| Sulphamethoxazole-Trimethoprim | 23.75/25 | +++ | +++ | +++ |

Chemical Sensitivity

Chemical sensitivity data was obtained from the Biolog Phenotypic Microarray. H491 was found to be susceptible to the following compounds: Chlortetracycline, Lincomycin, Amoxicillin, Cloxacillin, Minocycline, Capreomycin, Demeclocycline, Nafcillin, Cefazolin, Enoxacin, Nalidixic acid, Chloramphenicol, Erythromycin, Neomycin, Cephalothin, Kanamycin, Penicillin G, Tetracycline, Carbenicillin, Oxacillin, Penimepicycline, Paromomycin, Vancomycin, Sisomicin, Novobiocin, 2,4-Diamino-6,7-diisopropylpteridine, Sulfadiazine, Benzethonium Chloride, Tobramycin, Sulfathiazole, 5-Fluoroorotic acid, Sulfamethoxazole, L-Aspartic-b-hydroxamate, Spiramycin, Rifampicin, Dodecyltrimethyl ammonium bromide, Azlocillin, 2,2'-Dipyridyl, 6-Mercaptopurine monohydrate, Doxycycline, Potassium chromate, Cefuroxime, 5-Fluorouracil, Rolitetracycline, Cesium chloride, Thallium (I) acetate, Cobalt (II) chloride, Trifluoperazine, Tylosin, Acriflavine, Furaltadone, Sanguinarine chloride, Fusaric acid, Boric acid, 1-Hydroxypyridine-2-thione (pyrithione), Sodium Cyanate, Cadmium chloride, Iodoacetic acid, Sodium Dichromate, Cefoxitin, Sodium metaborate, Chloramphenicol, Sodium metavanadate, Chelerythrine chloride, Carbenicillin, Sodium Nitrite, Ethylene Glycol-bis(b-Aminoethyl ether)-N,N,N',N'-Tetraacetic Acid, Promethazine, Sodium orthovanadate, Guanidine hydrochloride, D-Cycloserine, EDTA, 5,7-Dichloro-8-hydroxyquinaldine, 5,7-Dichloro-8-hydroxyquinoline, Fusidic acid, sodium salt, 1,10-Phenanthroline Monohydrate, Phleomycin, Domiphen bromide, Alexidine, 5-Nitro-2-furaldehyde semicarbazone (Nitrofurazone), Methyl viologen, Oleandomycin, phosphate salt, Puromycin, Carbonyl-cyanide m-chlorophenylhydrazone (CCCP), Sodium Azide, Menadione, sodium bisulfite, 2-Nitroimidazole, Hydroxyurea, 5-Chloro-7-iodo-8-hydroxy-quinoline, Sulfanilamide, Trimethoprim, Dichlofluanid, Protamine sulfate, Chlorodinitrobenzene, Diamide, Cinoxacin, Streptomycin, Rifamycin SV, Potassium tellurite, Sodium Selenite, Glycine hydroxamate, 4-Chloro-3,5-dimethyl-phenol, D-Serine, Thiosalicylate, Salicylate, sodium, Sulfachloropyridazine, Oxycarboxin, 3-Amino-1,2,4-triazole, Chlorpromazine, Niaproof, Compound 48/80, Sodium Tungstate, Lithium chloride, Chlorambucil, Cefamandole nafate, Cefsulodin, Caffeine, Ketoprofen, Thiamphenicol, Trifluorothymidine, Poly-L-lysine, Pentachlorophenol, Sodium Arsenite, Lidocaine, Sodium periodate, Antimony (III) chloride, Semicarbazide hydrochloride, Tinidazole, 5-Fluoro-5'-deoxyuridine, 2-Phenylphenol, Plumbagin, Josamycin, Gallic acid, Methyltrioctylammonium chloride, 2,4-Dintrophenol, Chlorhexidine diacetate, trans-Cinnamic acid, Tetraethylthiuram disulfide, FCCP, D,L-Thioctic acid, Phenethicilllin, Sodium Caprylate, Lauryl sulfobetaine (N-Dodecyl-N,N-dimethyl-3-ammonio-1-propane-sulfonate), Hexamine cobalt (III) chloride, Polymyxin B, Amitriptyline, Apramycin, Orphenadrine, D,L-Propanolol, Tetrazolium violet, Thioridazine, Atropine, Ornidazole, Proflavine, 18-Crown-6 ether, Crystal violet, Dodine (n-Dodecylguanidine), Hexachlorophene, 4-Hydroxycoumarin, Oxytetracycline, Pridinol, Captan, 3,5-Dinitrobenzoic acid, 8-Hydroxyquinoline, Patulin, Tolylfluanid, and Troleandomycin.

Resistance was observed in wells containing the following compounds with known antibacterial activity (at a maximum concentration of 4 ug): amikacin, lomefloxacin, bleomycin, colistin, gentamicin, ofloxacin, polymixin B, sulfamethazine, spectinomycin, ampicillin and oxolinic acid.

Example 6

Fatty Acid Composition

After incubation for 24 hours at 28° C., a loopful of well-grown cells were harvested and fatty acid methyl esters were prepared, separated and identified using the Sherlock Microbial Identification System (MIDI) as described (see Vandamme et al., 1992). The predominant fatty acids present in the *Bacillus megaterium* strains are shown in Table 2.

TABLE 2

Fatty Acid Methyl Ester (FAME) composition (%) of the different *Bacillus megaterium* strains with nematicidal activity.

| FAME | M018 | J142 | H491 |
|---|---|---|---|
| 14:0i | 4.77 | 6.05 | 6.36 |
| 14:0 | 1.33 | 1.65 | 1.52 |
| 15:0i | 41.89 | 32.97 | 32.03 |
| 15:0ai | 36.7 | 42.93 | 44.41 |
| 16:01ω7cOH | 1.32 | 1.39 | 1.03 |
| 16:0i | 0.97 | 1.41 | 2.11 |
| 16:1ω11c | 3.56 | 4.03 | 3.16 |
| 16:0 | 2.06 | 2.96 | 3.47 |
| 17:1iω10c | 1.38 | 0.56 | 1.95 |
| Sum in 4 | 1.08 | 0.71 | 3.97 |
| 17:0i | 2.22 | 1.89 | 1.95 |
| 17:0ai | 2.73 | 3.43 | 3.97 |
| Similarity index to *B. megaterium* | 0.949 | 0.948 | 0.991 |

Similarity indices of the FAME profiles to the database were all within the species confidence threshold (0.948-0.991). A dendogram was built by cluster analysis techniques to produce unweighted pair matching based on fatty acid compositions. The results indicate that H491 (listed as MBI-303) is most similar to J142, and that M018 is more different from the other two strains.

Example 7

MALDI-TOF Identification of Isolates H491, M018 and J142

Samples were submitted for MALDI-TOF (Matrix Assisted Laser Desorption/Ionization-Time of Flight) spectrometry profiling and identification to MIDI Labs, Inc (Newark, Del.) to create a profile from the ribosomal proteins of the isolates. The profile was compared to a proprietary database, and the isolates were identified based on their MALDI-TOF scores.

MALDI-TOF scores above 2.000 provide identification confidence to the species level, scores from 1.700-1.999 to the genus level, and scores below 1.700 indicate no match in the database. Both H491 and M018 yielded MALDI-TOF scores above 2.000 (2.163 and 2.291 respectively), while J142 had a score of 1.972. These results indicate that the ribosomal protein profile of J142 may be unique within the *Bacillus megaterium* species.

Example 8

Efficacy of *Bacillus megaterium* Isolates Against Root-Knot Nematodes (*Meloidogyne incognita*)-Agar Assays A: Water-Agar-Assay#1

To determine and compare the effects of different *Bacillus megaterium* strains on root-knot nematodes (*Meloidogyne incognita* VW6), a water-agar-assay was conducted. Seven-day-old 'White Wonder' cucumber seedlings were transferred on water agar in 60-mm-diameter petri dishes at a rate of one seeding/plate. Cucumbers were then treated with 300 ml of *B. megaterium* H491 fermentation supernatant and 700 *M. incognita*/plate, with six replications of each treatment. After incubation for 11 days, the number of galls in cucumber roots was recorded. The results, shown in Table 3, indicate that all strains significantly reduced the number of galls in cucumber roots compared with the water control.

TABLE 3

Effects of *Bacillus megaterium* isolates' fermentation supernatant on root-knot gall formation in cucumber roots

| Treatment | Gall Number | % Gall Reduction |
|---|---|---|
| H491 | 3.3 ± 1.4 | 66.7 ± 13.7 |
| J142 | 3.7 ± 1.2 | 63.3 ± 12.1 |
| M018 | 5.8 ± 1.5 | 41.7 ± 14.7 |
| Avid (1%) | 1 ± 0.5 | 95 ± 5.5 |
| Media Blank | 7 ± 1.2 | 33.3 ± 12.1 |
| Water | 10 ± 2.6 | 0 ± 26 |

B: Agar Seedling Assay #2: Effect of *B. Megaterium* H491 on *M. Incognita* Infestation on Cucumber To assess the effect of the top supernatant of *B. megaterium* H491 on juveniles (J2s) of root-knot nematodes (*Meloidogyne incognita* VW6), the following test was conducted on 60 mm-diameter petri dishes:

Seeds of cucumber cv. 'White Wonder' were germinated on wet tissue paper in petri dishes at room temperature. A week later, germinated seedlings were transferred to water agar in petri dishes at the rate of one seedling/dish. A 300-ml aliquot of *B. megaterium*. H491 fermentation supernatant was added into each dish, after which 300 *M. incognita* J2s were added in 150 ml of deionized water. Petri dishes were then covered and incubated at 25° C. for 7 days. Water, media blank and Avid (0.1%) were used as negative, negative, and positive controls, respectively. The effect of each substance on nematode survival was assessed after 7 days by counting the number of galls in cucumber roots, and expressed as a percentage of the water control. Experiments were conducted in duplicate.

Figure 9:
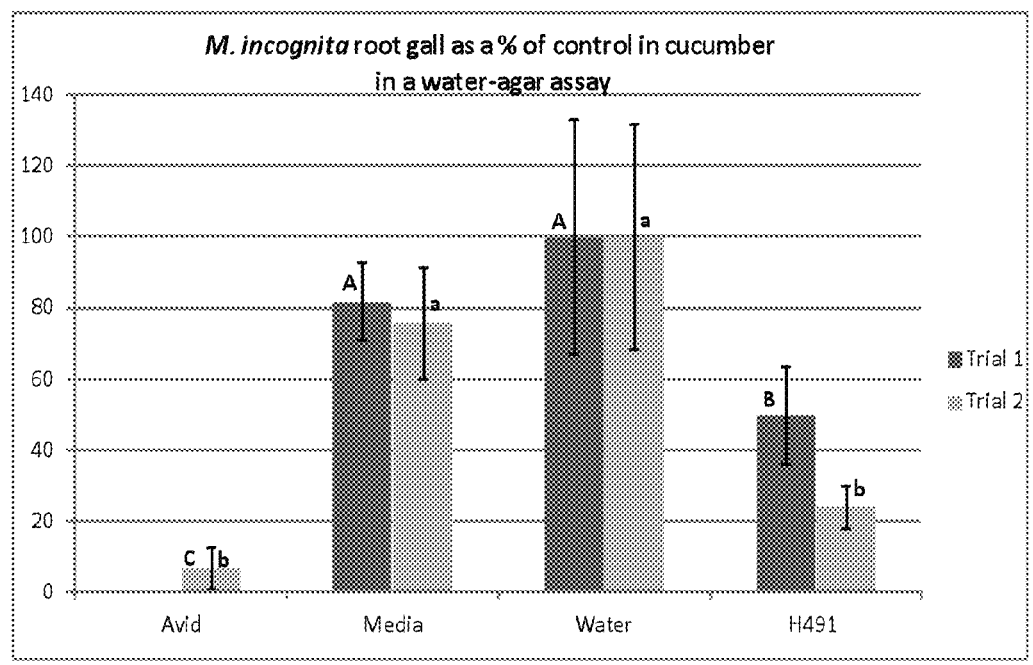
FIG. 9 shows the effects of H491 supernatant on *M. incognita* in cucumber in a water-agar-assay.

The results, presented in FIG. 9, show that *B. megaterium* H491 supernatant significantly reduced the number of galls in cucumber roots compared with the water control in both trials, which indicated that H491 was effective against *M. incognita* and can be used for management of this nematode in cucumber.

Example 9

In Vitro Assays with *M. Incognita* and *M. Hapla*

A: In Vitro Nematicidal Bioassay Against *M. Incognita* and *M. Hapla*

Figure 5:
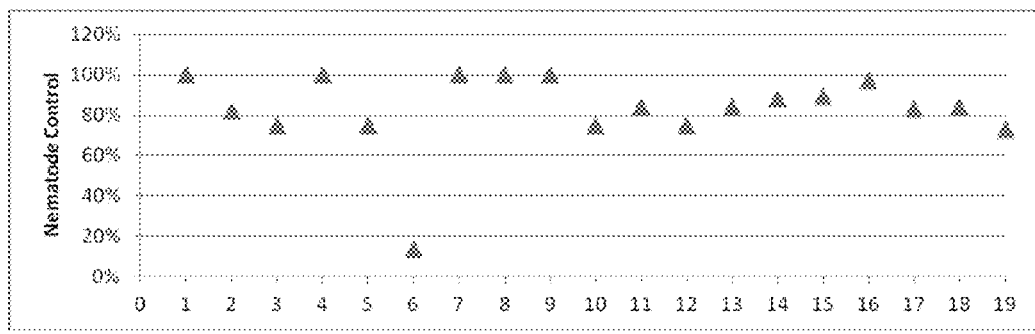
FIG. 5 depicts the average nematicidal activity of each batch for each fermentation numbered 1-19 in chronological order.

In order to ensure consistent and adequate control of nematodes in all filter sterilized *B. megaterium* H491 fermentations, the motility of root-knot nematode juveniles (J2's) was measured in an in vitro 96-well plastic cell-culture plate bioassay. This procedure is based on a visual grading of motility of the nematodes in each well treated with H491 where each treatment is tested in well repetitions of four: 100 ml of each microbial sample solution was dispensed into its corresponding well followed by 30 ml of a 1:100 dilution of plant preservative material (PPM) solution that momentarily suppresses microbial growth and allows visibility in each well. Finally, 50 ml of nematode solution, containing approximately 15 J2's, was added. The plate was covered and incubated for 24 hours at 25° C., then the effect of each sample was visually scored and recorded. Nematicidal activity was confirmed in 19 different small scale fermentations, with nematicidal activity usually hovering over 60%, as summarized in FIG. 5.

B: Nematode (*M. Hapla*) Recovery after Exposure to H491 Supernatant

To assess the effect of H491 supernatant on the motility and subsequent recovery of juveniles of root-knot nematodes (*Meloidogyne hapla*), the following test was conducted on 96-well plastic cell-culture plates. A 50-ml aliquot of each test solution was added into appropriate wells after which, 50 J2s dispensed in 30 ml of deionized water were added into each well. The plate was closed with a lid, and incubated at 25° C. for 72 hours. Water and Avid® nematicide (1%) were used as negative and positive controls, respectively. The effect of each substance on nematode motility was determined after 24, 48, and 72 hours by adding a drop of 1 N NaOH into each well, and the proportion of motile nematodes in each treatment was recorded as a percentage of the initial number. To assess the recovery of motility in each treatment, a volume of 70 ml was removed from each well, and the remaining solution in each well was diluted by adding 100 ml of deionized water. Plates were again incubated for 24 hours as described above, after which the second motility evaluation was performed. There were three replications for each treatment and the study was conducted twice.

Results are shown in Table 4. After 48 hours, wells containing nematodes exposed to the highest amount of treatment solution were too cloudy to read without washing off the treatments. Therefore, percent of motile nematodes were not recorded directly after 48 or 72 hours. Percent of motile nematodes exposed to H491 supernatant was found to decrease with increased time of incubation. The lowest rate (17.5%) was observed 72 hours after incubation. These results indicate that H491 supernatant can immobilize juveniles of root-knot nematodes, and this effect can last for at least 72 hours.

TABLE 4

Percent recovery rate of *Meloidogyne hapla* after 24, 48, and 72 hours of incubation with H491 supernatant.

| Candidate | Treatment* | | | |
|---|---|---|---|---|
| | 24 | 24-24 | 48-24 | 72-24 |
| Water | 95 ± 3.2 | 97.5 ± 2.7 | 95 ± 4.5 | 90 ± 4.5 |
| Media | 78.3 ± 2.6 | 82.5 ± 2.7 | 82.5 ± 2.7 | 80 ± 4.5 |
| Avid (1%) | 10 ± 4.5 | 13.3 ± 2.6 | 11.7 ± 2.6 | 10 ± 4.5 |
| H491 | 38 ± 2.7 | 35 ± 4.5 | 25 ± 5.5 | 17.5 ± 2.7 |

Data shown are mean values obtained from two studies.
*"24"indicates that observation was conducted directly 24 h after incubation of nematodes with the candidates; "24-24" indicates observation after incubation with candidates for 24 h and then 24 h in water; "48-24"indicates that observation was conducted after incubation with candidates for 48 h and then 24 h in water; 72-24indicates that observation was conducted after incubation with candidates for 72 h and then 24 h in water Example 10

In Vitro Dose-Response Assay Against Free-Living Nematodes

Figure 6:
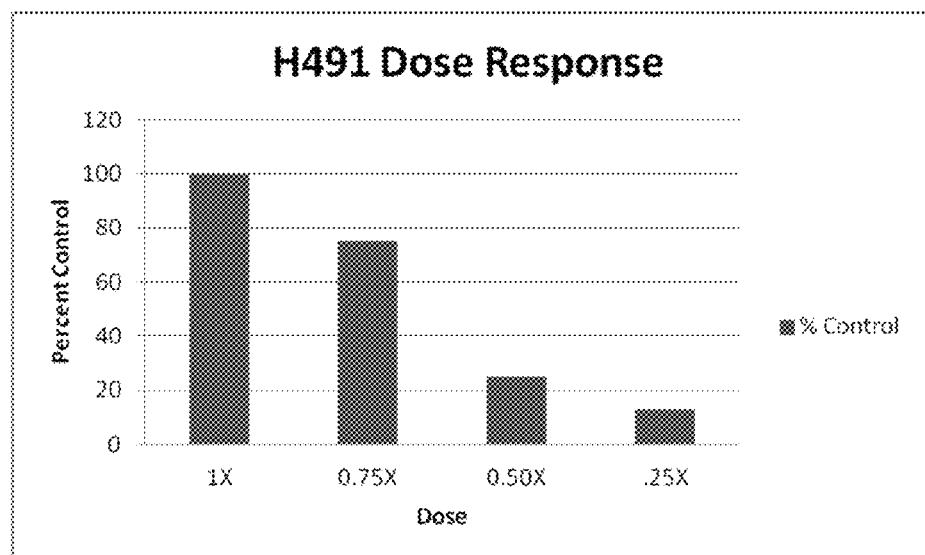
FIG. 6 shows the efficacy of H491 supernatant in the control of *M. hapla* at different dilution rates.

To evaluate the efficacy and stability of *B. megaterium* H491 whole cell broth, supernatant was tested for effect on J2 motility at different dilutions: 1×=full strength; 0.75×=75 ml H491 supernatant: 25 ml water; 0.50×=50 ml H491 supernatant: 50 ul water; 0.25×=25 ml H491 supernatant: 75 ml water. The motility of juvenile root-knot nematodes (J2's) was measured in an in vitro 96-well plastic cell-culture plate dose-response bioassay. This procedure is based on a visual grading of motility of the nematodes in each well treated with H491 where each treatment is tested in well repetitions of four: 100 ml of each microbial sample dilution was dispensed into its corresponding well followed by 30 ml of a 1:100 dilution of plant preservative material (PPM) solution that temporarily suppresses microbial growth. Finally, 50 ml of nematode solution, containing approximately 15 *M. hapla* J2 nematodes, was added and the plate was covered and incubated at 25° C. for 24 hours. The effect of each dilution sample was then visually scored and recorded. The results, shown in FIG. 6, indicate that the effect on motility ranged from about 15% non-motile at a four-fold dilution (0.25×), to 100% non-motile with full-strength supernatant (1×).

Example 11

Greenhouse Assays

A: Greenhouse Pot Assay: Cucumber with *Meloidogyne incognita*

To demonstrate the nematicidal activity of H491 supernatant against root knot nematodes (*Meloidogyne incognita*), a greenhouse study on cucumber (*Cucumis sativus*) cv. White Wonderwas conducted using a supernatant as the test product. One cucumber plant per pot was planted in autoclaved sand and grown in a greenhouse under natural day light. Two-week-old plants were treated with an 40-mL aliquot of the test product, after which 2000 fresh hatched *M. incognita* J2s were inoculated into each pot. A week later, a second 40 mL portion of the test product was applied at the same rate as before. Water, media blank, and Avid (0.1%) were used as negative, negative, and positive controls, respectively. There were five replicates for each test product, and the experiment was arranged in a randomized complete block design. Plants were grown in a greenhouse for four more weeks, after which each plant was harvested and evaluated for fresh shoot and root weights. The number of nematodes in each pot, and the number of root gallson each plant, were recorded.

Data presented in Table 5 below show that, although cucumber shoot and root fresh weights from plants treated with H491 supernatant were not statistically different from untreated controls, the pots treated with H491 supernatant contain significantly fewer nematodes than the untreated control pots. In addition, root gall number in H491 supernatant-treated cucumber plants was significantly less than in plants treated with water or media blank control. These results indicate that H491 supernatant is effective in restraining gall formation by *M. incognita* in cucumber.

TABLE 5

Effects H491 supernatant on *Meloidogyne incognita* Infestation in Cucumber in a Greenhouse Pot Assay.

| Treatment | Shoot Weight (g) | Root Weight (g) | Gall Number | Nematode Number |
|---|---|---|---|---|
| Avid | 15.2 ± 4.4 | 5.2 ± 2.1 | 0 ± 0 d | 316 ± 193 |
| Media | 24.3 ± 11.7 | 4.1 ± 2.5 | 19.6 ± 3.6 | 354 ± 195 |
| Water | 21.1 ± 2.6 | 6.3 ± 1.2 | 29.0 ± 8.2 | 510 ± 256 |
| H491 | 22.9 ± 5.6 | 5.6 ± 0.7 | 10.8 ± 2.8 | 332 ± 161 |

Data shown are means from two studies.

B: Greenhouse Pot Assay: Effect of H491 Supernatant on *Meloidogyne Hapla*-Infestation of Cucumber and Tomato Plants Greenhouse studies on cucumber (*Cucumis sativus*) cv. White Wonder and tomato (*Solanum lycopersicum*) cv. Roma were performed to demonstrate the nematicidal activity of H491 supernatant on root knot nematodes (M. hapla). One cucumber or tomato plant per pot was planted in autoclaved sand and grown in a greenhouse under natural day light. Pots containing two-week-old cucumber or three-week-old tomato plants were treated with a 40-mL aliquot of the test product per pot, after which 2000 fresh *M. hapla* juveniles were inoculated into each pot. A week later, a second treatment of the test product was applied to the pots at the same rate as before. Water, media, and Avid (0.1%) were used as negative, negative, and positive controls, respectively. There were five replicates for each test product, and the experiment was arranged in a randomized complete block design. Plants were grown in a greenhouse for four more weeks for cucumber and six more weeks for tomato, after which each plant was harvested and evaluated for fresh shoot and root weights and shoot height. Plant vigor and root galling index were rated on a 0-10 scale. For plant vigor, 0 represents dead and 10 represents most healthy; for root gall index, 0 represents no gall, and 10 represents 100% of roots galled. The number of nematodes in each pot was also recorded.

Results of the first trial are presented in Tables 6 and 7 for cucumber and tomato, respectively. H491 supernatant significantly reduced the root gall index in cucumber and the number of nematodes in cucumber and tomato compared with the water control. In the second trial, root gall index and number of nematodes were reduced by H491 in cucumber but not tomato (Tables 8 and 9). The results of both trials indicate that H491 supernatant reduces the number of galls in plants, and decreases the damage in plants from root-knot nematodes.

TABLE 6

Effects of H491 supernatant on *Meloidogyne hapla* in cucumber in a greenhouse pot assay trial one.

| Treatment | Plant Vigor[y] | Root Gall Index[z] | Nematode Population |
|---|---|---|---|
| H491 | 9 ± 1 | 2 ± 1 | 2233 ± 924 |
| Avid (1%) | 0 ± 0 | 0 ± 0 | 0 ± 0 |
| Media | 3 ± 1 | 7 ± 3 | 5233 ± 1097 |
| Water | 1 ± 1 | 8 ± 1 | 5467 ± 611 |

Data shown are means from two studies
[y]Plant vigor on a 0-10 scale: 0: dead, 10: the healthiest
[z]Root gall index on a 0-10 scale: 0: no gall, 10: 100% of roots galled

TABLE 7

Effects of H491 supernatant on *Meloidogyne hapla* in tomato in a greenhouse pot assay trial one.

| Treatment | Shoot Height (cm) | Shoot Weight (g) | Root Weight (g) | Root Gall Index | Nematode Number |
|---|---|---|---|---|---|
| H491 | 26 ± 1[z] | 17 ± 3 | 4.3 ± 2 | 2 ± 1 | 140 |
| Avid (1%) | 8 ± 8 | 1 ± 1 | 0.4 ± 1 | 0 ± 0 | 0 |
| Media | 31 ± 5 | 24 ± 4 | 4.8 ± 3 | 2 ± 2 | 267 |
| Water | 28 ± 6 | 14 ± 4 | 4.2 ± 1 | 2 ± 1 | 325 |

Data shown are means from two studies

TABLE 8

Effects H491 supernatant on *Meloidogyne hapla* in cucumber in a greenhouse pot assay trial two.

| Nematicidal candidate | Top weight | Root weight | Root gall index | Nematode number |
|---|---|---|---|---|
| Avid | 16.1 ± 4.5 | 4.9 ± 2.5 | 0.2 ± 0.4 | 1180 ± 920 |
| Media | 8.3 ± 2.6 | 2.1 ± 1.5 | 6.0 ± 1.2 | 3260 ± 1590 |
| Water | 5.9 ± 1.2 | 0.5 ± 0.3 | 7.2 ± 1.3 | 2580 ± 934 |
| H491 | 9.3 ± 2.1 | 1.4 ± 0.7 | 2.6 ± 1.0 | 1500 ± 412 |

Data shown are means from two studies

TABLE 9

Effects H491 supernatant on *Meloidogyne hapla* in tomato in a greenhouse pot assay trial two.

| Nematicidal candidate | Top weight | Root weight | Root gall index | Nematode number |
|---|---|---|---|---|
| Avid | 16.9 ± 4.8 | 6.2 ± 2.1 | 0 ± 0 | 332 ± 385 |
| Media | 21.5 ± 5.9 | 8.3 ± 1.3 | 2.2 ± 2.8 | 342 ± 355 |
| Water | 14.1 ± 1.1 | 5.7 ± 1.7 | 4.1 ± 3.2 | 334 ± 241 |
| H491 | 11.3 ± 4.6 | 4.4 ± 2.3 | 2.8 ± 3.8 | 332 ± 491 |

Data shown are means from two studies

Example 12

Immobilization of Nematodes in Infested Soil

In this example, the effect of *B. megaterium* H491 supernatant on the motility and viability of nematodes in infested soil was determined. These trials were conducted with field soils infested predominantly with sting or lance nematodes. Each trial consisted of 4 treatments: H491 supernatant, growth medium blank, a positive control (i.e. 0.1% Avid®) and a negative control (i.e. water). The trials were conducted as a randomized complete block design with 8 replications. Twelve liters of soil containing the desired nematodes were collected, separated from turf and roots, and homogenized. After mixing the soil, 5 (100 cm$^3$) soil samples were extracted using a centrifugation-sugar flotation method and, for each sample, the number of nematodes of each type was counted to ensure even distribution of the major nematodes of interest (sting or lance) throughout the soil. Next, 200 cm$^3$ portions of nematode-containing soil were measured out and placed into a 2×2×2-inch plastic pot. The treatments were applied as a drench treatment (40 ml/pot). The pots were then placed on a lab bench and left for 72 hours to expose the nematodes to the treatments.

Next, the soil from each pot was washed onto a modified Baermann apparatus for nematode extraction. The Baermann apparatus allows live nematodes to move out of the soil, through a filter, and into water, where they can be counted.

Dead or immotile nematodes remain in the soil. After incubating the Baermanns for 96 hours, the live nematodes were collected and counted. Nematode counts from each treatment were compared with SAS 9.2 using Fisher's LSD mean separation at P≤0.05 for all nematodes observed.

The effects of H491 supernatant on four plant-parasitic nematode genera were determined. These four genera, observed in the field soil used to conduct the sting bench trial, were: sting nematode, lance nematode, *Peltamigratus* sp. and *Scutellonema* sp. Sting nematode counts were increased by 5% in soil exposed to growth medium, compared to soil exposed only to water. Compared to negative control (soil exposed to water) soil exposed to Avid or H491 supernatant experienced a 14% decrease in sting nematode number.

*Peltamigratus* sp. counts were decreased by 7%, 32%, and 88% after treatment of soil with medium, H491 supernatant and Avid, respectively; compared to the negative control (water). *Scutellonema* sp. counts were unchanged in the soil treated with growth medium, compared to the negative control (water), and decreased by 17% and 75% in soil treated with H491 and Avid, respectively, compared to the negative control (water). Lance nematode counts were decreased by 9%, 35%, and 69% in soil subjected to treatments with medium, H491 supernatant, and Avid, respectively, compared to the water control.

Example 13

Extraction and Isolation of Compounds from *B. Megaterium* H491 Culture Supernatant The following procedure was used for the purification of compounds from cultures of *B. megaterium*. Briefly, a crude extract of *B. megaterium* H491 culture broth was extracted with Amberlite, and the crude extract was fractionated by vacuum liquid chromatography. An active VLC fraction was further fractionated by HPLC, and active compounds were identified. The nematicidally active compound 4-Phenylbutanoic acid (Compound 1) was obtained from VLC fraction 3, as described below.

Liquid Chromatography of Crude Extract

The culture broth obtained from a 10-L fermentation of *B. megaterium* in V-8-broth was extracted with Amberlite XAD-7 resin (Asolkar et al., 2006) by shaking the cell suspension with resin at 225 rpm for two hours at room temperature. The resin and cell mass were collected by filtration through cheesecloth and washed with deionized water to remove salts. The resin, cell mass, and cheesecloth were then soaked for 2 h in acetone/methanol (50/50) after which the acetone/methanol was filtered and dried under vacuum, using a rotary evaporator, to yield a crude extract. The crude extract was fractionated by reversed-phase C18 vacuum liquid chromatography ($H_2O/CH_3OH$; gradient 80:20% to 0:100%) into 6 fractions (FIG. 1). These fractions were concentrated to dryness using a rotary evaporator, and the resulting dry residues were screened for biological activity using *M. incognita* and *M. hapla*.

Assay for Biological Activity of VLC Fractions of *Bacillus megaterium* Extract

Figure 7:
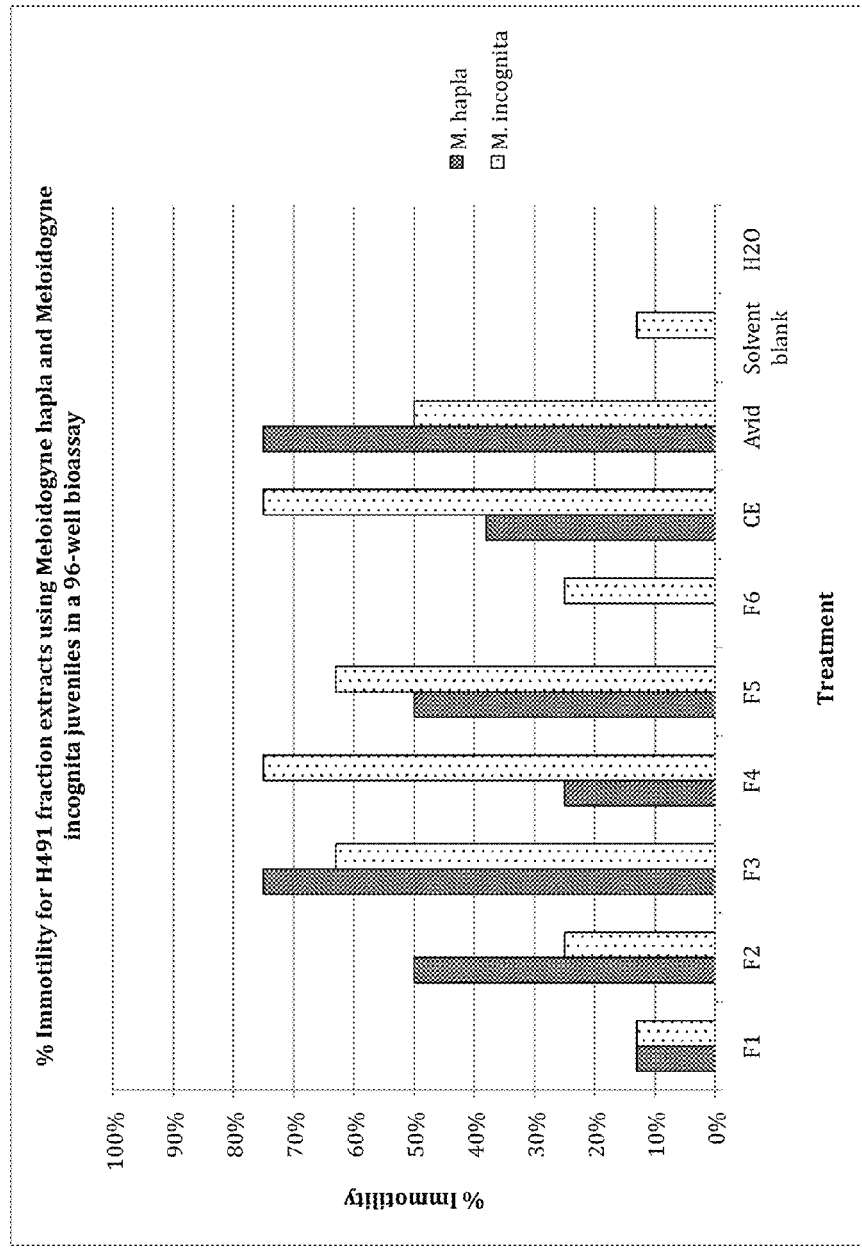
FIG. 7 shows the results of two different 96-well plate extract bioassays of H491 fractions 1-6 and crude extract. Three controls are included in each trial; 1 positive (1% Avid) & 2 negative (DMSO & water). Trial 1 (T1) was carried out using *M. hapla* nematodes and the fractions were dissolved in 100% DMSO; and trial 2 (T2) was carried out using *M. incognita* nematodes and the fractions were dissolved in DMSO. The % immotility is graphed in its corrected form where the reported immotility of DMSO blank is subtracted from each of samples tested.

VLC fractions 1-6 were dissolved in dimethylsulfoxide (DMSO) and tested in an in vitro 96-well plastic cell-culture plate extract bioassay to identify the fraction/s that contain the desired active metabolite/s. To test for biological activity, 15-20 J2 nematodes in 50 ml of water were exposed to 100 ml of a 4 mg/ml fraction concentrate for 24 hours at 25° C. Each fraction was tested in quadruplicate. Results were recorded based on a visual grading of immotility of the juvenile nematodes (J2's) in each well. Results are shown in FIG. 7.

Reverse Phase HPLC Fractionation of VLC Fractions

The active fractions were subjected to reversed phase HPLC on a Spectra System P4000 system (Thermo Scientific) to provide pure compounds, which were then screened in bioassays as described above to identify active compounds. To confirm the identity of the compounds, additional spectroscopic data such as LC/MS and NMR were recorded.

Fraction 3 (above) was applied to a HPLC C-18 column (Phenomenex, Luna 10u C18(2) 100 A, 250×30), and the column was developed with a water:acetonitrile gradient solvent system (0-10 min, 80-70% aqueous $CH_3CN$; 10-45 min, 70-50% aqueous $CH_3CN$; 45-55 min, 35-30% aqueous $CH_3CN$; 55-60 min, 30-20% aqueous $CH_3CN$; 60-65 min, 20-0% aqueous $CH_3CN$; 65-75 min, 100% $CH_3CN$; 75-80 min, 0-80% aqueous $CH_3CN$) at 7 mL/min flow rate with UV detection at 210 nm. The active compound 4-Phenylbutanoic acid (1), had a retention time 47.85 min.

Assay or Biological Activity of HPLC Fractions

Figure 8:
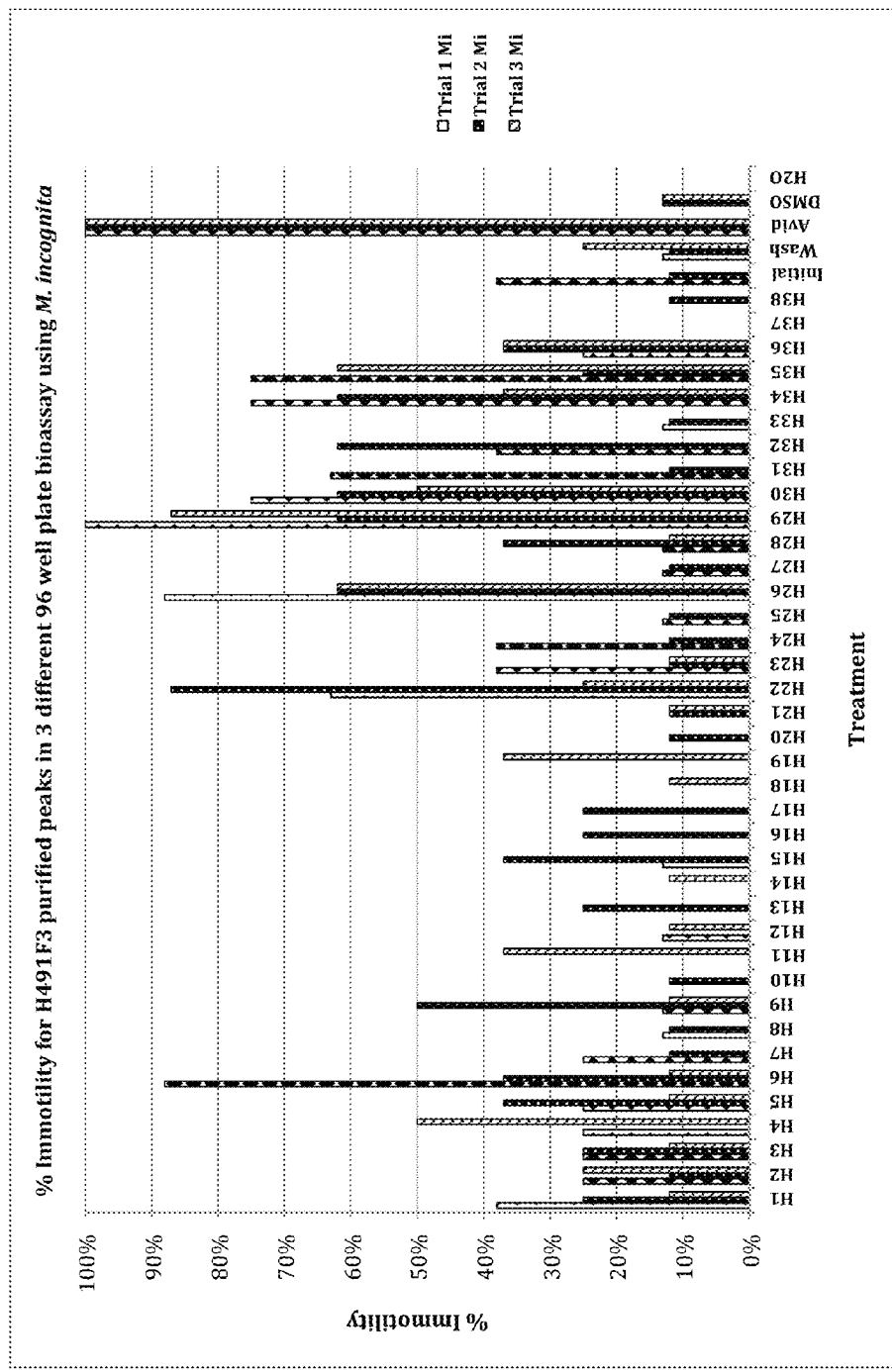
FIG. 8 shows the results of three different 96-well plate extract bioassays of H491 purified peaks H1-H38. Three controls are included in each trial; a positive control (1% Avid) and 2 negative controls (DMSO & water). Column load (Initial) and flow-through (Wash) were also assayed. Trial 1 (T1) was carried out with *M. hapla* nematodes, trials 2 and 3 (T2 and T3) were carried out with *M. incognita* nematodes. Results for each sample (fraction or control) are presented as a set of three bars: the leftmost bar show results for Trial 1 (*M. hapla*), the center bar shows results for Trial 2 (*M. incognita*) and the rightmost bar shows results for Trial 3 (*M. incognita*).

Each HPLC peak was tested in an in vitro 96-well plastic cell-culture plate extract bioassay in order to identify the peak/s that contain the desired active metabolite/s. For these assays, 15-20 nematodes in a 50 ml water solution were exposed to 3 ml of a 20 mg/ml peak concentrate for a 24 hour period at 25° C. Once the incubation period was completed, results were recorded based on a visual grading of immotility of the juvenile nematodes (J2's) in each well treated with H491 purified peaks H1-H38; each treatment was tested in well repetitions of four. The results, shown in FIG. 8, indicate that H491 produces numerous compounds with pesticidal activity. Fraction 29 was selected for further analysis and testing.

Mass Spectroscopic Analysis of Compounds

Figure 2:
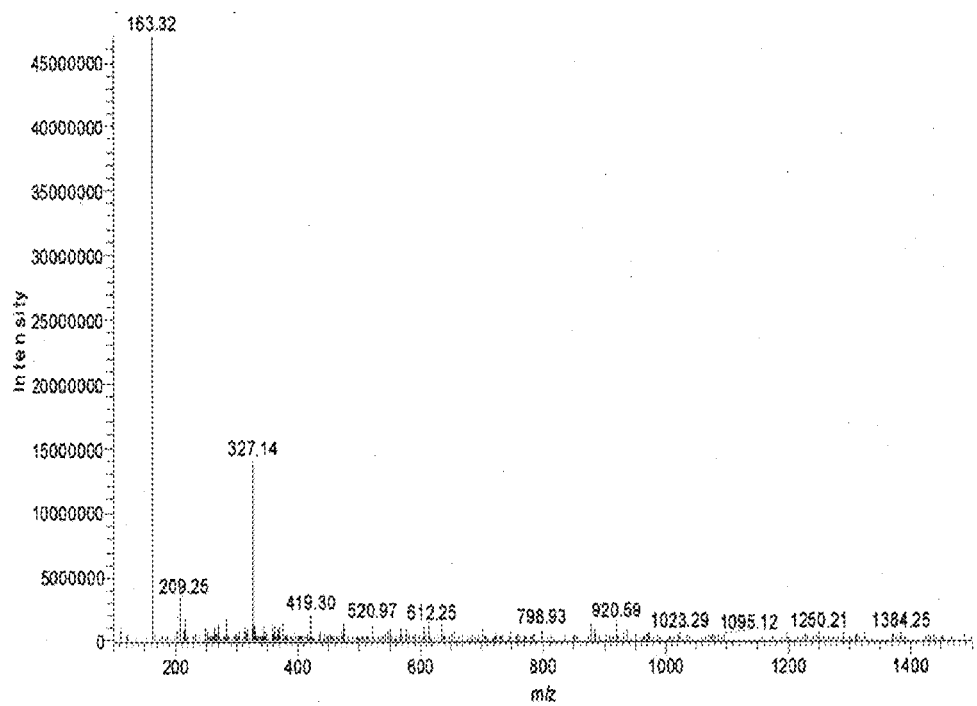
FIG. 2 depicts the (−) ESI-LCMS data for 4-Phenylbutanoic acid (1).

Mass spectroscopy of active peaks, isolated by HPLC using the procedure set forth above, was performed on a Thermo Finnigan LCQ Deca XP Plus electrospray (ESI) instrument using both positive and negative ionization modes in a full scan mode (m/z 100-1500 Da) on a LCQ DECA XP$^{plus}$ Mass Spectrometer (Thermo Electron Corp., San Jose, Calif.). Thermo high performance liquid chromatography (HPLC) instrument equipped with Finnigan Surveyor PDA plus detector, autosampler plus, MS pump and a 4.6 mm×100 mm Luna C18 5µ 100 A column (Phenomenex). The solvent system consisted of water (solvent A) and acetonitrile (solvent B). The mobile phase begins at 10% solvent B and was linearly increased to 100% solvent B over 20 min and then kept for 4 min, and finally returned to 10% solvent B over 3 min and kept for 3 min. The flow rate was 0.5 mL/min. The injection volume is 10 µL and the samples were kept at room temperature in an auto sampler. The compounds were analyzed by LC-MS utilizing the LC and reversed phase chromatography. Mass spectroscopy analysis of the present compounds is performed under the following conditions: The flow rate of the nitrogen gas was fixed at 30 and 15 arb for the sheath and aux/sweep gas flow rate, respectively. Electrospray ionization was performed with a spray voltage set at 5000 V and a capillary voltage at 35.0 V. The capillary temperature was set at 400° C. The data was analyzed on Xcalibur software. The 4-Phenylbutanoic acid (1) exhibited a molecular mass of 163.34 in negative ionization mode (see FIG. 2).

NMR Spectroscopic Analysis of Compounds

NMR spectra were measured on a Bruker 600 MHz gradient field spectrometer. The reference is set on the internal standard tetramethylsilane (TMS, 0.00 ppm).

Figure 3:
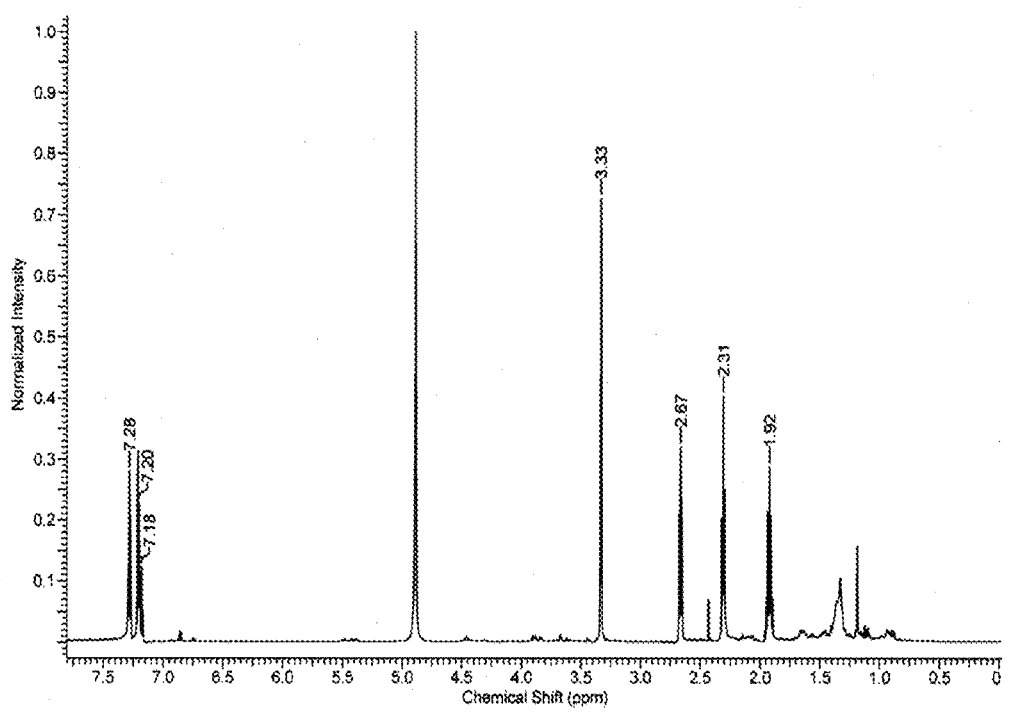
FIG. 3 depicts $^1$H NMR for 4-Phenylbutanoic acid (1) in $CD_3OD$-$d_4$ at 600 MHz.
Figure 4:
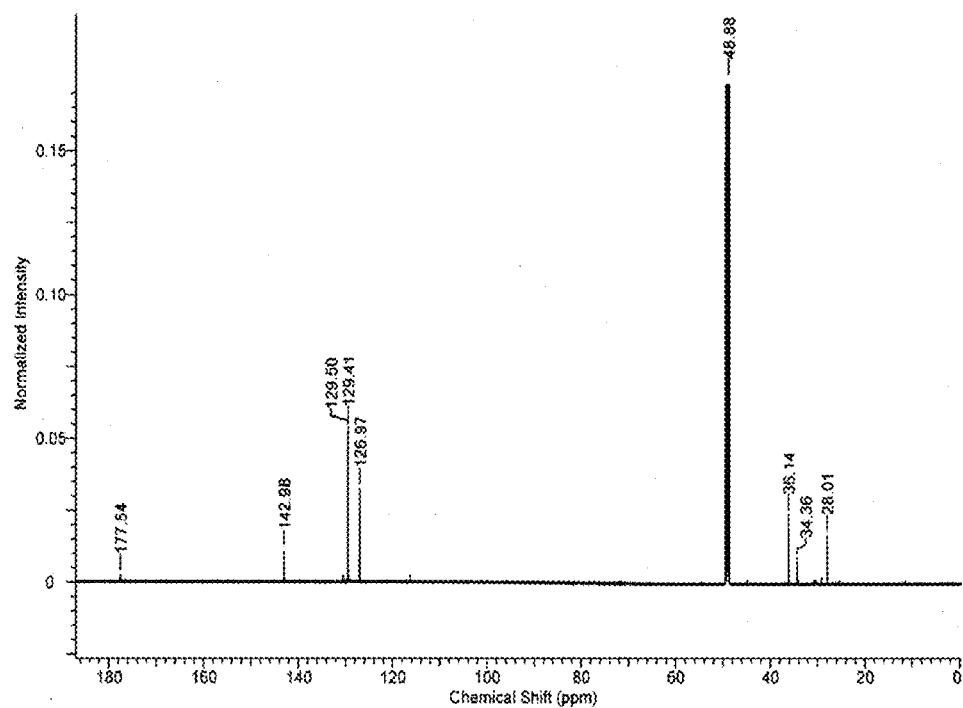
FIG. 4 depicts $^{13}$C NMR for 4-Phenylbutanoic acid (1) in $CD_3OD$-$d_4$ at 150 MHz.

For structure elucidation, the purified 4-Phenylbutanoic acid (1) with molecular weight 164 was further analyzed using a 600 MHz NMR instrument. $^1$H NMR δ values at 7.28 (2H), 7.19 (2H), 7.17, 2.67, 2.31, and 1.92 were detected (see FIG. 3). $^{13}$C NMR values of 177.5, 142.9, 129.5, 129.5, 129.4, 129.4, 126.9, 36.1, 34.4, and 28 were detected (see FIG. 4). The active compound was isolated as a colorless solid, with UV absorption bands at 220 & 283 nm. The negative electrospray ionization mass spectrum revealed molecular ion peak at m/z 163.32 [M-H]$^-$ and 327.14 [2M-H]$^-$ suggesting a molecular weight of 164, which is consistent with the molecular formula $C_{10}H_{10}O_2$ (with 5 degrees of unsaturation). The $^1$H NMR spectrum exhibited signals indicative of the presence of a mono substituted aromatic ring (δ 7.28, 2H, d, J=7.7 Hz; 7.19, 2H, d, J=7.7 Hz; 7.17 1H, t, J=7.7 Hz). Furthermore, the $^1$H NMR spectrum revealed the presence of three methylene groups, at δ 2.62, 2H, t, J=7.92 Hz, 2.30, 2H, t, J=7.65 and 1.92, 2H, q, J=7.65 Hz. The $^{13}$C NMR spectrum of Compound (I), interpreted with the help of the HSQC experiment, indicated the presence of 10 carbon atoms, including one carbonyl ($δ_c$ 177.5); six sp$^2$ carbons, one of which is unprotonated ($δ_c$ 142.9); five protonated carbon atoms ($δ_c$ 129.5, 129.5, 129.4, 129.4, 126.9); and three methylenes ($δ_c$ 36.1, 34.4, 28.1). The analysis of the COSY and HSQC correlation revealed two spin systems, one involving three methylene groups of the structure —CH$_2$—CH$_2$—CH$_2$—, and the other comprising a mono substituted benzene ring. From the detailed analysis of COSY, HMQC and HMBC experiments, the structure for the compound was assigned as 4-phenylbutanoic acid. The assigned structure was confirmed by comparison with a synthetic sample. This compound has been isolated from the marine bacterium *B. pumilus* S6-15, which inhibits biofilm formation in gram positive and gram negative species (Nithya et al., 2011).

Example 14

Greenhouse Cone Assay: Effect of *Meloidogyne incognita* on Tomato Seedlings Greenhouse studies on tomato (*Solanum lycopersicum*) cv. UC 82 were performed to test the nematicidal activity of H491 supernatant on root knot nematodes (*M. incognita*). One 25-day-old tomato seedling per cone container (Stuewe & Sons, Inc, Tangent, Oreg.) was transplanted into autoclaved sand and soil mix (2:1) and grown in a greenhouse under natural day light. 16 days after transplanting, each tomato seedlings (3-4 true leaves) was drenched with a 10-ml aliquot of whole cell broth (WCB) of H491 and other test products by pouring the aliquot directly onto the soil surface. Thereafter, 4000 eggs of *M. incognita* suspended in 1 ml of water were inoculated into three 6-cm-deep holes around the stems in each cone. A week later, a second drench was applied to the cones at the same rate as the first drench. Water and Avid (625 ppm) were used as negative and positive controls, respectively. There were four replicates and the experiment was arranged in a randomized complete block design. Plants were grown in a greenhouse for 3 weeks before being taken down. Each plant was then evaluated for phytotoxicity, fresh top (or shoot) weight, fresh root weight, gall numbers per root and gall index based on a 0 to 10 scale (0=no galls, 10=100% of roots galled). There was no phytotoxicity observed during the incubation period of the test. Statistical analysis (ANOVA) was performed using Fisher test, and the statistical differences among treatment means were calculated at P≤0.05.

Results are presented in Table 10. H491 WCB significantly reduced the gall index, number of galls per root and number of galls per gram of root compared with the water control. The plants treated with H491 had heavier fresh topweight than those treated with water. No significant difference was observed on the fresh root weight between treatments.

TABLE 10

Effects of H491 whole cell broth (WCB) on *Meloidogyne incognita* in tomato in a greenhouse cone assay$^x$

| Treatment | FTW (g)$^y$ | FRW (g)$^y$ | gall index$^z$ | galls/root | galls/g of root |
|---|---|---|---|---|---|
| H491 | 10.74 ± 0.34$^a$ | 6.1 ± 0.59$^a$ | 2.3 ± 0.96$^b$ | 142.5 ± 69.70$^b$ | 22.7 ± 9.28$^b$ |
| water | 7.35 ± 6.03$^b$ | 5.43 ± 1.37$^a$ | 6.5 ± 1.29$^a$ | 271.8 ± 53.60$^a$ | 54.1 ± 25.20$^a$ |
| avid | 8.43 ± 1.36$^{ab}$ | 5.33 ± 1.33$^a$ | 0 ± 0.00$^c$ | 1.0 ± 2.00$^c$ | 0.24 ± 0.48$^b$ |
| p-value | 0.038 | 0.606 | 0 | 0 | 0.003 |

$^x$Data are means ± standard deviations (SD) with 4 replicates. The values followed by the same letter in the same column were not significantly different, according to Fisher's least significant difference at P ≤ 0.05.
$^y$FTW: fresh top weight; FRW: fresh root weight.
$^z$gall index on a 0 to 10 scale: 0: no gall; 10: 100% of roots galled.

Example 15

Dose Response for H491 Whole Cell Broth in Mini Tube in Planta Bioassay

H491 *Bacillus megaterium* whole cell broth (WCB) was tested in an in planta bioassay at 3 different dilutions in water (1×, 0.7×, and 0.5× v/v) to determine the potency of the WCB against *Meloidogyne incognita* juveniles. This test is a miniature greenhouse pot test in which sterile falcon tubes were modified by cutting the top 1.5 inches off and making holes in the bottom to allow drainage. The tubes were filled with a mixture of sand and soil (1:2) and drenched with 2 mL aliquots of H491 whole cell broth (50, 70 and 100%), Avid (label rate) as positive control, and water as negative control. After drenching, cucumber seeds (cv. SMR58) were planted and then the tubes were inoculated with 800 eggs of *M. incognita*. The tubes were covered with parafilm and placed in a box with wet paper towels to ensure high humidity.

After 4 days, most of the seed had germinated and the parafilm cover was removed. After one week, a second dose (1 mL) was applied. The test was terminated after two weeks and fresh top weight, fresh root weight and gall index (scale: 1 unhealthy roots-10 healthy roots) were assessed.

Figure 10:
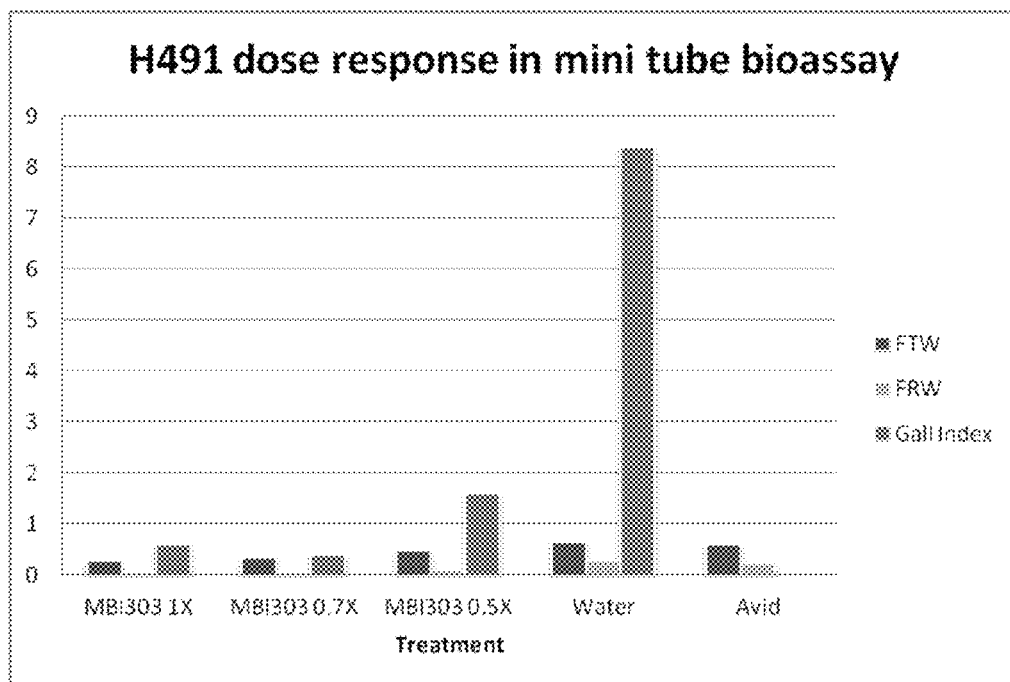
FIG. 10 shows nematicidal dose-response for H491 WCB in cucumber plants tested in a mini tube in planta assay. H491 WCB (identified as MBI303 in the Figure) was used at full strength (1×) and at 0.7× and 0.5× dilutions. Fresh top weight (FTW, left-most bar in each set of three), fresh root weight (FRW, center bar in each group of three) and gall index (right-most bar in each set of three) were measured for the three concentrations of H491 WCB and for plants treated with water (negative control) and with Avid (Positive control).

The results, shown in FIG. 10, indicate that gall index was reduced at all concentrations of H491 whole cell broth tested.

Example 16

In Vitro Motility Assay

Figure 11:
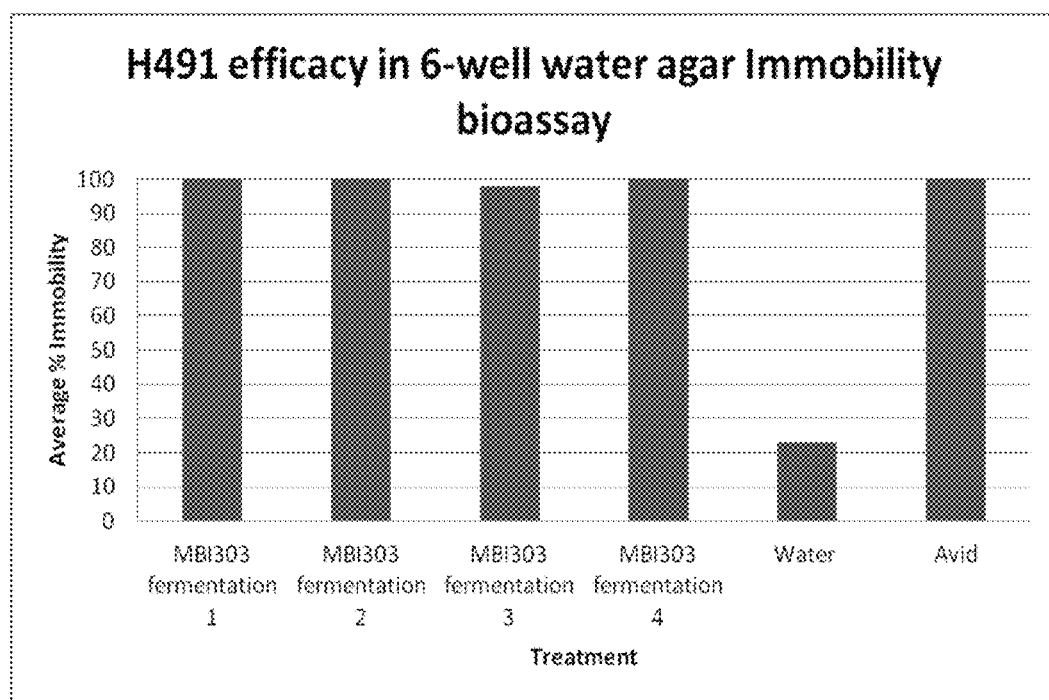
FIG. 11 shows results of motility assays (expressed as percentage of immotile nematodes) conducted with WCB obtained from four different fermentation batches of *B. megaterium* H491. Also shown are results for nematodes treated with water (negative control) and Avid (positive control).

H491 WCB obtained from four separate fermentation batches was tested in an in vitro motility assay. In this assay, M. incognita juveniles (J2) were exposed to test samples in a 96-well flat bottom plate. After 24 hours the juveniles were transferred into 6-well plates containing 1.5% water agar, to allow potential recovery. Motility was measured by counting the number of juveniles (J2) that moved out of the initial area after another 24 hours. The results are shown in FIG. 11. The data indicates that, for all four batches of H491 WCB, 100% immobilization was achieved after 24 hour exposure.

Example 17

Plant Growth Promotion Capabilities of B. Megaterium H491

B. megaterium H491 was tested for plant growth promotion markers on five different plate assays, and representative results are shown in Table 11. The bacterium was able to solubilize phosphate and produced the enzyme ACC deaminase. It was also capable of growing on methanol as carbon source. These results suggested that B. megaterium H491 can promote growth and confer stress tolerance to plants.

TABLE 11

|  | Phosphate sol. | ACC deaminase | IAA* | CAS* | AMS* |
|---|---|---|---|---|---|
| H491 | +++ | +++ | + | − | ++ |

*IAA: indole acetic acid; CAS: Chrome azurol S; AMS: Ammonium mineral salts

Example 18

Growth Promoting Activity on Soy and Sorghum

To test for the ability of B. megaterium H491 to promote plant growth, two seedling vigor assays were performed on soy and sorghum. Strain H491 was grown on an agar plate and a few colonies were transferred to 50 ml sterile Luria broth (LB: 25 g/l) and incubated at 25° C., 180 rpm for 24 h. Bacterial cells were harvested from the LB cultures by centrifugation at 3220×g for 20 minutes. The supernatant was discarded and the cells were washed in 20 ml sterile $MgSO_4$ buffer then centrifuged for a second time at 3220×g for 20 minutes. After discarding the supernatant, the cells were re-suspended in a small volume of sterile buffer. The concentration of cells in the suspension was determined by measuring the absorbance at 600 nm in a spectrophotometer. Seeds were treated with the cell suspension by imbibition. A cell inoculum ($1 \times 10^8$ CFU/ml) was dispensed over the seeds, in a 50 ml Falcon tube, at a rate of 0.6 ml per gram of seed (for seed with 250-300 seed/g). The seed and inoculum were incubated overnight at 25° C., and treated seeds were then dried in a sterile hood for 30 min. The negative control was prepared in the same manner, except the cell inoculum was replaced with sterile buffer. Growth promotion was evaluated by measuring fresh weight of seedlings, as shown in Table 12. For soy, the seedling weight doubled with the H491 treatment. For sorghum, a 64% increase of the fresh weight was observed.

TABLE 12

|  | Control (Buffer) | H491 treated |
|---|---|---|
| Soy | 5.46 | 11.22 |
| Sorghum | 0.89 | 1.46 |

Example 19

Growth Promoting Activity on Corn

Corn seeds were planted and drenched at planting time and one week after planting with B. megaterium H491 whole cell broth (WCB). A total of 10 plants per pot and 9 pots per treatment were planted and evaluated. Total fresh weight was recorded 2 weeks after planting, and statistical analysis was performed using Minitab ANOVA Tukey's.

The results are shown in Table 13. In corn plants treated with H491 WCB, a significant increase in vegetative fresh weight was observed, with a 95% simultaneous confidence interval as assessed by Tukey's.

TABLE 13

|  | Whole cell broth | |
|---|---|---|
| Corn | Control | H491 |
| AVG | 21.48 | 30.07 |
| SD | 4.02 | 2.42 |

Example 20

Effect of Compound 1 on Nematode Motility

HPLC fraction H29 (Example 13 and FIG. 8) was determined to be 4-phenylbutanoic acid. In this example, 4-phenylbutanoic acid (Compound 1) was synthesized and tested for dose-response in a nematode motility assay. M. incognita juveniles (J2) were exposed to different concentrations of 4-phenylbutanoic acid in a 96-well flat bottom plate for 24 hours. Juveniles were then transferred into 6-well plates containing 1.5% water agar to allow recovery. After a further 24 hours, motility was determined by counting the number of juveniles (J2) that had moved out of the initial area. Water and DMSO were used as negative controls, and Avid as a positive control.

Figure 12:
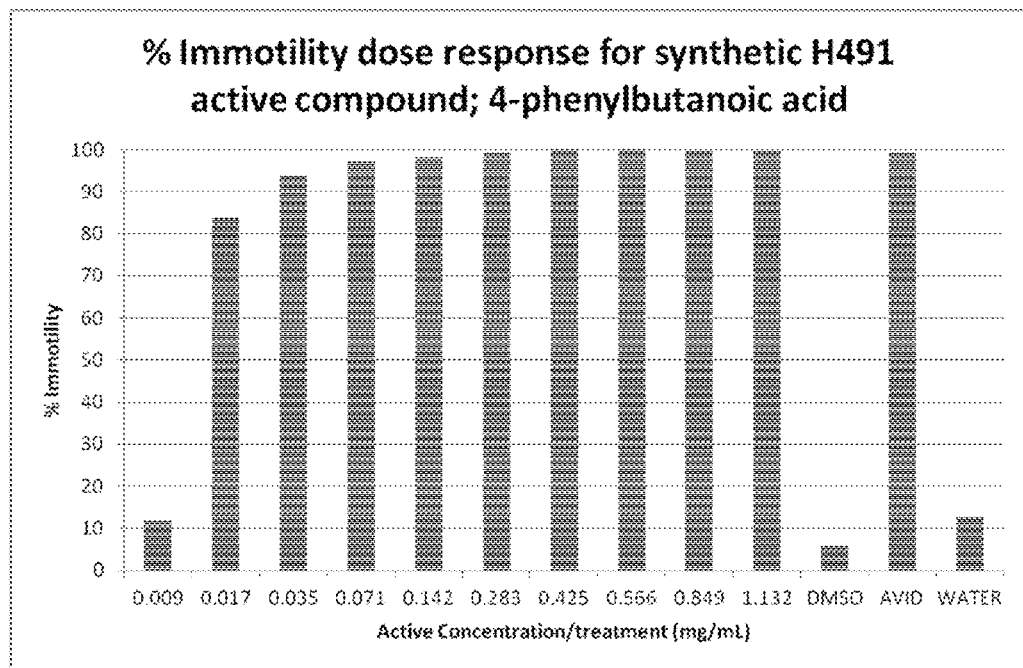
FIG. 12 shows the effect of 4-phenylbutanoic acid (Compound I), at different concentrations (indicated on the abscissa) on juvenile nematode (J2) motility. Results for negative controls (DMSO and water) and a positive control (Avid) are also shown.

The results are shown in FIG. 12. Using 75% immotility as a threshold for nematicidal activity, concentrations of 4-phenylbutanoic acid of 0.017 mg/ml or greater provided substantial nematicidal activity.

Example 22

Nematicidal Activity of Three Isolates of B. Megaterium

Figure 13:
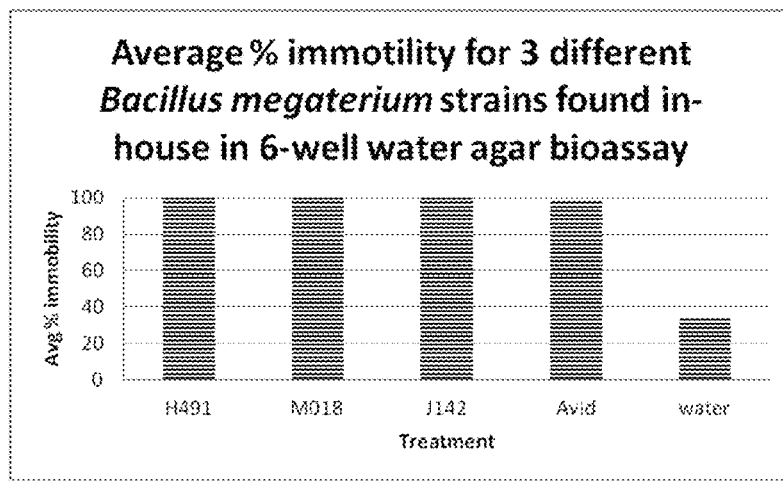
FIG. 13 shows the effects of three different strains of *B. megaterium* (H491, M018 and J142) on *M. incognita* J2 motility. Avid was used as a positive control, and water as a negative control.

Isolates of B. megaterium H491, M018 and J142 were cultured. Whole cell broth from each of the three cultures was tested in the water agar immotility assay described in Example 21. The results, shown in FIG. 13, indicate that whole cell broth from all three of the strains are able to render essentially 100% of juveniles immotile.

Deposit of Biological Material

The following biological material has been deposited under the terms of the Budapest Treaty with the Agricultural Research Culture Collection (NRRL), 1815 N. University Street, Peoria, Ill. 61604 USA, and given the following number:

| Deposit | Accession Number | Date of Deposit |
| --- | --- | --- |
| *Bacillus megaterium* strain H491 | NRRL B-50769 | Aug. 3$^{rd}$, 2012 |
| *Bacillus megaterium* strain M018 | NRRL B-50770 | Aug. 3$^{rd}$, 2012 |
| *Bacillus megaterium* strain J142 | NRRL B-50769 | Aug. 3$^{rd}$, 2012 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

References

Aksoy, H. M. and Ozman-Sullivan, S. K., 2008, Isolation of *Bacillus megaterium* from *Aphis* pomi (*Homoptera: aphididae*) and assessment of its pathogenicity *J. Plant Pathology* 90:449-452

Asolkar, R. N., Jensen, P. R., Kauffman, C. A., Fenical, W. 2006. Daryamides A-C, Weakly Cytotoxic Polyketides from a Marine-Derived Actinomycete of the Genus *Streptomyces* strain CNQ-085 *J. Nat. Prod.* 69:1756-1759.

Damberg, M., Russ, P., Zeeck, A. (1982). Die constitution der fungistatischen ansamycin-antibiotics ansatrienin A and B. *Tetrahedron Lett.* 23, 59-62.

Hebeda, R. E., Styrlund, C. R., Teague, W. M. (1988). Benefits of *Bacillus megaterium* amylase in dextrose production. *Starch* 40, 33-36.

Hu, X. and Boyer, G. H. (1995). Isolation and characterization of the siderophore N-deoxyschizokinen from *Bacillus megaterium* ATCC 19213. *BioMetals*, 8, 357-64 (Japan. Pat., 83 164 561. (1983)).

Izawa, M., Wada, Y., Kasahara, F., Asai, M., Kishi, T. (1981). Hydroxylation of ansamitocin P-3. *J. Antibit.*, 34 1591-1595.

Kittsteiner-Eberle, R., Ogbomo. I., Schmidt, H. L. (1989). Biosensing devices for the sen automated control of dehydrogenase substrates in fermentations. *Biosensors* 4, 75-85.

Komatsu, Y., Hayashi, H. (1998). Histone deacetylase inhibitors up-regulate the expression of cell surface MHC class-I molecules in B16/BL6 cells. *J. Antibiot.* 51, 89-91.

Martin, L., Prieto M. A., Cortes, E., Garcia, J. L. (1995). Cloning and sequencing of the pac gene encoding the penicillin G acylase of *Bacillus megaterium* ATCC 14945. *FEMS Microbiol Lett* 125, 287-292.

Metz, R. J., Allen, L. N., Cao, T. M., Zeman, N. W. (1988). Nucleotide sequence of an amylase gene from *Bacillus megaterium*. *Nucleic Acids Res.* 16, 5203.

Nagao, T., Mitamura, T., Wang, X. H., Negoro, S., Yomo, T., Urabe, I., Okada, H. (1992). Cloning, nucleotide sequences, and enzymatic properties of glucose dehydrogenase isozymes from *Bacillus megateriuni* IAM 1030. *J. Bacteriol.* 174, 5013-5020.

Nakahama, K., Izawa, M., Asai, M, Kida, M., Kishi, T. (1981). Microbial conversion of anamitocin. *J. Antibiot.*, 34 1581-1586.

Nithya, C., Devi, M. G., Pamdian, S. K. 2011. A novel compound from the marine bacterium *Bacillus pumilus* S6-15 inhibits biofilm formation in gram-positive and gram-negative species. *Biofouling*, 27, 519-528.

Plowman, J. E., Loehr, T. M., Goldman, S. J., Sanders-Loehr, J., (1984). Structure and siderophore activity of ferric Schizokinen. *J. Inorg. Biochem.*, 20, 183-186.

Shimada, N., Hasegawa, S., Harada, T., Tomisawa, T., Fujii, A., Takita, T. (1986). Oxetanocin, a novel nucleoside from bacteria, *J. Antibiot.*, 39, 1623-1625.

Shimada, N., Hasegawa, S., Saito, S., Nishikiori, T., Fujii, A., Takita, T. (1987). Derivatives of oxetanocin: oxetanocins H, X, G and 2-aminooxetanocin A. *J. Antibiot.*, 40, 1788-1790.

Suga, K., Shiba, Y., Sorai, T., Shioya, S., Ishimura, F. (1990). Reaction kinetics and mechanism of immobilized penicillin acylase from *Bacillus megaterium. Ann N Y Acad Sci.* 613, 808-815.

Takaichi, S. (1990). Heterogeneous position of the double bonds of unsaturated fatty acids in carotenoid glucoside esters from *Rhodococcus rhodochrous* RNMS1. *Agric. Biol. Chem.*, 54, 2139-2140.

Takasaki, Y. (1989). Novel maltose-producing amylase from *Bacillus megaterium* G-2. *Agric Biol Chem.* 53, 341-347.

Vandamme et al. Polyphasic taxonomic study of the emended genus *Arcobacter* with *Arcobacter butzleri* comb. nov. and *Arcobacter skirrowii* sp. nov., an aerotolerant bacterium isolated from veterinary specimens." Int. J. Syst. Bacteriol. 42: 344-356. 1992.

Vihinen, M., Mantsala, P. (1989). Microbial amylolytic enzymes. *Crit Rev Biochem Mol Biol.* 24, 329-418.

What is claimed is:

1. A composition comprising
   (a) whole cell broth collected from *Bacillus megaterium* H491 (NRRL Accession No. B-50769) fermentation which has pesticidal activity; and
   (b) at least one of a carrier, diluent, surfactant, or adjuvant.

2. The composition according to claim 1, further comprising a pesticide selected from the group consisting of a nematicide, a fungicide and an insecticide.

3. The composition according to claim 1, wherein said strain of *Bacillus megaterium* H491 (NRRL Accession No. B-50769) produces a pesticidal compound comprising 4-phenylbutanoic acid.

4. The composition according to claim 1, wherein said strain of *Bacillus megaterium* H491 (NRRL Accession No. B-50769) is non-pathogenic to vertebrate animals.

5. The composition according to claim 1, wherein said strain of *Bacillus megaterium* H491 (NRRL Accession No. B-50769) is susceptible to tetracycline.

6. The composition according to claim 1, wherein said strain of *Bacillus megaterium* H491 (NRRL Accession No. B-50769) is present in a formulation selected from the group consisting of an emulsifiable concentrate, a wettable powder, a soluble liquid, an aerosol, an ultra-low volume concentrate solution, a soluble powder, a microencapsulate, water-dispersed granules, a flowable, a micro emulsion and a nano-emulsion.

7. A method for modulating pest infestation in a plant, the method comprising applying to the plant and/or seeds thereof and/or substrate used for growing said plant an amount of the composition of claim 1 effective to modulate said pest infestation.

8. A method for isolating a compound comprising 4-phenylbutanoic acid which has pesticidal properties, wherein the method comprises the steps of:
   (a) culturing a *Bacillus megaterium* H491 (NRRL Accession No. B-50769) strain in a cell broth for a time and at a temperature sufficient to produce 4-phenylbutanoic acid; and
   (b) isolating said 4-phenylbutanoic produced in said whole cell broth.

9. A seed comprising the composition of claim 1, which has pesticidal properties.

10. A method for modulating (i) growth of a plant, and/or (ii) germination of a seed of said plant, the method comprising contacting said plant and/or its seed and/or its growth substrate with
    the composition of claim 1;
    in an amount effective to modulate said growth of said plant and/or germination of said seed.

11. The method according to claim 10, wherein said plant is selected from the group consisting of strawberry, squash, cucumber, tomato, rose, pepper eggplant, grapevine, cotton, onion, garlic, wheat, soy, corn and rice.

12. The method according to claim 10, further comprising transplanting said plant into said growth substrate.

13. The method according to claim 12, wherein prior to transplanting said plant into said growth substrate, one or more roots of said plant are treated with said composition of claim 1.

* * * * *